(12) United States Patent
Manabe et al.

(10) Patent No.: US 9,540,566 B2
(45) Date of Patent: Jan. 10, 2017

(54) DEVICES FOR HIGH-FREQUENCY TECHNOLOGY, LIQUID-CRYSTALLINE MEDIA AND COMPOUNDS

(71) Applicant: MERCK PATENT GESELLSCHAFT MIT BESCHRANKTER HAFTUNG, Darmstadt (DE)

(72) Inventors: Atsutaka Manabe, Bensheim (DE); Christian Jasper, Darmstadt (DE); Volker Reiffenrath, Rossdorf (DE); Elvira Montenegro, Weinheim (DE); Detlef Pauluth, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/921,698

(22) Filed: Oct. 23, 2015

(65) Prior Publication Data

US 2016/0046866 A1    Feb. 18, 2016

Related U.S. Application Data

(62) Division of application No. 13/513,208, filed as application No. PCT/EP2010/006961 on Nov. 16, 2010, now Pat. No. 9,193,905.

(30) Foreign Application Priority Data

Dec. 3, 2009    (DE) .................... 10 2009 056 560

(51) Int. Cl.
*C09K 19/52* (2006.01)
*C09K 19/12* (2006.01)
*C07C 1/32* (2006.01)
*C07C 15/14* (2006.01)
*H01Q 19/02* (2006.01)

(52) U.S. Cl.
CPC .............. *C09K 19/52* (2013.01); *C07C 1/321* (2013.01); *C07C 15/14* (2013.01); *C09K 19/12* (2013.01); *H01Q 19/02* (2013.01); *C07C 2531/24* (2013.01); *C09K 2019/523* (2013.01); *C09K 2219/11* (2013.01)

(58) Field of Classification Search
CPC ... C09K 19/52; C09K 19/12; C09K 2019/523; C09K 2219/11; C07C 1/321; C07C 15/14; C07C 2531/24; H01Q 19/02
USPC ............................ 252/299.01, 299.6, 299.66
See application file for complete search history.

(56) References Cited

U.S. PATENT DOCUMENTS 9,193,905 B2 * 11/2015 Manabe ................. C09K 19/12

* cited by examiner

*Primary Examiner* — Geraldina Visconti
(74) *Attorney, Agent, or Firm* — Millen White Zelano & Branigan, P.C.

(57) ABSTRACT

The present invention relates to a device for high-frequency technology, or for the microwave region and millimeter wave region of the electromagnetic spectrum, characterized in that it contains a liquid-crystal medium which consists of one or more compounds, which one or more compounds, which contain 6 to 15 five-, six- or seven-membered rings, preferably 1,4-linked phenylene rings, or in that it contains a liquid-crystal medium which itself comprises a component A, which itself consists of one or more of the said compounds, which one or more compounds, which contain 6 to 15 five-, six- or seven-membered rings, preferably 1,4-linked phenylene rings. The present invention additionally relates to compounds of the formula (I), in which the parameters have the meanings given in the text, and to the corresponding, novel liquid-crystal media, to the use and preparation thereof, and to the production and use of the devices. The devices according to the invention are particularly suitable phase shifters in the microwave and millimeter wave region, for microwave and millimeter wave array antennas and very particularly for so-called tunable "reflectarrays".

21 Claims, No Drawings

DEVICES FOR HIGH-FREQUENCY TECHNOLOGY, LIQUID-CRYSTALLINE MEDIA AND COMPOUNDS

AREA OF THE INVENTION

The present invention relates to novel devices for high-frequency technology, especially devices for high-frequency equipment, in particular antennas, especially for the gigahertz region, which are operated in the microwave or millimeter wave region. These devices use particular liquid-crystalline, chemical compounds or liquid-crystalline media composed thereof for, for example, the phase shifting of microwaves for tuneable phased-array antennas or for tuneable cells of microwave antennas based on "reflectarrays".

PRIOR ART AND PROBLEM TO BE SOLVED

Liquid-crystalline media have recently also been proposed for use in devices for high-frequency technology, in particular for microwave technology, such as, for example, in DE 10 2004 029 429 A and in JP 2005-120208 (A).

Liquid-crystalline media have long been utilised in electro-optical displays (liquid crystal displays—LCDs) in order to display information.

However, liquid-crystalline media have recently also been proposed for use in devices for microwave technology, such as, for example, in DE 10 2004 029 429 A and in JP 2005-120208 (A).

An industrially valuable application of liquid-crystalline media in high-frequency technology is based on their property that their dielectric properties can be controlled, particularly for the gigahertz region, by a variable voltage. This enables the construction of tuneable antennas which do not contain any moving parts (Gaebler, A., Moessinger, A., Goelden, F., et al., "Liquid Crystal-Reconfigurable Antenna Concepts for Space Applications at Microwave and Millimeter Waves", International Journal of Antennas and Propagation, Volume 2009, Article ID 876989, (2009), pages 1-7, DOI: 10.1155/2009/876989).

Penirschke, A., Müller, S., Scheele, P., Weil, C., Wittek, M., Hock, C. and Jakoby, R.: "Cavity Perturbation Method for Characterisation of Liquid Crystals up to 35 GHz", 34th European Microwave Conference—Amsterdam, pp. 545-548, describe, inter alia, the properties of the known single liquid-crystalline substance K15 (Merck KGaA, Germany) at a frequency of 9 GHz.

DE 10 2004 029 429 A describes the use of liquid-crystal media in microwave technology, inter alia in phase shifters. DE 10 2004 029 429 A has already investigated liquid-crystalline media with respect to their properties in the corresponding frequency range.

However, the compositions known to date are afflicted with disadvantages. Besides other deficiencies, most of them result in disadvantageously high losses and/or inadequate phase shifts or in low material quality ($\eta$).

For use in high-frequency technology, liquid-crystalline media having particular, hitherto rather unusual, unconventional properties, or combinations of properties, are required.

Thus, novel liquid-crystalline media having improved properties are necessary. In particular, the loss in the microwave region must be reduced and the material quality must be improved.

In addition, there is a need to improve the low-temperature behaviour of the devices. Both an improvement in the operating properties and also in the storage stability are necessary here.

There is therefore a considerable demand for liquid-crystalline media having suitable properties for corresponding practical applications.

Larios-López, L., Navarro-Rodriguez, D., Arias-Marin, E. M., Moggio, I. and Reyes-Casteneda, C. V., Liquid Crystals, 2003 Volume 30, No. 4, pages 423-433, describes oligo(p-phenyls) having five and having seven phenyl rings, which are substituted by alkoxy radicals in the terminal position and in some lateral positions. These compounds all have high melting points.

Banerjee M., Shukla, R. and Rathore, R., J. Am. Chem. Soc. 2009, Volume 131, pages 1780-1786, and the associated "supporting information", describes terminally substituted hexa- and hepta-p-phenylenes, which are likewise all high-melting compounds.

Laterally substituted decaphenyls of the formula

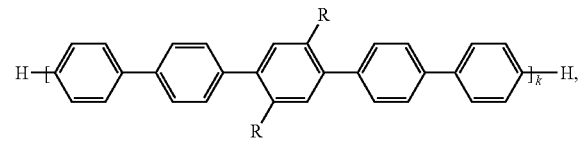

where k=1, 2 or 3 and R=n-hexyl or n-docdecyl, are disclosed in Rehahn, M. and Galda, P., Synthesis 1996, pages 614 to 620 (DOI: 10.1055/s1996-4260).

Bistolan compounds, also known as triphenyldiacetylenes, having an additional alkyl substitution on the central phenylene ring are adequately known to the person skilled in the art.

For example, Wu, S.T., Hsu, C.S. and Shyu, K.F., Appl. Phys. Lett., 74 (3), (1999), p. 344-346, discloses various liquid-crystalline bistolan compounds containing a lateral methyl group, of the formula

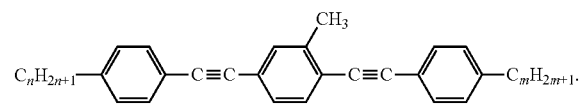

Besides liquid-crystalline bistolan compounds of this type containing a lateral methyl group, Hsu, C. S. Shyu, K. F., Chuang, Y. Y. and Wu, S.T., Liq. Cryst., 27 (2), (2000), p. 283-287, also discloses corresponding compounds containing a lateral ethyl group and proposes the use thereof, inter alia, in liquid crystal optically phased arrays.

Dabrowski, R., Kula, P. Gauza, S., Dziadiszek, J. Urban, S. and Wu, S.T., IDRC 08, (2008), pages 35-38, mentions dielectrically neutral bistolan compounds with and without a lateral methyl group on the central ring besides the strongly dielectrically positive isithiocyanatobistolan compounds of the formula

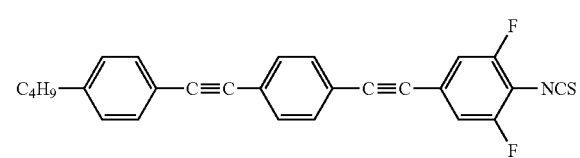

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (likewise Merck KGaA, Germany).

DE 10 2004 029 429 A describes the use of liquid-crystal media in microwave technology, inter alia in phase shifters. DE 10 2004 029 429 A has already investigated liquid-crystalline media with respect to their properties in the corresponding frequency range. In addition, it mentions liquid-crystalline media which comprise compounds of the formulae

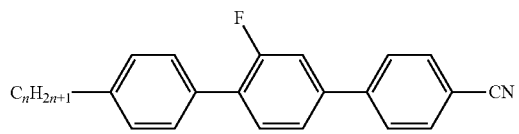

besides compounds of the formulae

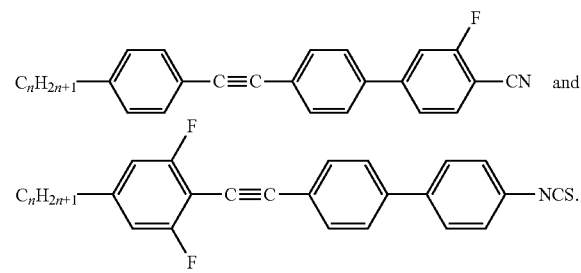

However, these compositions known to date are afflicted with serious disadvantages. Besides other deficiencies, most of them result in disadvantageously high losses and/or inadequate material quality.

For these applications, liquid-crystalline media having particular, hitherto rather unusual, unconventional properties, or combinations of properties, are required.

Novel liquid-crystalline media having improved properties are thus necessary. In particular, the loss in the microwave region must be reduced and the material quality improved.

In addition, there is a demand for an improvement in the low-temperature behaviour of the devices. Both an improvement in the operating properties and also in the shelf life are necessary here.

Thus, there is a considerable demand for liquid-crystalline media having suitable properties for corresponding practical applications.

PRESENT INVENTION

Surprisingly, it has now been found that it is possible to achieve devices for high-frequency technology which do not have the disadvantages of the prior-art materials, or at least only do so to a considerably reduced extent, if selected, liquid-crystalline compounds or media comprising these compounds are employed.

The present invention thus relates to a device for high-frequency technology, or for the microwave region and/or the millimeter region of the electromagnetic spectrum, characterised in that it contains a liquid-crystal medium which comprises or consists of a component A, which [lacuna] one or more compounds having 6 to 15 five-, six- or seven-membered rings, preferably 1,4-linked phenylene rings, which may optionally be substituted, preferably of the formula I

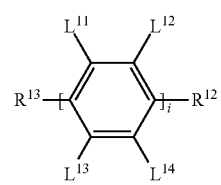

in which
$R^{11}$ and $R^{12}$, independently of one another, denote halogen, preferably F or Cl, unfluorinated alkyl or fluorinated alkyl or unfluorinated alkoxy or fluorinated alkoxy, each having 1 to 15 C atoms, or unfluorinated alkenyl or fluorinated alkenyl, unfluorinated alkenyloxy or unfluorinated alkoxyalkyl or fluorinated alkoxyalkyl, each having 2 to 15 C atoms, in which, in addition, one or more "—CH$_2$—" groups may be replaced, independently of one another, by cycloalkyl having 3 to 6 C atoms, preferably having 4 or 6 C atoms, and alternatively, in addition, one of $R^{11}$ and $R^{12}$ or both $R^{11}$ and $R^{12}$ denote H,
preferably
$R^{11}$ and $R^{12}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms,
particularly preferably
$R^{11}$ denotes unfluorinated alkyl having 1 to 7 C atoms or unfluorinated alkenyl, unfluorinated alkenyloxy or unfluorinated alkoxyalkyl, each having 2 to 7 C atoms, and
particularly preferably
$R^{12}$ denotes unfluorinated alkyl or unfluorinated alkoxy, each having 1 to 7 C atoms, and
$L^{11}$ to $L^{14}$ on each appearance, in each case independently of one another, denote H, alkyl having 1 to 15 C atoms, F or Cl, and
i denotes an integer in the range from 6 to 15, preferably from 6 or 8 to 12 and particularly preferably from 6 or 9 to 10,
and preferably
at least two of the substituents present
$L^{11}$ to $L^{14}$ have a meaning other than H, and they preferably denote alkyl, and
$R^{11}$ denotes $C_nH_{2n+1}$ or $CH_2=CH-(CH_2)_z$, and
$R_{12}$ denotes $C_mH_{2m+1}$ or $O-C_mH_{2m+1}$ or $(CH_2)_z-CH=CH_2$,
and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The present invention likewise relates to the compounds of the formula I in which $R^{11}$ and $R^{12}$ both have a meaning other than H.

Preference is given to compounds of the formula I or the use of compounds of the formula I in which
in the case where i is equal to 6 to 8,
$L^{11}$ to $L^{14}$ on each appearance, in each case independently of one another, denote H, alkyl having 1 to 8 C atoms, particularly preferably having 2 to 5 C atoms, F or Cl, and
preferably at least two of the substituents $L^{11}$ to $L^{14}$ present denote alkyl,
in the case where i is equal to 9 to 12,
$L^{11}$ to $L^{14}$ on each appearance, in each case independently of one another, denote H, alkyl having 3 to 10 C atoms, particularly preferably having 4 to 8 C atoms, F or Cl, and
preferably at least three, particularly preferably at least four, of the substituents $L^{11}$ to $L^{14}$ present denote alkyl,
in the case where i is equal to 13 to 15,
$L^{11}$ to $L^{14}$ on each appearance, in each case independently of one another, denote H, alkyl having 5 to 15 C atoms, particularly preferably having 6 to 12 C atoms, F or Cl, and i denotes an integer in the range from 6 to 15, preferably from 6 or 8 to 12 and particularly preferably from 6 or 9 to 10, and preferably at least four, particularly preferably at least six, of the substituents $L^{11}$ to $L^{14}$ present denote alkyl.

Component A preferably has a dielectric anisotropy in the range from more than −5.0 and less than 10.0 and consists of compounds having eight or more five- six- or seven-membered rings.

Particular preference is given to the compounds of the formula I which have a liquid-crystal phase.

In a preferred embodiment of the present invention, component A comprises one or more compounds of the formula I, preferably selected from the group of the compounds of the of the formulae IA and IB

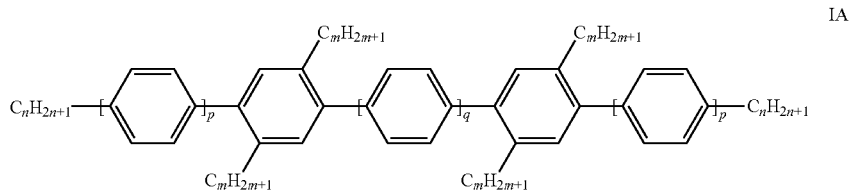

IA

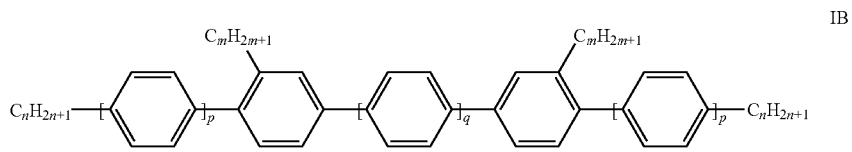

IB in which
n and m, independently of one another, denote an integer from 1 to 15, preferably 3 to 12,
p denotes an integer from 1 to 4, preferably 2,
q denotes an integer from 1 to 6, preferably 1 or 4, and
(p+q) denotes an integer from 4 to 12, preferably 4, 6 or 8.

In a preferred embodiment of the present invention, component A comprises one or more compounds of the formula IA selected from the group of the compounds of the formulae IA-1 to IA-3

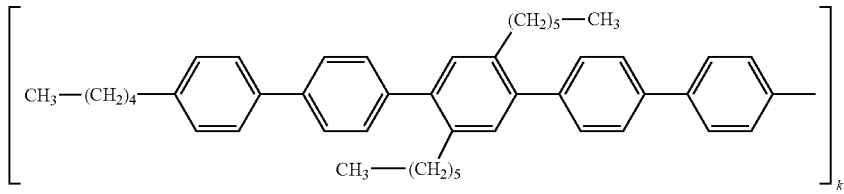

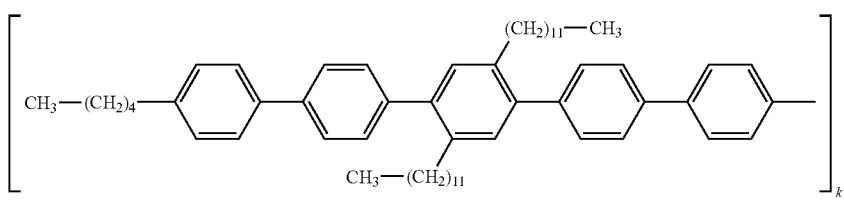

IA-2

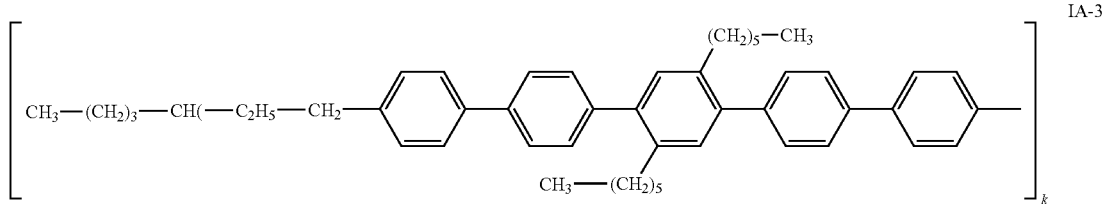

in which
k denotes 2.

In a preferred embodiment of the present invention, component A comprises one or more compounds of the formula IB selected from the group of the compounds of the formulae IB-1 and IB-2

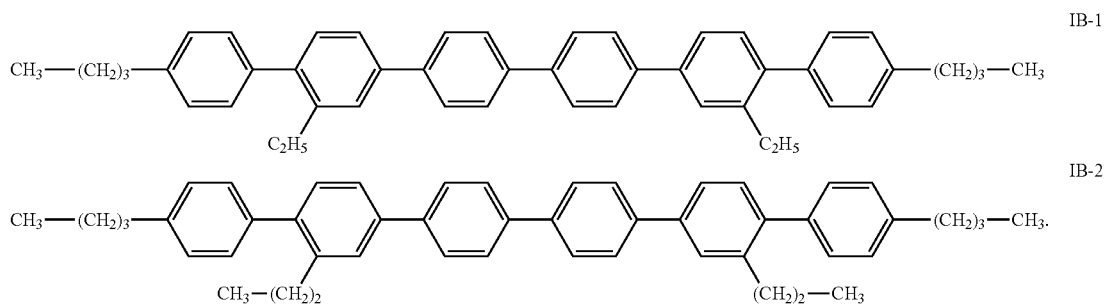

In a further preferred embodiment of the present invention, the device for high-frequency technology contains a liquid-crystalline medium which, in addition to component A, comprises at least one further component, component B, which likewise preferably has a dielectric anisotropy in the range from more than −5.0 and less than 10.0 and consists of one or more compounds of the formula IV

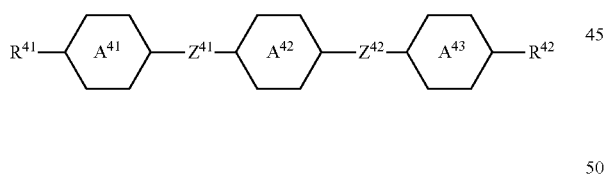

in which
one or more of

to

denote(s)

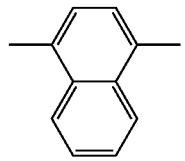

or

and the others denote

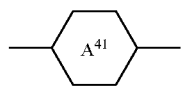

and preferably

and

both denote

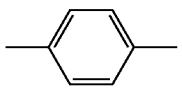

and

denotes

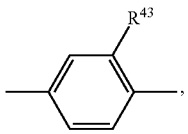

$R^{41}$ to $R^{43}$, independently of one another, have one of the meanings given for $R^{11}$, preferably unfluorinated alkyl or unfluorinated alkoxy, each having 1 to 15 C atoms, or unfluorinated alkenyl, unfluorinated alkenyloxy or unfluorinated alkoxyalkyl, each having 2 to 15 C atoms, preferably $R^{41}$ and $R^{42}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably $R^{41}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably $R^{42}$ denotes unfluorinated alkyl or unfluorinated alkoxy, each having 1 to 7 C atoms, and preferably $R^{43}$ denotes unfluorinated alkyl having 1 to 5 C atoms, unfluorinated cyclohexyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, preferably n-alkyl, particularly preferably methyl, ethyl or n-propyl, $Z^{41}$ and $Z^{42}$, independently of one another, denote —C≡C—, —CF=CF—, —CF=CH—, —CH=CF or —CH=CH—, preferably —C≡C— or —CF=CF—, preferably $Z^{41}$ and $Z^{42}$ both denote —C≡C—.

According to a further preferred embodiment of the present invention, the device for high-frequency technology contains a liquid-crystalline medium comprising a first component, component A, which consists of one or more compounds of the formula I given above, and one or more further components selected from the group of components B to E defined below, component B, which preferably has a dielectric anisotropy in the range from more than −5.0 to less than 10.0 and preferably consists of compounds of the formula IV given above, a strongly dielectrically positive component, component C, which has a dielectric anisotropy of 10.0 or more, a strongly dielectrically negative component, component D, which has a dielectric anisotropy of −5.0 or less, a further component, component E, which likewise has a dielectric anisotropy in the range from more than −5.0 to less than 10.0 and consists of compounds having up to five-, six- or seven-membered rings.

Typical examples of five-membered rings are

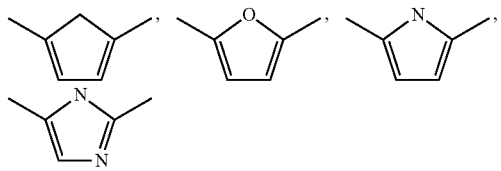

and others.

Typical examples of six-membered rings are

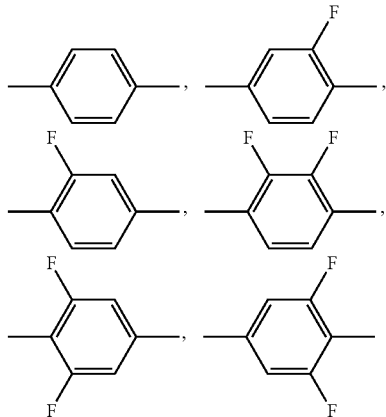

and

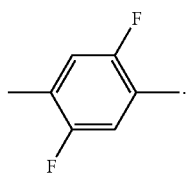

Typical examples of seven-membered rings are

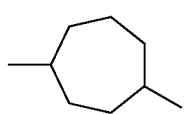

and

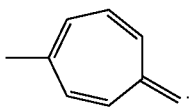

The five-, six- and seven-membered rings also include saturated and partially saturated rings, as well as heterocyclic rings.

For the purposes of the present application, condensed ring systems which consist of two of these rings, i.e., for example, two five-membered rings, one five-membered ring and one six-membered ring, five-membered ring and one seven-membered ring or two six-membered rings, such as, for example,

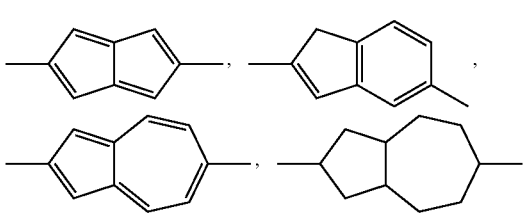

and

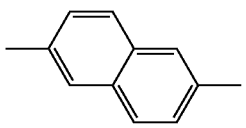

are counted as one of these five- or six- or seven-membered rings on assignment of the compounds to components A or E.

Correspondingly, condensed ring systems which consist of a combination of three or more of these rings which are incorporated into the molecule in the longitudinal direction, such as, for example,

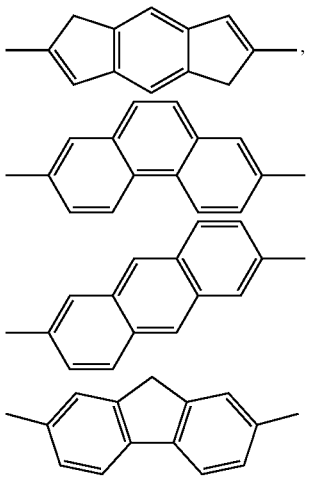

and

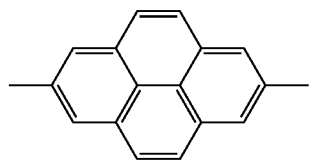

are counted as two of these five-, six- or seven-membered rings.

By contrast, condensed ring systems which are incorporated into the molecule in the transverse direction, such as, for example,

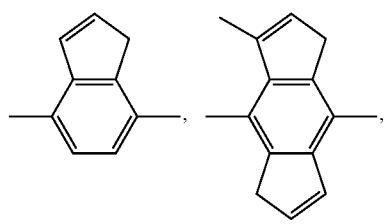

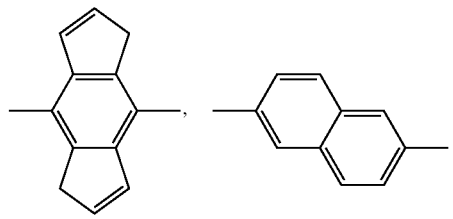

(see above),

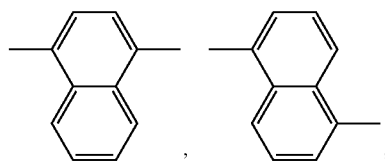

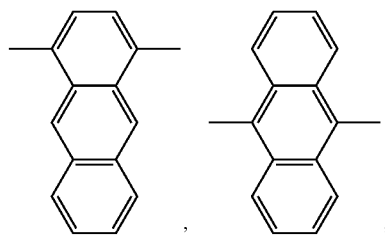

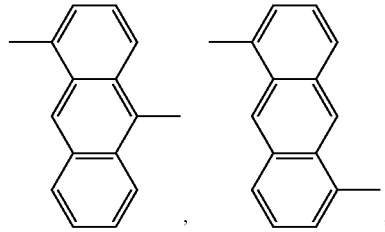

-continued

[Structures of phenanthrene and fluorene derivatives shown]

, and

[Fluorene derivative structure shown]

are counted as one of these five- or six-membered rings.

The present invention likewise relates to the directly preceding liquid-crystalline media and to those described below, and to the use thereof in electro-optical displays and in devices for high-frequency technology.

In a preferred embodiment of the present invention, the liquid-crystal medium comprises one or more compounds of the formulae IV, preferably of the formula IVA

IVA $$R^{41}\text{-}\bigcirc\text{-}C\equiv C\text{-}\bigcirc(R^{43})\text{-}C\equiv C\text{-}\bigcirc\text{-}R^{42}$$

in which the parameters have the meanings given above.

The compounds of the formula IVA are particularly preferably selected from the group of the compounds of the formulae IVA-1 to IVA-3, preferably of the formulae IVA-1 and/or IVA-2 and/or IVA-3, preferably of the formulae IVA-1 and IVA-2, these compounds more preferably predominantly consist thereof, even more preferably essentially consist thereof and very particularly preferably completely consist thereof:

IVA-1

$$R^{41}\text{-}\bigcirc\text{-}C\equiv C\text{-}\bigcirc(CH_3)\text{-}C\equiv C\text{-}\bigcirc\text{-}R^{42}$$

IVA-2

$$R^{41}\text{-}\bigcirc\text{-}C\equiv C\text{-}\bigcirc(C_2H_5)\text{-}C\equiv C\text{-}\bigcirc\text{-}R^{42}$$

IVA-3

$$R^{41}\text{-}\bigcirc\text{-}C\equiv C\text{-}\bigcirc(A^4)\text{-}C\equiv C\text{-}\bigcirc\text{-}R^{42}$$

in which $A^4$ denotes cycloalkyl having 3 to 6 C atoms, preferably cyclopropyl, cyclobutyl or cyclohexyl, particularly preferably cyclopropyl or cyclohexyl and very particularly preferably cyclopropyl, and the other parameters have the respective meanings indicated above for formula I and preferably $R^{41}$ denotes unfluorinated alkyl having 1 to 7 C atoms, and $R^{42}$ denotes unfluorinated alkyl having 1 to 7 C atoms or unfluorinated alkoxy having 1 to 7 C atoms.

These media according to the invention preferably comprise one component C and no component D or vice versa.

Besides component A, these media according to the invention preferably comprise a component selected from the two components C and D and optionally additionally component B and/or component E.

These media according to the invention preferably comprise two, three or four, particularly preferably two or three, components selected from the group of components A to E. These media preferably comprise component A and component B, or component A and component C, or component A, component B and component C, or component A, component B and/or component C and component E, or component A and component D, or component A, component B and component D, or component A, component B and/or component D and component E.

The strongly dielectrically positive component, component C, preferably has a dielectric anisotropy of 20.0 or more, more preferably 25.0 or more, particularly preferably 30.0 or more and very particularly preferably 40.0 or more.

The strongly dielectrically negative component, component D, preferably has a dielectric anisotropy of −7.0 or less, more preferably −8.0 or less, particularly preferably −10.0 or less and very particularly preferably −15.0 or less.

In a preferred embodiment of the present invention, component C comprises one or more compounds selected from the group of the compounds of the formulae IIA to IID:

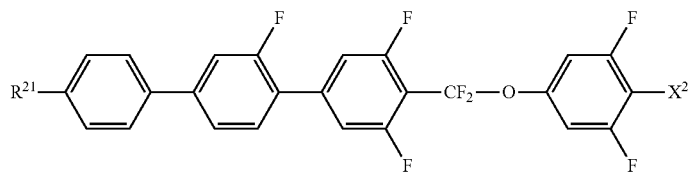   IIA

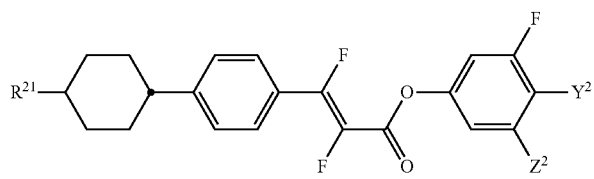   IIB

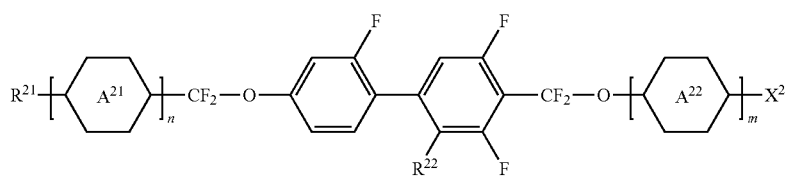   IIC

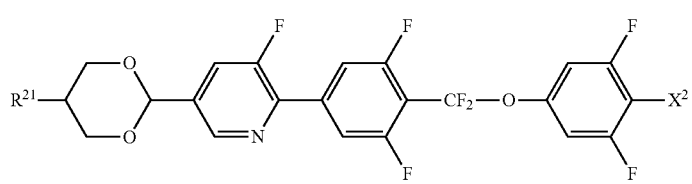   IID $R^{21}$ denotes unfluorinated alkyl or unfluorinated alkoxy, each having 1 to 15 C atoms, or unfluorinated alkenyl, unfluorinated alkenyloxy or unfluorinated alkoxyalkyl, each having 2 to 15 C atoms, preferably alkyl, particularly preferably n-alkyl, $R^{22}$ denotes H, unfluorinated alkyl or unfluorinated alkoxy, each having 1 to 5, preferably 1 to 3, particularly preferably 3, C atoms,

to

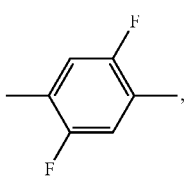, independently of one another and, if they occur more than once, these also in each case independently of one another, denote

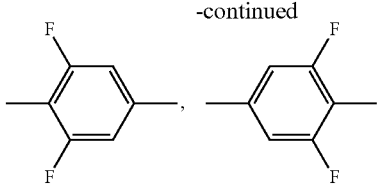

-continued

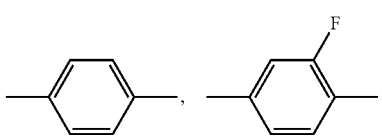

or preferably

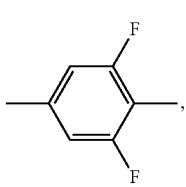

or n and m, independently of one another, denote 1 or 2, preferably
(n+m) denotes 3 or 4, and particularly preferably
n denotes 2,
$X^2$ denotes F, Cl, —$CF_3$ or —$OCF_3$, preferably F or Cl, particularly preferably F,
$Y^2$ denotes F, Cl, —$CF_3$, —$OCF_3$ or CN, preferably CN, and
$Z^2$ denotes H or F.

Preferred compounds of the formula IIA are the compounds of the corresponding sub-formula IIA-1

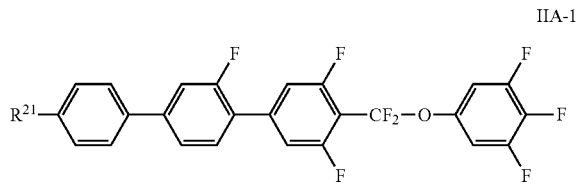

IIA-1 in which $R^{21}$ has the meaning given above.

Preferred compounds of the formula IIB are the compounds of the corresponding sub-formulae IIB-1 and IIB-2:

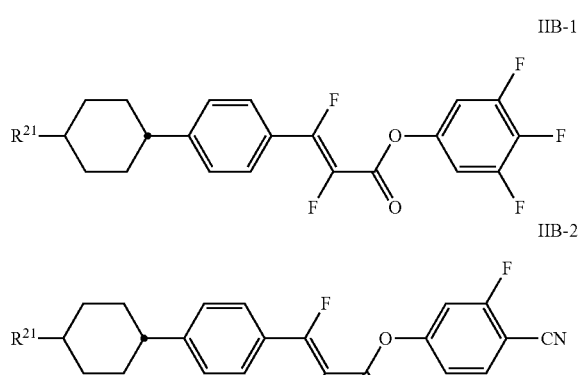

IIB-1

IIB-2 in which $R^{21}$ has the meaning given above.

Preferred compounds of the formula IIC are the compounds of the corresponding sub-formulae IIC-1 and IIC-2:

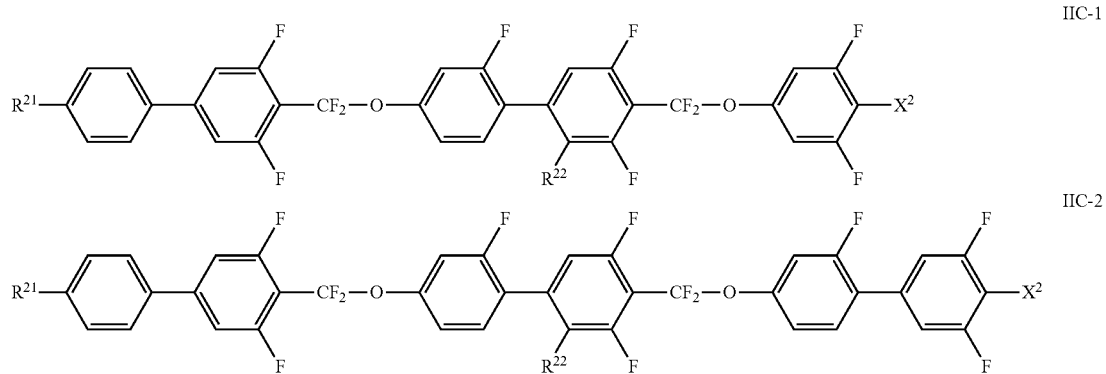

IIC-1

IIC-2 in which $R^{21}$, $R^{22}$ and $X^2$ have the respective meanings given above.

Preferred compounds of the formula IID are the compounds of the corresponding sub-formula IID-1

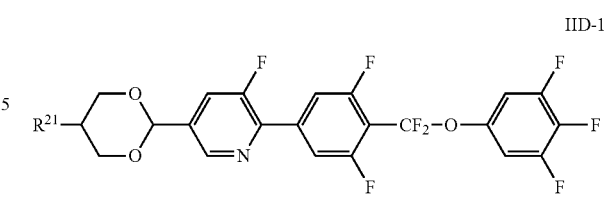

IID-1 in which $R^{21}$ has the respective meaning given above.

In a preferred embodiment of the present invention, component D comprises one or more compounds selected from the group of the compounds of the formulae IIIA and IIIB:

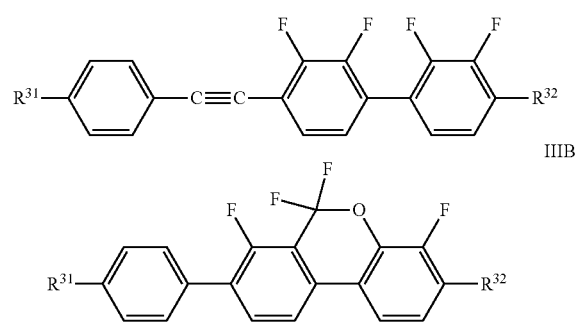

IIIA

IIIB in which
$R^{31}$ and $R^{32}$, independently of one another, have the meanings indicated above for $R^{21}$ under formula IIA,
and preferably
$R_{31}$ denotes $C_nH_{2n+1}$ or $CH_2$=CH—$(CH_2)_z$ and
$R_{32}$ denotes $C_mH_{2m+1}$ or O—$C_mH_{2m+1}$ or $(CH_2)_z$—CH=$CH_2$,
and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{31}$ and $R^{32}$) here are, in particular, ($C_nH_{2n+1}$ and $C_mH_{2m+1}$) and ($C_nH_{2n+1}$ and O—$C_mH_{2m+1}$).

Preferred compounds of the formula IIIB are the compounds of the sub-formulae IIIB-1 and IIIB-2:

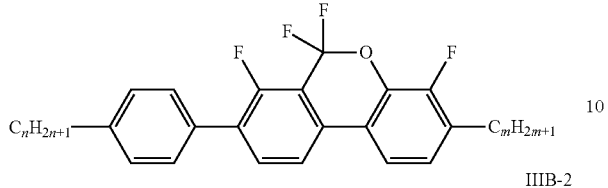
IIIB-1

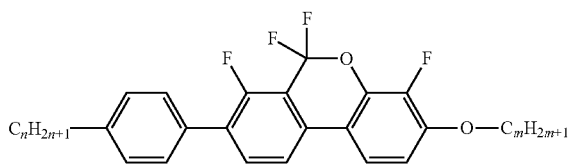
IIIB-2 in which
n and m each have the meanings given above for formula IIIB and preferably, independently of one another, denote an integer in the range from 1 to 7.

In a preferred embodiment of the present application, the liquid-crystal medium additionally comprises a further component, component E, which preferably consists of one or more compounds selected from the group of the compounds of the formulae V to IX:

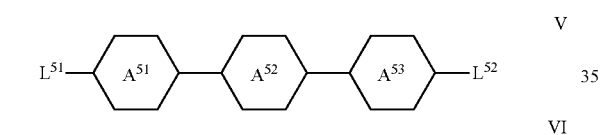
V

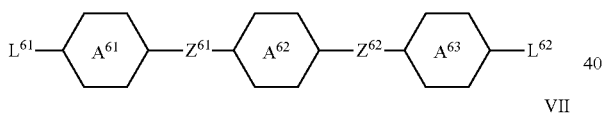
VI

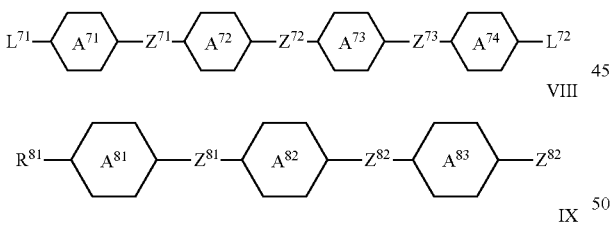
VII

VIII

IX in which
$L^{51}$ denotes $R^{51}$ or $X^{51}$,
$L^{52}$ denotes $R^{52}$ or $X^{52}$,
$R^{51}$ and $R^{52}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl,
$X^{51}$ and $X^{52}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and

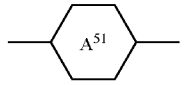

to

independently of one another, denote

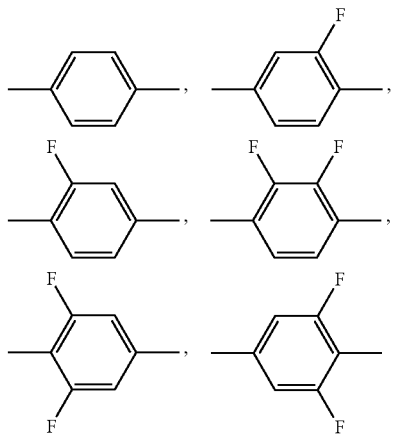

or

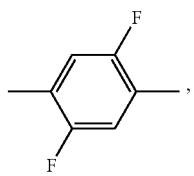

preferably

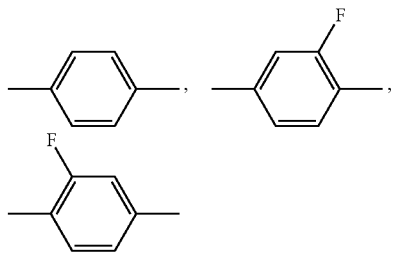

or

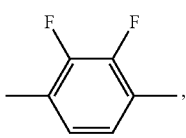

$L^{61}$ denotes $R^{61}$ and, in the case where $Z^{61}$ and/or $Z^{62}$ denote trans-CH=CH— or trans-CF=CF—, alternatively denotes $X^{61}$, $L^{62}$ denotes $R^{62}$ and, in the case where $Z^{61}$ and/or $Z^{62}$ denote trans-CH=CH— or trans-CF=CF—, alternatively denotes $X^{62}$, $R^{61}$ and $R^{62}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{61}$ and $X^{62}$, independently of one another, denote F or Cl, —CN, —NCS, —SF$_5$, fluorinated alkyl or alkoxy having 1 to 7 C atoms or fluorinated alkenyl, alkenyloxy or alkoxyalkyl having 2 to 7 C atoms, preferably —NCS, one of $Z^{61}$ and $Z^{62}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes

to

independently of one another, denote

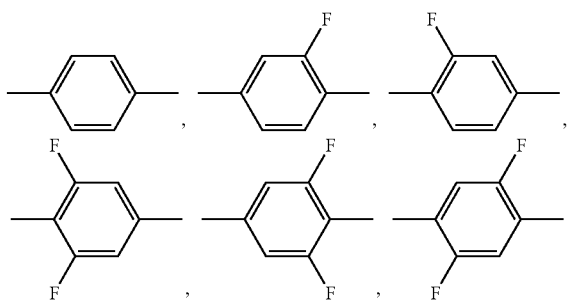

or

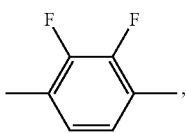

preferably

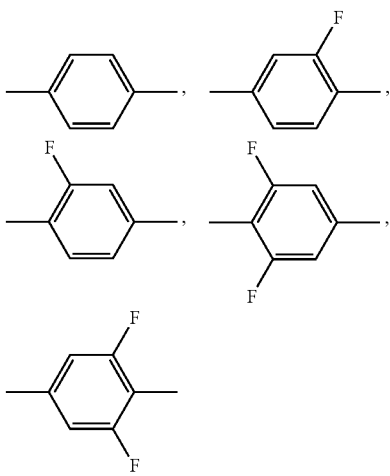

or

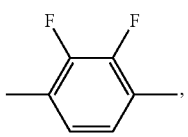

$L^{71}$ denotes $R^{71}$ or $X^{71}$, $L^{72}$ denotes $R^{72}$ or $X^{72}$, $R^{71}$ and $R^{72}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{71}$ and $X^{72}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{71}$ to $Z^{73}$, independently of one another, denote trans-CH=CH—, trans-CF=CF—, —C≡C— or a single bond, preferably one or more of them denote a single bond, particularly preferably all denote a single bond, and

to

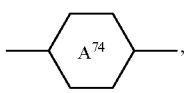

independently of one another, denote

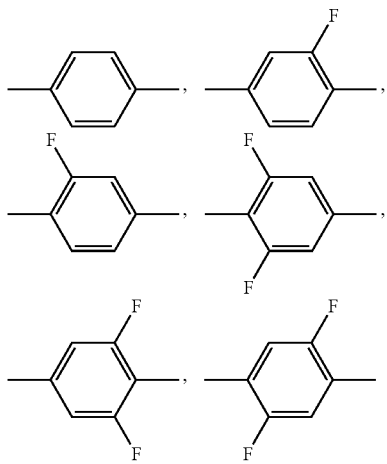

or

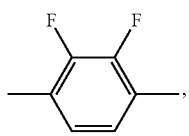

preferably

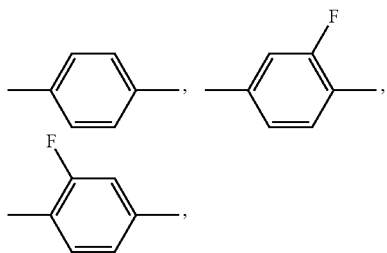

or

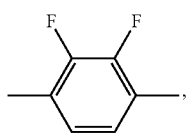

$R^{81}$ and $R^{82}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl, one of $Z^{81}$ and $Z^{82}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

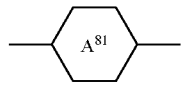

denotes

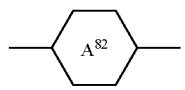

and

independently of one another, denote

or

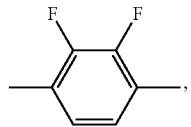

$L^{91}$ denotes $R^{91}$ or $X^{91}$,
$L^{92}$ denotes $R^{92}$ or $X^{92}$,
$R^{91}$ and $R^{92}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl,
$X^{91}$ and $X^{92}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{91}$ to $Z^{93}$, independently of one another, denote trans-CH=CH—, trans-CF=CF—, —C≡C— or a single bond, preferably one or more of them denotes a single bond, and particularly preferably all denote a single bond,

denotes

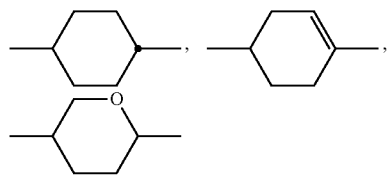

or

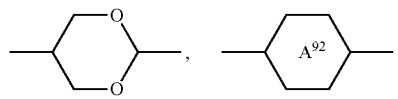

to

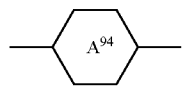

independently of one another, denote

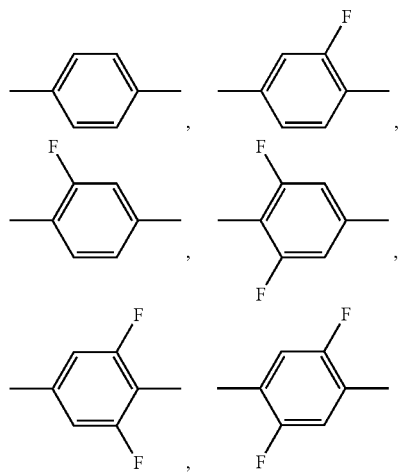

or

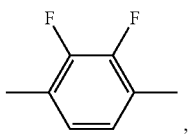

and where compounds of the formula IIIA are excluded from the compounds of the formula VI.

In a preferred embodiment of the present invention, the liquid-crystal medium comprises, more preferably predominantly consists of, even more preferably essentially consists of and very particularly preferably completely consists of one or more compounds of the formulae V, preferably selected from the group of the compounds of the formulae V-1 to V-3, preferably of the formulae V-1 and/or V-2 and/or V-3, preferably of the formulae V-1 and V-2:

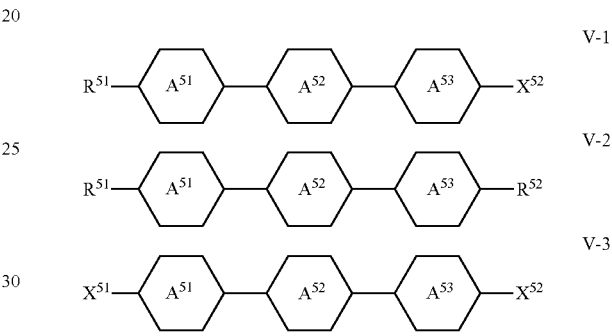

in which the parameters have the respective meanings indicated above for formula V and preferably $R^{51}$ denotes unfluorinated alkyl having 1 to 7 C atoms or unfluorinated alkenyl having 2 to 7 C atoms, $R^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —OCF$_3$, —CF$_3$, —CN, —NCS or —SF$_5$, preferably F, Cl, —OCF$_3$ or —CN.

The compounds of the formulae V-1 are preferably selected from the group of the compounds of the formulae V-1a to V-1d, more preferably these compounds of the formula V predominantly consist, even more preferably essentially consist and very particularly preferably completely consist thereof:

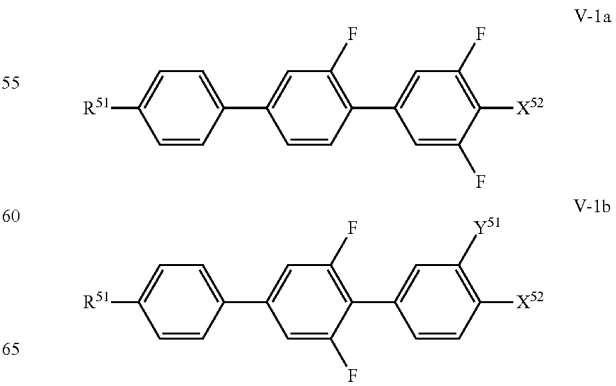

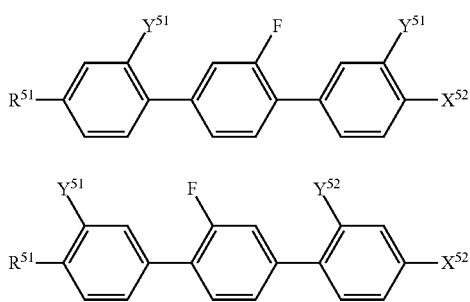

V-1c

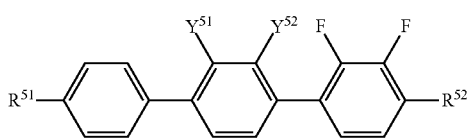

V-2g

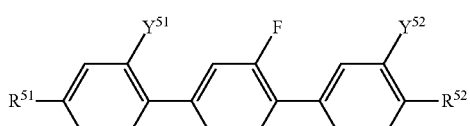

V-1d where in each case the compounds of the formula V-2a are excluded from the compounds of the formulae V-2b and V-2c, the compounds of the formula V-2b are excluded from the compounds of the formula V-2c and the compounds of the formula V-2e are excluded from the compounds of the formula V-2f, and in which the parameters have the respective meanings indicated above for formula V-1 and in which $Y^{51}$ and $Y^{52}$, in each case independently of one another, denote H or F, and preferably $R^{51}$ denotes alkyl or alkenyl, and $X^{51}$ denotes F, Cl or —OCF$_3$.

in which the parameters have the respective meanings indicated above for formula V-1 and in which $Y^{51}$ and $Y^{52}$, in each case independently of one another, denote H or F, and preferably $R^{51}$ denotes alkyl or alkenyl, $R^{52}$ denotes alkyl, alkenyl or alkoxy, preferably alkyl or alkenyl, and preferably one of $Y^{51}$ and $Y^{52}$ denotes H and the other denotes H or F, preferably likewise denotes H.

The compounds of the formulae V-2 are preferably selected from the group of the compounds of the formulae V-2a to V-2e and/or from the group of the compounds of the formulae V-2f and V-2g, more preferably these compounds of the formula V predominantly consist, even more preferably essentially consist and very particularly preferably completely consist thereof:

The compounds of the formula V-3 are preferably compounds of the formula V-3a:

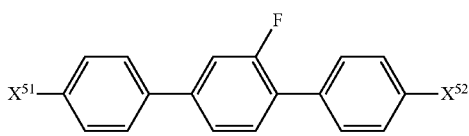

V-3a

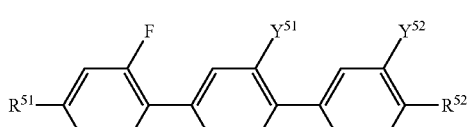

V-2a

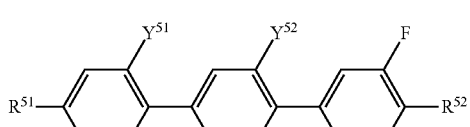

V-2b in which the parameters have the respective meanings indicated above for formula V-1 and in which preferably $X^{51}$ denotes F, Cl, preferably F, $X^{52}$ denotes F, Cl or —OCF$_3$, preferably —OCF$_3$.

In an even more preferred embodiment of the present invention, the compounds of the formula V are selected from the group of the compounds V-1a to V-1d, preferably selected from the group of the compounds V-1c and V-1d, more preferably these compounds of the formula V predominantly consist, even more preferably essentially consist and very particularly preferably completely consist thereof:

The compounds of the formulae V-1a are preferably selected from the group of the compounds of the formulae V-1a-1 and V-1a-2, more preferably these compounds of the formula V predominantly consist, even more preferably essentially consist and very particularly preferably completely consist thereof:

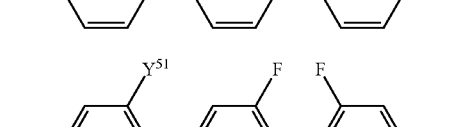

V-2c

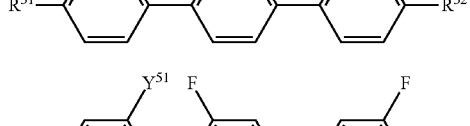

V-2d

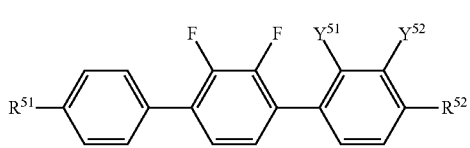

V-2e

V-2f

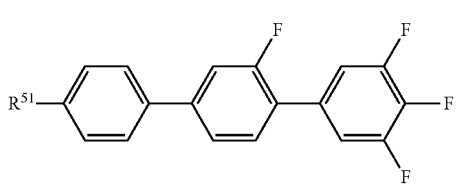

V-1a-1

V-1a-2

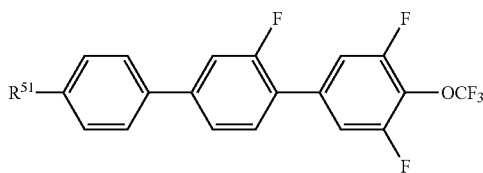

in which
R$^{51}$ has the meaning indicated above and preferably denotes C$_n$H$_{2n+1}$, in which
n denotes an integer in the range from 0 to 7, preferably in the range from 1 to 5 and particularly preferably 3 or 7.

The compounds of the formulae V-1 b are preferably compounds of the formula V-1 b-1:

V-1b-1

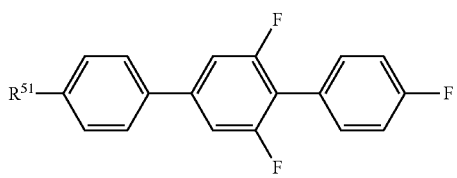

in which
R$^{51}$ has the meaning indicated above and preferably denotes C$_n$H$_{2n+1}$, in which
n denotes an integer in the range from 0 to 15, preferably in the range from 1 to 7 and particularly preferably 1 to 5.

The compounds of the formulae V-1c are preferably selected from the group of the compounds of the formulae V-1c-1 to V-1c-4, preferably selected from the group of the compounds of the formulae V-1c-1 and V-1c-2, more preferably these compounds of the formula V predominantly consist, even more preferably essentially consist and very particularly preferably completely consist thereof:

V-1c-1

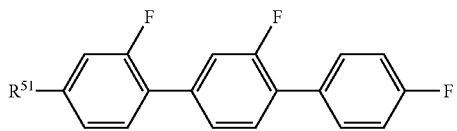

V-1c-2

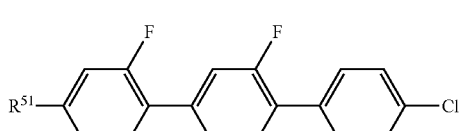

V-1c-3

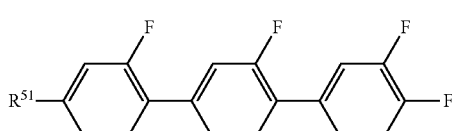

V-1c-4

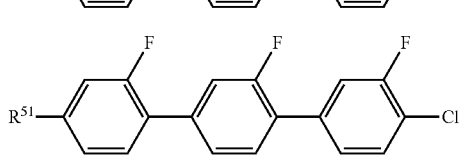

in which
R$^{51}$ has the meaning indicated above and preferably denotes C$_n$H$_{2n+1}$, in which
n denotes an integer in the range from 0 to 15, preferably in the range from 1 to 7 and particularly preferably 1 to 5.

The compounds of the formulae V-1d are preferably selected from the group of the compounds of the formulae V-1d-1 and V-1d-2, preferably the compound of the formula V-1d-2, more preferably these compounds of the formula V predominantly consist, even more preferably essentially consist and very particularly preferably completely consist thereof:

V-1d-1

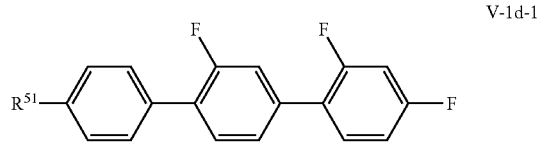

V-1d-2

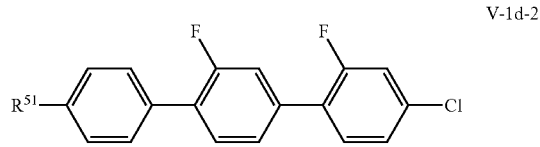

in which
R$^{51}$ has the meaning indicated above and preferably denotes C$_n$H$_{2n+1}$, in which
n denotes an integer in the range from 0 to 15, preferably in the range from 1 to 7 and particularly preferably 1 to 5.

The compounds of the formulae V-2a are preferably selected from the group of the compounds of the formulae V-2a-1 and V-2a-2, preferably the compounds of the formula V-2a-1, more preferably these compounds of the formula V predominantly consist, even more preferably essentially consist and very particularly preferably completely consist thereof:

V-2a-1

V-2a-2

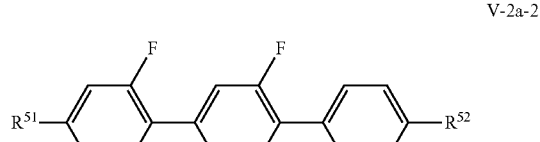

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

Preferred combinations of (R$^{51}$ and R$^{52}$), in particular in the case of formula V-2a-1, are (C$_n$H$_{2n+1}$ and C$_m$H$_{2m+1}$), (C$_n$H$_{2n+1}$ and O—C$_m$H$_{2m+1}$), (CH$_2$=CH—(CH$_2$)$_z$ and $C_mH_{2m+1}$), ($CH_2$=CH—$(CH_2)_z$ and O—$C_mH_{2m+1}$) and ($C_nH_{2n+1}$ and $(CH_2)_z$—CH=$CH_2$).

Preferred compounds of the formula V-2b are the compounds of the formula V-2b-1:

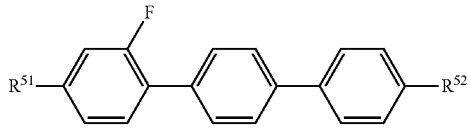

V-2b-1 in which
$R^{51}$ has the meaning indicated above and preferably denotes $C_nH_{2n+1}$ or $CH_2$=CH—$(CH_2)_z$, and
$R^{52}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of ($R^{51}$ and $R^{52}$) here is, in particular, ($C_nH_{2n+1}$ and $C_mH_{2m+1}$).

Preferred compounds of the formula V-2c are the compounds of the formula V-2c-1:

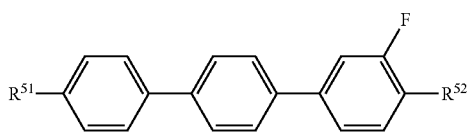

V-2c-1 in which
$R^{51}$ has the meaning indicated above and preferably denotes $C_nH_{2n+1}$ or $CH_2$=CH—$(CH_2)_z$, and
$R^{52}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of ($R^{51}$ and $R^{52}$) here is, in particular, ($C_nH_{2n+1}$ and $C_mH_{2m+1}$).

Preferred compounds of the formula V-2d are the compounds of the formula V-2d-1:

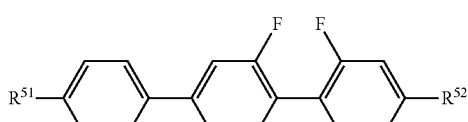

V-2d-1 in which
$R^{51}$ has the meaning indicated above and preferably denotes $C_nH_{2n+1}$ or $CH_2$=CH—$(CH_2)_z$, and
$R^{52}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of ($R^{51}$ and $R^{52}$) here is, in particular, ($C_nH_{2n+1}$ and $C_mH_{2m+1}$).

Preferred compounds of the formula V-2e are the compounds of the formula V-2e-1:

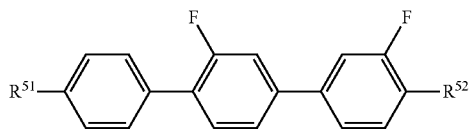

V-2e-1 in which
$R^{51}$ has the meaning indicated above and preferably denotes $C_nH_{2n+1}$ or $CH_2$=CH—$(CH_2)_z$, and
$R^{52}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of ($R^{51}$ and $R^{52}$) here is, in particular, ($C_nH_{2n+1}$ and O—$C_mH_{2m+1}$).

Preferred compounds of the formula V-2f are the compounds of the formula V-2f-1:

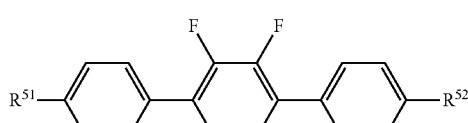

V-2f-1 in which
$R^{51}$ has the meaning indicated above and preferably denotes $C_nH_{2n+1}$ or $CH_2$=CH—$(CH_2)_z$, and
$R^{52}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{51}$ and $R^{52}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

Preferred compounds of the formula V-2g are the compounds of the formula V-2g-1:

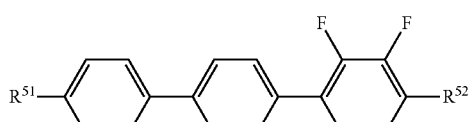

V-2g-1 in which
$R^{51}$ has the meaning indicated above and preferably denotes $C_nH_{2n+1}$ or $CH_2=CH-(CH_2)_z$, and
$R^{52}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{51}$ and $R^{52}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $O-C_mH_{2m+1}$).

The compounds of the formulae VI are preferably selected from the group of the compounds of the formulae VI-1 to VI-4, more preferably these compounds of the formula VI predominantly consist, even more preferably essentially consist and very particularly preferably completely consist thereof:

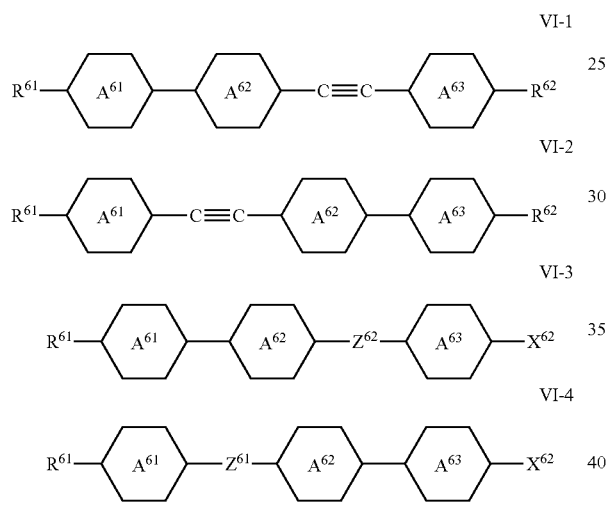

VI-1

VI-2

VI-3

VI-4 in which
$Z^{61}$ and $Z^{62}$ denote trans-CH=CH— or trans-CF=CF—, preferably trans-CH=CH—, and the other parameters have the meaning given above under formula VI and preferably
$R^{61}$ and $R^{62}$, independently of one another, denote H, unfluorinated alkyl or alkoxy having 1 to 7 C atoms or unfluorinated alkenyl having 2 to 7 C atoms,
$X^{62}$ denotes F, Cl, —CN or —NCS, preferably —NCS, and one of

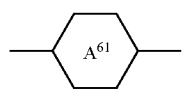

to

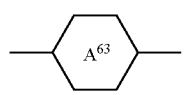

denotes

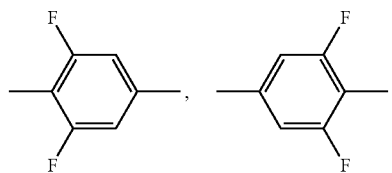

or

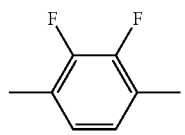

and the others, independently of one another, denote

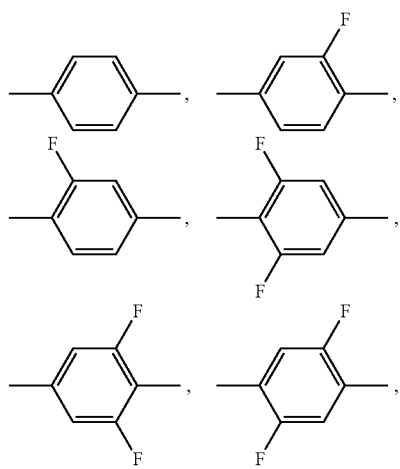

or

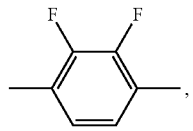

preferably

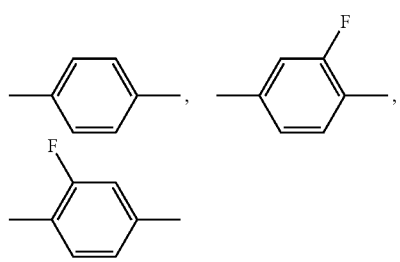

or

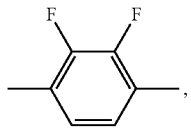

and preferably $R^{61}$ denotes $C_nH_{2n+1}$ or $CH_2=CH-(CH_2)_z$, and $R^{62}$ denotes $C_mH_{2m+1}$ or $O-C_mH_{2m+1}$ or $(CH_2)_z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formulae VI-1 are preferably selected from the group of the compounds of the formulae VI-1a and VI-1 b, preferably selected from compounds of the formulae VI-1a, more preferably these compounds of the formula VI predominantly consist, even more preferably essentially consist and very particularly preferably completely consist thereof:

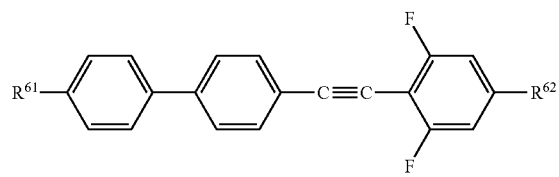

VI-1a

VI-1b in which $R^{61}$ has the meaning indicated above and preferably denotes $C_nH_{2n+1}$ or $CH_2=CH-(CH_2)_z$, and $R^{62}$ has the meaning indicated above and preferably denotes $C_mH_{2m+1}$ or $O-C_mH_{2m+1}$ or $(CH_2)_z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{61}$ and $R^{62}$) here are, in particular, ($C_nH_{2n+1}$ and $C_mH_{2m+1}$) and ($C_nH_{2n+1}$ and $O-C_mH_{2m+1}$), in the case of formula VI-1a particularly preferably ($C_nH_{2n+1}$ and $C_mH_{2m+1}$) and in the case of formula VI-1 b particularly preferably ($C_nH_{2n+1}$ and $O-C_mH_{2m+1}$).

The compounds of the formula VI-3 are preferably compounds of the formula VI-3a:

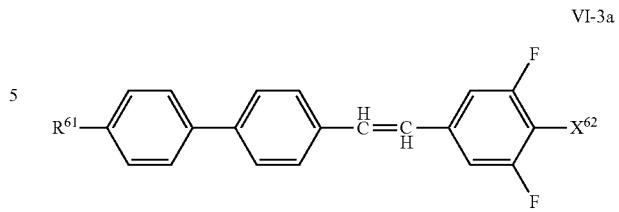

VI-3a in which the parameters have the meaning given above under formula VI-3 and preferably $R^{61}$ has the meaning indicated above and preferably denotes $C_nH_{2n+1}$, in which n denotes an integer in the range from 0 to 7, preferably in the range from 1 to 5, and $X^{62}$ denotes F, Cl, $OCF_3$, —CN or —NCS, particularly preferably —NCS.

The compounds of the formula VI-4 are preferably compounds of the formula VI-4a:

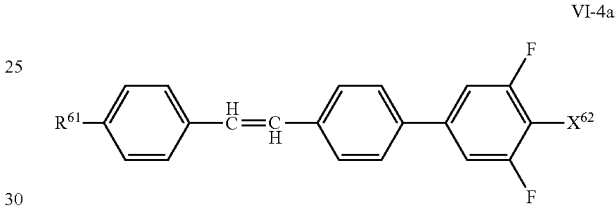

VI-4a in which the parameters have the meaning given above under formula VI-4 and preferably $R^{61}$ has the meaning indicated above and preferably denotes $C_nH_{2n+1}$, in which n denotes an integer in the range from 0 to 7, preferably in the range from 1 to 5, and $X^{62}$ denotes F, Cl, $OCF_3$, —CN or —NCS, particularly preferably —NCS.

Further preferred compounds of the formula VI are the compounds of the following formulae:

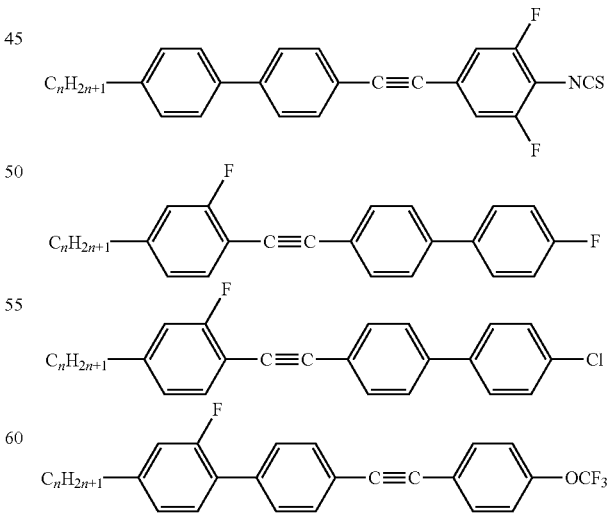

in which n denotes an integer in the range from 0 to 7, preferably in the range from 1 to 5.

The compounds of the formulae VII are preferably selected from the group of the compounds of the formulae VII-1 to VII-6, more preferably these compounds of the formula VII predominantly consist, even more preferably essentially consist and very particularly preferably completely consist thereof:

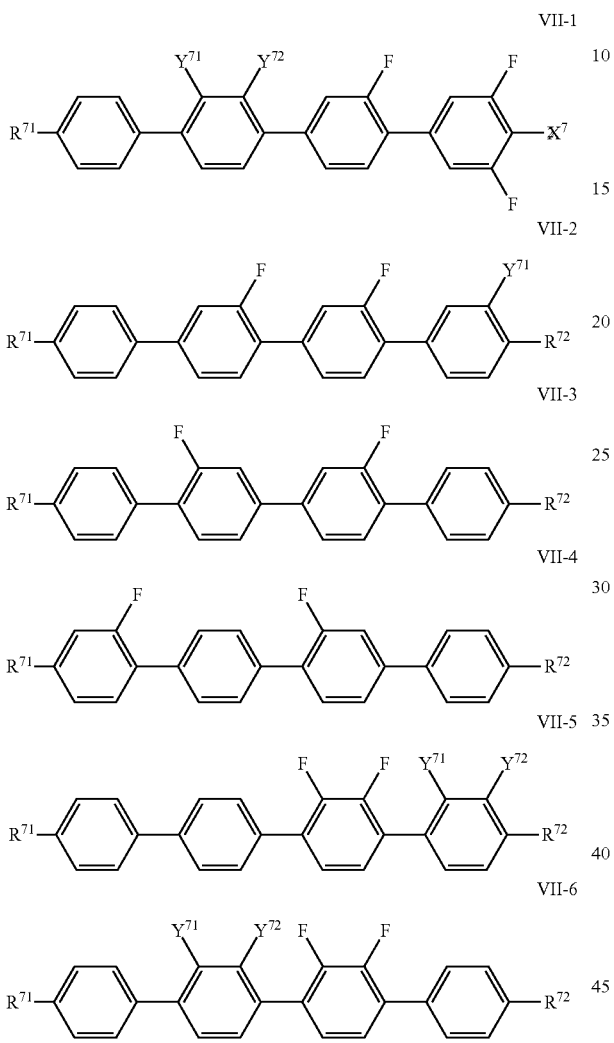

where the compounds of the formula VII-5 are excluded from the compounds of the formula VII-6, and
in which the parameters have the respective meanings indicated above for formula VII,
$Y^{71}$ and $Y^{72}$ each, independently of one another, denote H or F,
and preferably
$R^{71}$ denotes unfluorinated alkyl or alkoxy, each having 1 to 7 C atoms, or unfluorinated alkenyl having 2 to 7 C atoms,
$R^{72}$ denotes unfluorinated alkyl or alkoxy, each having 1 to 7 C atoms, or unfluorinated alkenyl having 2 to 7 C atoms, and
$X^{72}$ denotes F, Cl or —$OCF_3$, preferably F, and particularly preferably
$R^{71}$ has the meaning indicated above and preferably denotes $C_nH_{2n+1}$ or $CH_2$=CH—$(CH_2)_z$, and
$R^{72}$ has the meaning indicated above and preferably denotes $C_mH_{2m+1}$ or O—$C_mH_{2m+1}$ or $(CH_2)_z$—CH=$CH_2$, and in which n and m, independently of one another, denote an integer in the range from 0 to 15, preferably in the range from 1 to 7 and particularly preferably 1 to 5, and
z denotes 0, 1, 2, 3 or 4, preferably 0 or 2.

The compounds of the formulae VII-1 are preferably selected from the group of the compounds of the formulae VII-1a to VII-1d, more preferably these compounds of the formula VII-1 predominantly consist, even more preferably essentially consist and very particularly preferably completely consist thereof:

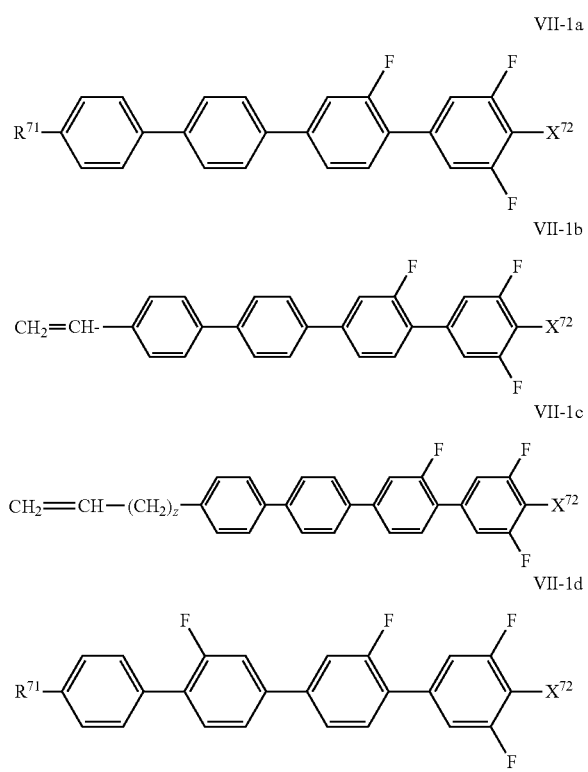

in which $X^{72}$ has the meaning given above for formula VII-2 and
$R^{71}$ has the meaning indicated above and preferably denotes $C_nH_{2n+1}$, in which
n denotes 1 to 7, preferably 2 to 6, particularly preferably 2, 3 or 5, and
z denotes 0, 1, 2, 3 or 4, preferably 0 or 2, and $X^{72}$ preferably denotes F.

The compounds of the formulae VII-2 are preferably selected from the group of the compounds of the formulae VII-2a and VII-2b, preferably of the formula VII-2a, more preferably these compounds of the formula VII-2 predominantly consist, even more preferably essentially consist and very particularly preferably completely consist thereof:

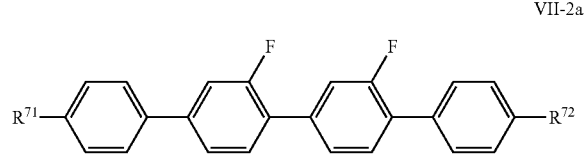

-continued

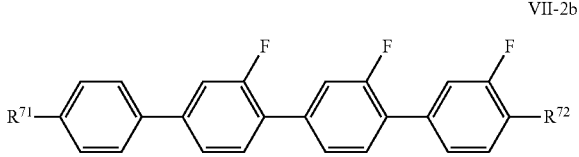

VII-2b in which
R$^{71}$ has the meaning indicated above and preferably denotes
   C$_n$H$_{2n+1}$ or CH$_2$=CH—(CH$_2$)$_z$, and
R$^{72}$ has the meaning indicated above and preferably denotes
   C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$). Particularly preferably (C$_n$H$_{2n+1}$ and C$_m$H$_{2m+1}$).

The compounds of the formula VII-3 are preferably compounds of the formula VII-3a:

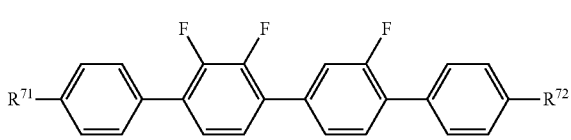

VII-3a in which
R$^{71}$ has the meaning indicated above and preferably denotes
   C$_n$H$_{2n+1}$ or CH$_2$=CH—(CH$_2$)$_z$, and
R$^{72}$ has the meaning indicated above and preferably denotes
   C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$). Particularly preferably (C$_n$H$_{2n+1}$ and C$_m$H$_{2m+1}$).

The compounds of the formula VII-4 are preferably compounds in which
R$^{71}$ has the meaning indicated above and preferably denotes
   C$_n$H$_{2n+1}$ or CH$_2$=CH—(CH$_2$)$_z$, and
R$^{72}$ has the meaning indicated above and preferably denotes
   C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formulae VII-5 are preferably selected from the group of the compounds of the formulae VII-5a and VII-5b, preferably of the formula VII-5a, more preferably these compounds of the formula VII-5 predominantly consist, even more preferably essentially consist and very particularly preferably completely consist thereof:

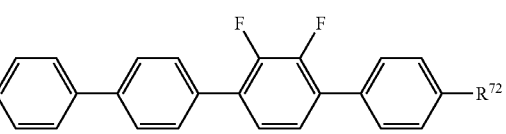

VII-5a

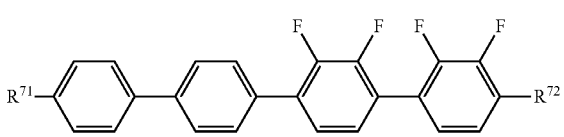

VII-5b in which
R$^{71}$ has the meaning indicated above and preferably denotes
   C$_n$H$_{2n+1}$ or CH$_2$=CH—(CH$_2$)$_z$, and
R$^{72}$ has the meaning indicated above and preferably denotes
   C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$). Particularly preferably (C$_n$H$_{2n+1}$ and C$_m$H$_{2m+1}$).

The compounds of the formulae VII-6 are preferably selected from the group of the compounds of the formulae VII-6a and VII-6b, more preferably these compounds of the formula VII-6 predominantly consist, even more preferably essentially consist and very particularly preferably completely consist thereof:

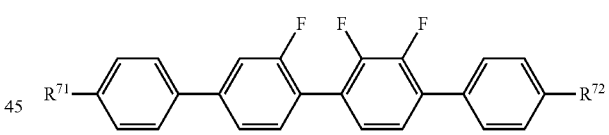

VII-6a

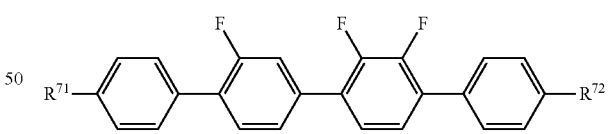

VII-6b in which
R$^{71}$ has the meaning indicated above and preferably denotes
   C$_n$H$_{2n+1}$ or CH$_2$=CH—(CH$_2$)$_z$, and
R$^{72}$ has the meaning indicated above and preferably denotes
   C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The liquid-crystalline media in accordance with the present application preferably comprise in total 0 to 40%, preferably 0 to 30% and particularly preferably 5 to 25%, of compounds of the formula VIII.

The compounds of the formulae VIII are preferably selected from the group of the compounds of the formulae VIII-1 to VIII-3, more preferably these compounds of the formula VIII predominantly consist, even more preferably essentially consist and very particularly preferably completely consist thereof:

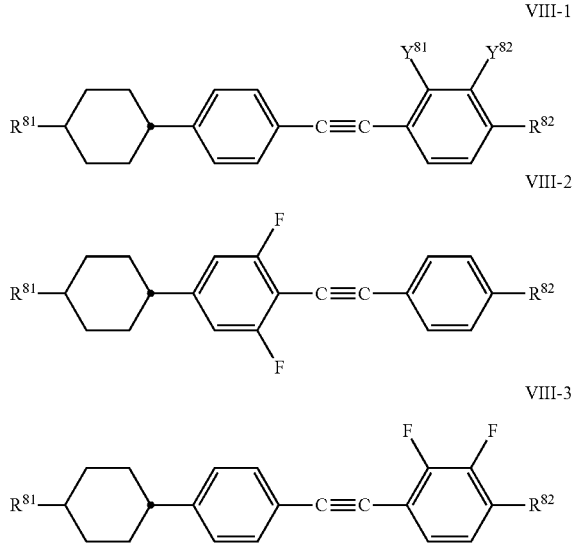

VIII-1

VIII-2

VIII-3 in which
one of
$Y^{81}$ and $Y^{82}$ denotes H and the other denotes H or F, and
$R^{81}$ has the meaning indicated above and preferably denotes $C_nH_{2n+1}$ or $CH_2=CH-(CH_2)_z$, and
$R^{82}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$) particularly preferably ($C_nH_{2n+1}$ and $C_mH_{2m+1}$).

The compounds of the formulae VIII-1 are preferably selected from the group of the compounds of the formulae VIII-1a to VIII-1c, more preferably these compounds of the formula VIII-1 predominantly consist, even more preferably essentially consist and very particularly preferably completely consist thereof:

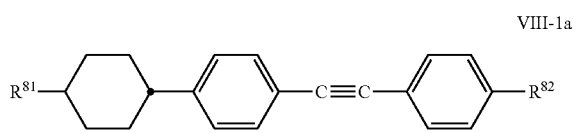

VIII-1a

-continued

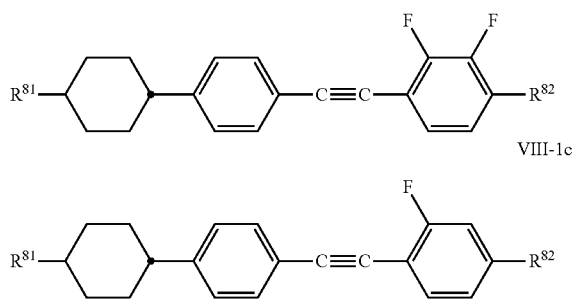

VIII-1b

VIII-1c in which
$R^{81}$ has the meaning indicated above and preferably denotes $C_nH_{2n+1}$ or $CH_2=CH-(CH_2)_z$, and
$R^{82}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$) particularly preferably ($C_nH_{2n+1}$ and $C_mH_{2m+1}$).

The compounds of the formula VIII-2 are preferably compounds in which
$R^{81}$ has the meaning indicated above and preferably denotes $C_nH_{2n+1}$ or $CH_2=CH-(CH_2)_z$, and
$R^{82}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$), ($C_nH_{2n+1}$ and $O-C_mH_{2m+1}$) and ($CH_2=CH-(CH_2)_z$ and $C_mH_{2m+1}$) particularly preferably ($C_nH_{2n+1}$ and $C_mH_{2m+1}$).

The compounds of the formula VIII-3 are preferably compounds in which
$R^{81}$ has the meaning indicated above and preferably denotes $C_nH_{2n+1}$ or $CH_2=CH-(CH_2)_z$, and
$R^{82}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$).

The compounds of the formulae IX are preferably selected from the group of the compounds of the formulae IX-1 to IX-3, more preferably these compounds of the formula IX predominantly consist, even more preferably essentially consist and very particularly preferably completely consist thereof:

IX-1

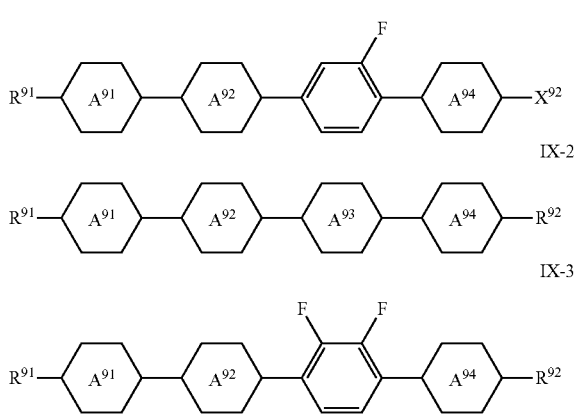

IX-2

IX-3 in which the parameters have the respective meaning indicated above under formula IX and preferably

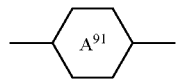

denotes

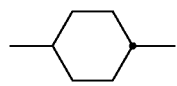

or

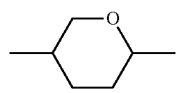

one of

to

denotes

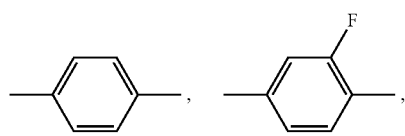

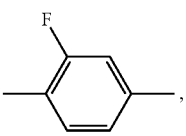

and in which $R^{91}$ has the meaning indicated above and preferably denotes $C_nH_{2n+1}$ or $CH_2$=CH—$(CH_2)_z$, and $R^{92}$ has the meaning indicated above and preferably denotes $C_mH_{2m+1}$ or O—$C_mH_{2m+1}$ or $(CH_2)_z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and O—$C_mH_{2m+1}$).

The liquid-crystalline media in accordance with the present application preferably comprise in total 5 to 30%, preferably 10 to 25% and particularly preferably 15 to 20%, of compounds of the formula IX.

The compounds of the formulae IX-1 are preferably selected from the group of the compounds of the formulae IX-1a to IX-1e, more preferably these compounds of the formula IX-1 predominantly consist, even more preferably essentially consist and very particularly preferably completely consist thereof:

IX-1a

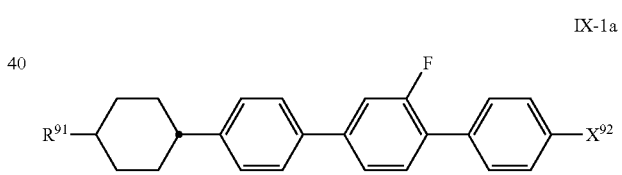

IX-1b

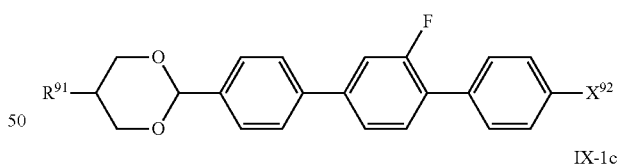

IX-1c

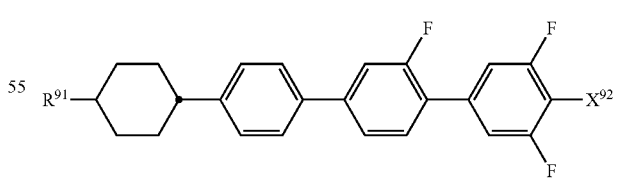

IX-1d

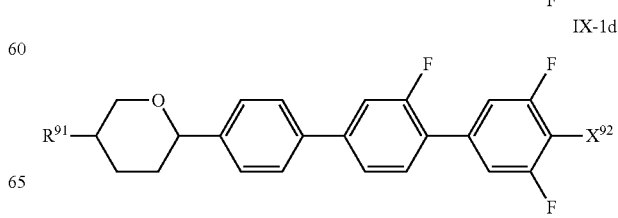

-continued

IX-1e

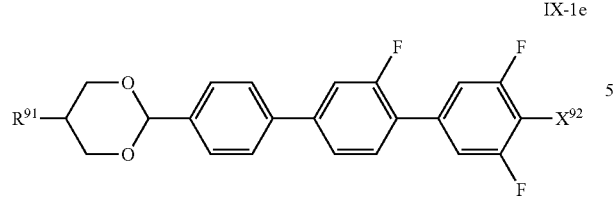

in which the parameters have the meaning given above and preferably $R^{91}$ has the meaning indicated above and preferably denotes $C_nH_{2n+1}$, and n denotes an integer in the range from 0 to 15, preferably in the range from 1 to 7 and particularly preferably 1 to 5, and $X^{92}$ preferably denotes F or Cl.

The compounds of the formulae IX-2 are preferably selected from the group of the compounds of the formulae IX-2a and IX-2b, more preferably these compounds of the formula IX-2 predominantly consist, even more preferably essentially consist and very particularly preferably completely consist thereof:

IX-2a

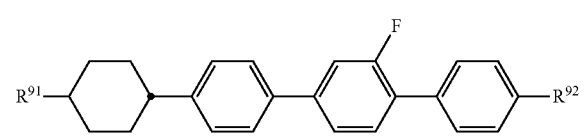

IX-2b

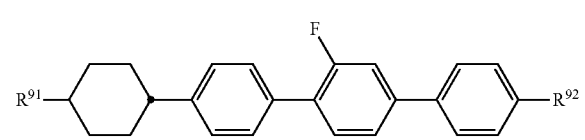

in which $R^{91}$ has the meaning indicated above and preferably denotes $C_nH_{2n+1}$ or $CH_2\!=\!CH\!-\!(CH_2)_z$, and $R^{92}$ has the meaning indicated above and preferably denotes $C_mH_{2m+1}$ or $O\!-\!C_mH_{2m+1}$ or $(CH_2)_z\!-\!CH\!=\!CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of ($R^{91}$ and $R^{92}$) here is, in particular, ($C_nH_{2n+1}$ and $C_mH_{2m+1}$).

The compounds of the formula IX-3 are preferably compounds of the formulae IX-3a and IX-3b:

IX-3a

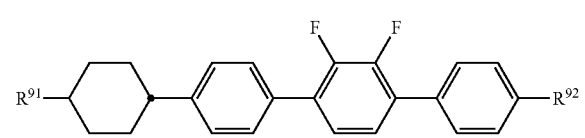

IX-3b

in which $R^{91}$ has the meaning indicated above and preferably denotes $C_nH_{2n+1}$ or $CH_2\!=\!CH\!-\!(CH_2)_z$, and $R^{92}$ has the meaning indicated above and preferably denotes $C_mH_{2m+1}$ or $O\!-\!C_mH_{2m+1}$ or $(CH_2)_z\!-\!CH\!=\!CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and $O\!-\!C_mH_{2m+1}$), particularly preferably ($C_nH_{2n+1}$ and $O\!-\!C_mH_{2m+1}$).

In a preferred embodiment of the present invention, the medium comprises one or more dielectrically positive compounds of the formula V-1 having a dielectric anisotropy of greater than 3.

The liquid-crystalline media in accordance with the present invention preferably comprise 10% or less, preferably 5% or less, particularly preferably 2% or less, very particularly preferably 1% or less, and in particular absolutely no compound having only two or fewer five- and/or six-membered rings.

In a preferred embodiment of the present invention, the medium comprises one or more compounds of the formula VI.

In a further preferred embodiment of the present invention, the medium comprises one or more compounds of the formula VII.

The definitions of the abbreviations (acronyms) are indicated below in Table D or are evident from Tables A to C.

The liquid-crystalline media in accordance with the present invention preferably comprise, more preferably predominantly consist of, even more preferably essentially consist of and very particularly preferably completely consist of compounds selected from the group of the compounds of the formulae I, II, IV and V, preferably I, II and IV, or selected from the group of the compounds of the formulae I, III, IV and V, preferably I, III and IV.

In this application, comprise in connection with compositions means that the entity in question, i.e. the medium or the component, comprises the component or components or compound or compounds indicated, preferably in a total concentration of 10% or more and very preferably 20% or more.

In this connection, predominantly consist of means that the entity in question comprises 55% or more, preferably 60% or more and very preferably 70% or more, of the component or components or compound or compounds indicated.

In this connection, essentially consist of means that the entity in question comprises 80% or more, preferably 90% or more and very preferably 95% or more, of the component or components or compound or compounds indicated.

In this connection, completely consist of means that the entity in question comprises 98% or more, preferably 99% or more and very preferably 100.0% of the component or components or compound or compounds indicated.

Other mesogenic compounds which are not explicitly mentioned above can optionally and advantageously also be used in the media in accordance with the present invention. Such compounds are known to the person skilled in the art.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The nematic phase of the media according to the invention preferably extends at least from 20° C. or less to 90° C. or more, preferably up to 100° C. or more, more preferably at least from 0° C. or less to 120° C. or more, very preferably at least from −10° C. or less to 140° C. or more and in particular at least from −20° C. or less to 150° C. or more.

The $\Delta\in$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm ($Na^D$) and 20° C., is preferably in the range from 0.200 or more to 0.90 or less, more preferably in the range from 0.250 or more to 0.90 or less, even more preferably in the range from 0.300 or more to 0.85 or less and very particularly preferably in the range from 0.350 or more to 0.800 or less.

In a preferred embodiment of the present application, the $\Delta n$ of the liquid-crystal media in accordance with the present invention is preferably 0.50 or more, more preferably 0.55 or more.

In accordance with the present invention, the individual compounds of the formula I in the liquid-crystal media are preferably used in a total concentration of 1% to 20%, more preferably 2% to 15%, even more preferably 3% to 12% and very preferably 5% to 10%, of the mixture as a whole.

In the embodiment of the present invention in which the liquid-crystal media comprise one or more compounds selected from the group of the compounds of the formulae IIA and IID, the further compounds are preferably employed as follows.

The compounds selected from the group of the compounds of the formulae IIA and IID are preferably used in a total concentration of 1% to 30%, more preferably 2% to 20%, even more preferably 3% to 18% and very preferably 4% to 16%, of the mixture as a whole.

The compounds of the formula IV are preferably used in a total concentration of 10% to 100%, more preferably 30% to 95%, even more preferably 40% to 90% and very preferably 50% to 90%, of the mixture as a whole.

The liquid-crystal media preferably comprise, more preferably predominantly consist of and very preferably completely consist of in total 70% to 100%, more preferably 80% to 100% and very preferably 90% to 100% and in particular 95% to 100%, of the compounds of the formulae I, IIA, IIB, IIC, IID and IV to IX, preferably of the formulae I, IIA, IIB, IIC, IID and IV.

In the embodiment of the present invention in which the liquid-crystal media comprise one or more compounds selected from the group of the compounds of the formulae IIIA and IIIB, the further compounds are preferably employed as follows.

The compounds selected from the group of the compounds of the formulae IIIA and IIIB are preferably used in a total concentration of 1% to 60%, more preferably 5% to 55%, even more preferably 7% to 50% and very preferably 10% to 45%, of the mixture as a whole.

If the liquid-crystal media comprise only one or more compounds of the formula IIIA, but no compounds of the formula IIIB, the compounds of the formula IIIA are preferably used in a total concentration of 10% to 60%, more preferably 20% to 55%, even more preferably 30% to 50% and very preferably 35% to 45%, of the mixture as a whole.

If the liquid-crystal media comprise only one or more compounds of the formula IIIB, but no compounds of the formula IIIA, the compounds of the formula IIIB are preferably used in a total concentration of 5% to 45%, more preferably 10% to 40%, even more preferably 15% to 35% and very preferably 20% to 30%, of the mixture as a whole.

If the liquid-crystal media comprise both one or more compounds of the formula IIIA and one or more compounds of the formula IIIB, the compounds of the formula IIIA are preferably used in a total concentration of 5% to 50%, more preferably 10% to 45%, even more preferably 15% to 30% and very preferably 20% to 25%, of the mixture as a whole and the compounds of the formula IIIB are preferably used in a total concentration of 1% to 35%, more preferably 5% to 30%, even more preferably 7% to 25% and very preferably 10% to 20%, of the mixture as a whole.

In this embodiment, the compounds of the formula I are preferably used in a total concentration of 1% to 20%, more preferably 2% to 15%, even more preferably 3% to 12% and very preferably 5% to 10%, of the mixture as a whole.

The liquid-crystal media preferably comprise, more preferably predominantly consist of and very preferably completely consist of in total 70% to 100%, more preferably 80% to 100% and very preferably 90% to 100% and in particular 95% to 100%, of the compounds of the formulae I, IIIA, IIIB and IV to IX, preferably of the formulae I, IIIA and/or IIIB and/or IV.

In a particularly preferred embodiment of the present invention, the liquid-crystalline media comprise one or more compounds of the formula V and one or more compounds of the formula VI.

In a further particularly preferred embodiment of the present invention, the liquid-crystalline media comprise one or more compounds of the formula V and one or more compounds of the formula VII.

The liquid-crystalline media in accordance with the present invention likewise preferably comprise one or more compounds of the formula V, one or more compounds of the formula VI and one or more compounds of the formula VIII.

If the liquid-crystalline media in accordance with the present application comprise one or more compounds of the formula V, the concentration of these compounds is preferably in total 10 to 30%, preferably 15 to 25% and particularly preferably 18 to 22%.

If the liquid-crystalline media in accordance with the present application comprise one or more compounds of the formula VI, the concentration of these compounds is preferably in total 15 to 35%, preferably 18 to 30% and particularly preferably 22 to 26%.

If the liquid-crystalline media in accordance with the present application comprise one or more compounds of the formula VII, the concentration of these compounds is preferably in total 4 to 25%, preferably 8 to 20% and particularly preferably 10 to 14%.

If the liquid-crystalline media in accordance with the present application comprise one or more compounds of the formula VIII, the concentration of these compounds is preferably in total 15 to 35%, preferably 18 to 30% and particularly preferably 22 to 26%.

If the liquid-crystalline media in accordance with the present application comprise one or more compounds of the formula IX, the concentration of these compounds is preferably in total 5 to 25%, preferably 10 to 20% and particularly preferably 13 to 17%.

In the present application, the expression dielectrically positive describes compounds or components where $\Delta\epsilon>3.0$, dielectrically neutral describes those where $-1.5\leq\Delta\epsilon\leq3.0$ and dielectrically negative describes those where $\Delta\epsilon<-1.5$. $\Delta\epsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

The following definitions apply here.

$$\Delta\epsilon \equiv (\epsilon_{\parallel} - \epsilon_{\perp}) \text{ and}$$

$$\epsilon_{average} \equiv (\epsilon_{\parallel} + 2\epsilon_{\perp})/3.$$

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy (Δn) is determined at a wavelength of 589.3 nm. The dielectric anisotropy (Δ∈) is determined at a frequency of 1 kHz. The threshold voltages, as well as all other electro-optical properties, are determined using test cells produced at Merck KGaA, Germany. The test cells for the determination of Δ∈ have a cell thickness of approximately 20 m. The electrode is a circular ITO electrode having an area of 1.13 cm² and a guard ring. The orientation layers are SE-1211 from Nissan Chemicals, Japan, for homeotropic orientation ($\epsilon_{\parallel}$) and polyimide AL-1054 from Japan Synthetic Rubber, Japan, for homogeneous orientation ($\epsilon_{\perp}$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency region as described in A. Penirschke, S. Müller, P. Scheele, C. Weil, M. Wittek, C. Hock and R. Jakoby: "Cavity Perturbation Method for Characterization of Liquid Crystals up to 35 GHz", 34th European Microwave Conference—Amsterdam, pp. 545-548.

Compare in this respect also A. Gaebler, F. Goelden, S. Müller, A. Penirschke and R. Jakoby "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) capillary. The capillary has an internal radius of 180 m and an external radius of 350 μm. The effective length is 2.0 cm. The filled capillary is introduced into the centre of the cavity with a resonance frequency of 30 GHz. This cavity has a length of 6.6 mm, a width of 7.1 mm and a height of 3.6 mm. The input signal (source) is then applied, and the result of the output signal is recorded using a commercial vector network analyser.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in A. Penirschke, S. Müller, P. Scheele, C. Weil, M. Wittek, C. Hock and R. Jakoby: "Cavity Perturbation Method for Characterization of Liquid Crystals up to 35 GHz", 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

Preferred devices are phase shifters, varactors, wireless and radio wave antenna arrays, matching circuit adaptive filters and others.

In the present application, the term compounds is taken to mean both one compound and a plurality of compounds, unless expressly stated otherwise.

In a preferred embodiment, the liquid-crystal media according to the invention have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 160° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a layer thickness of 5 μm for at least 100 hours. At high temperatures, the clearing point is measured in capillaries by conventional methods.

Furthermore, the liquid-crystal media according to the invention are characterised by high optical anisotropies in the visible region. The birefringence at 589 nm is preferably 0.20 or more, particularly preferably 0.25 or more, particularly preferably 0.30 or more, particularly preferably 0.40 or more and very particularly preferably 0.45 or more. In addition, the birefringence is preferably 0.80 or less.

In a preferred embodiment of the present invention, the liquid-crystal media employed have a positive dielectric anisotropy ($\Delta\epsilon$) having a value, measured at 1 kHz, of preferably 0.5 or more, more preferably 1 or more, particularly preferably 2 or more and very particularly preferably 3 or more. The dielectric anisotropy is particularly preferably between 1.8 or more and 15.0 or less, more preferably between 2.0 or more and 10.0 or less, particularly preferably between 3.0 or more and 8.0 or less and very particularly preferably between 3.5 or more and 6.0 or less.

In some embodiments, however, liquid crystals having a negative value of the dielectric anisotropy are advantageously used. In this case, the dielectric anisotropy is preferably less than or equal to −2.5, particularly preferably less than or equal to −4.0 and very particularly preferably less than or equal to −5.0. The value of $\Delta\epsilon$ in this embodiment is preferably 1.5 or more and 15.0 or less, particularly preferably 1.8 or more and 12.0 or less and very particularly preferably 2.0 or more and 10.0 or less.

Furthermore, the liquid-crystal media according to the invention are characterised by high anisotropies in the microwave region. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The dielectric anisotropy in the microwave region is defined as $\Delta\epsilon_r \equiv (\epsilon_{r,\|} - \epsilon_{r,\perp})$.

The tunability ($\tau$) is defined as $\tau \equiv (\Delta\epsilon_r / \epsilon_{r,\|})$.

The material quality ($\eta$) is defined as $\eta \equiv (\tau / \tan\delta_{\epsilon r,max})$, where the maximum dielectric loss is $\tan\delta_{\epsilon r,max} = \max\cdot\{\tan\delta_{\epsilon r,\perp}; \tan\delta_{\epsilon r,\|}\}$.

The material quality ($\eta$) of the preferred liquid-crystal materials is 4.5 or more, preferably 5 or more, preferably 6 or more, preferably 10 or more, preferably 15 or more, preferably 17 or more, more preferably 20 or more, particularly preferably 25 or more and very particularly preferably 30 or more.

In general, the material quality of the liquid-crystal media correlates with their dielectric anisotropy (for example at 1 kHz). The material quality in the case of the liquid-crystal media which have a greater dielectric anisotropy at 1 kHz ($\Delta\epsilon$) is lower than in the case of those which have a smaller dielectric anisotropy at 1 kHz ($\Delta\epsilon$). However, the liquid-crystal media which have a smaller dielectric anisotropy at 1 kHz ($\Delta\epsilon$) are more difficult to address electrically.

Preference is given in accordance with the present invention whose material quality is characterised in accordance with their dielectric anisotropies, as indicated in the following table.

| | Limits of η | | |
|---|---|---|---|
| $\Delta\epsilon$ | preferably | more preferably | particularly preferably |
| 0 to <1 | ≥40 | ≥45 | ≥50 |
| 1 to <2 | ≥35 | ≥40 | ≥45 |
| 2 to <3 | ≥30 | ≥35 | ≥40 |
| 3 to <4 | ≥25 | ≥30 | ≥35 |
| 4 to <5 | ≥20 | ≥25 | ≥30 |
| 5 to <6 | ≥15 | ≥20 | ≥25 |

In the corresponding devices, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

The liquid crystals employed are either individual substances or mixtures. They preferably have a nematic phase.

The compounds of the formula I can be obtained in accordance with the following general reaction schemes (reaction schemes I to IV).

The compounds of the formula I where i=6 or where i=10 are, for example, advantageously obtained in accordance with Reaction Schemes III or IV.

Reaction Scheme I

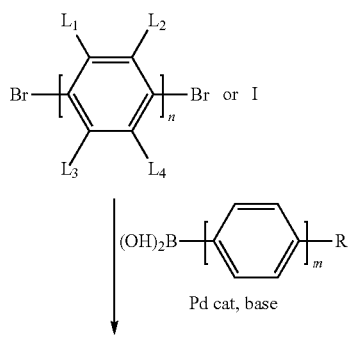

Pd cat, base

-continued
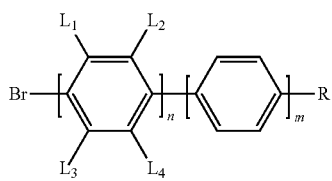
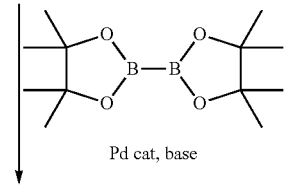
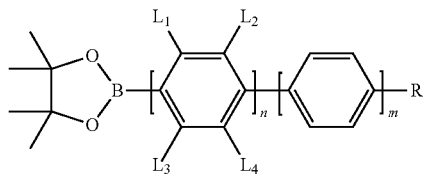
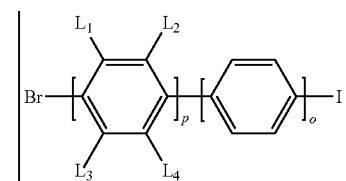
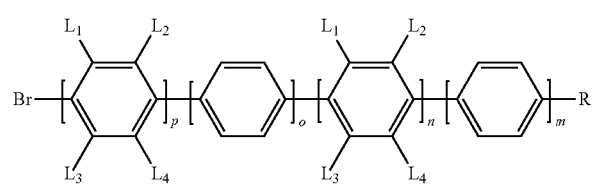
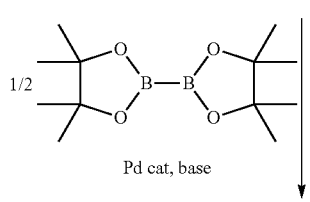
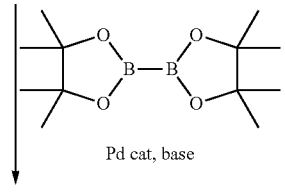
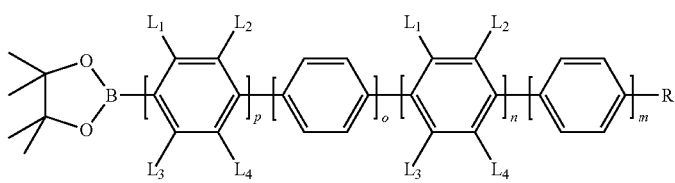
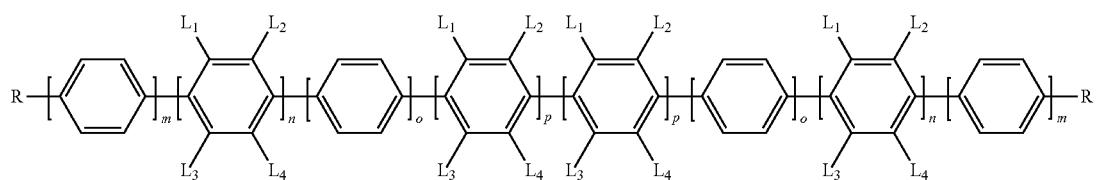

Reaction Scheme II

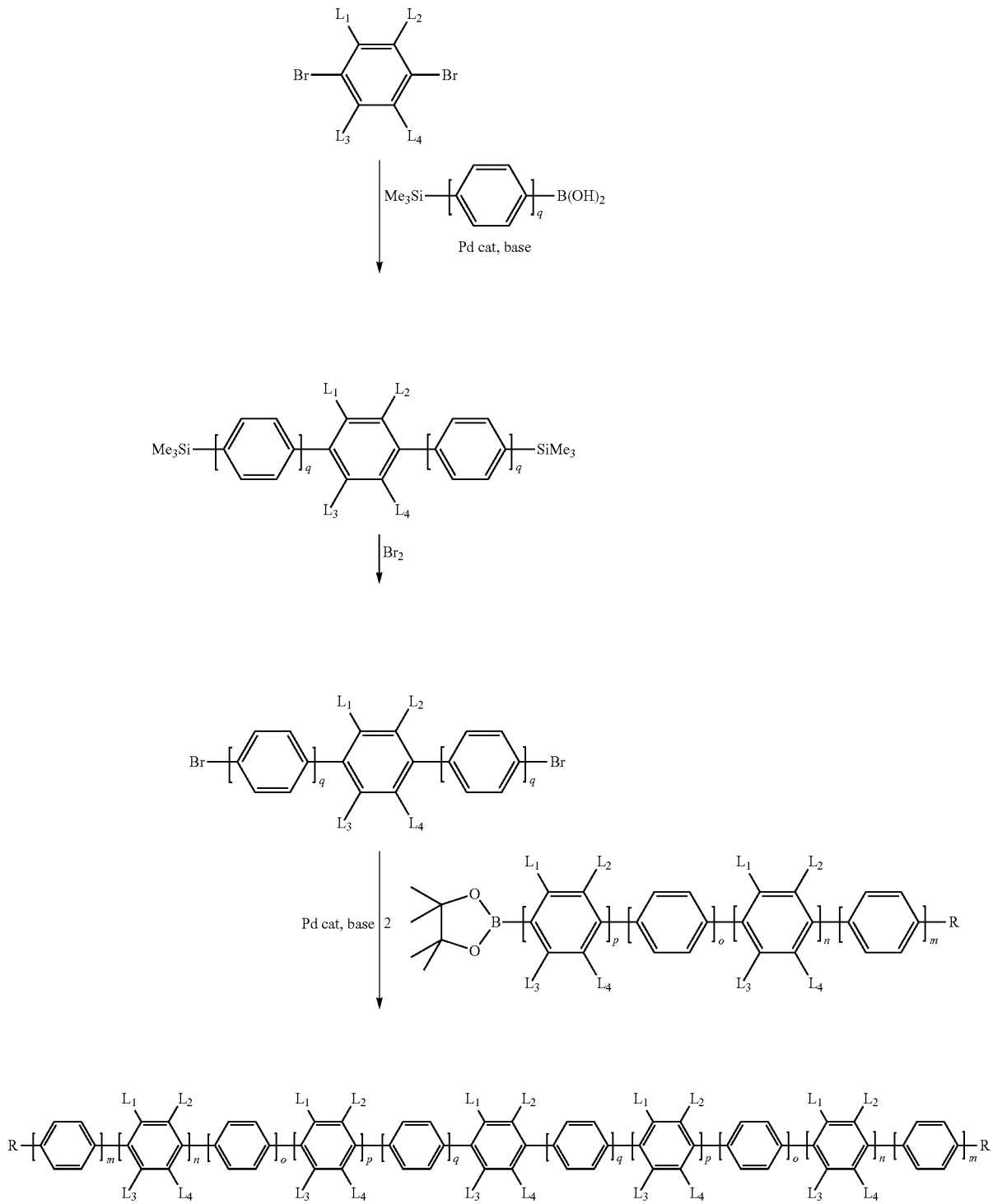

where, in Schemes I and II,
$L_i$ in each case, independently of one another, has the meanings given above for $L^{11}$ in formula I, i.e.
$L_1$ has the meanings given for $L^{11}$ to
$L_4$ has the meanings given for $L^{14}$
m, n, o, p and q denote 0, 1 or 2, and
the sum (m+n+o+p+q) denotes 3 to 7.

Compounds having lateral methyl substituents can be prepared in accordance with Scheme I. The starting material required for this purpose, bromoiodotoluene, is commercially available. Alternatively, a procedure analogous to the following Scheme III can be followed. The second step here, the reaction of the aldehyde with the Grignard compound, can be omitted. In this case, the aldehyde is reduced directly to the methyl.

Reaction Scheme III
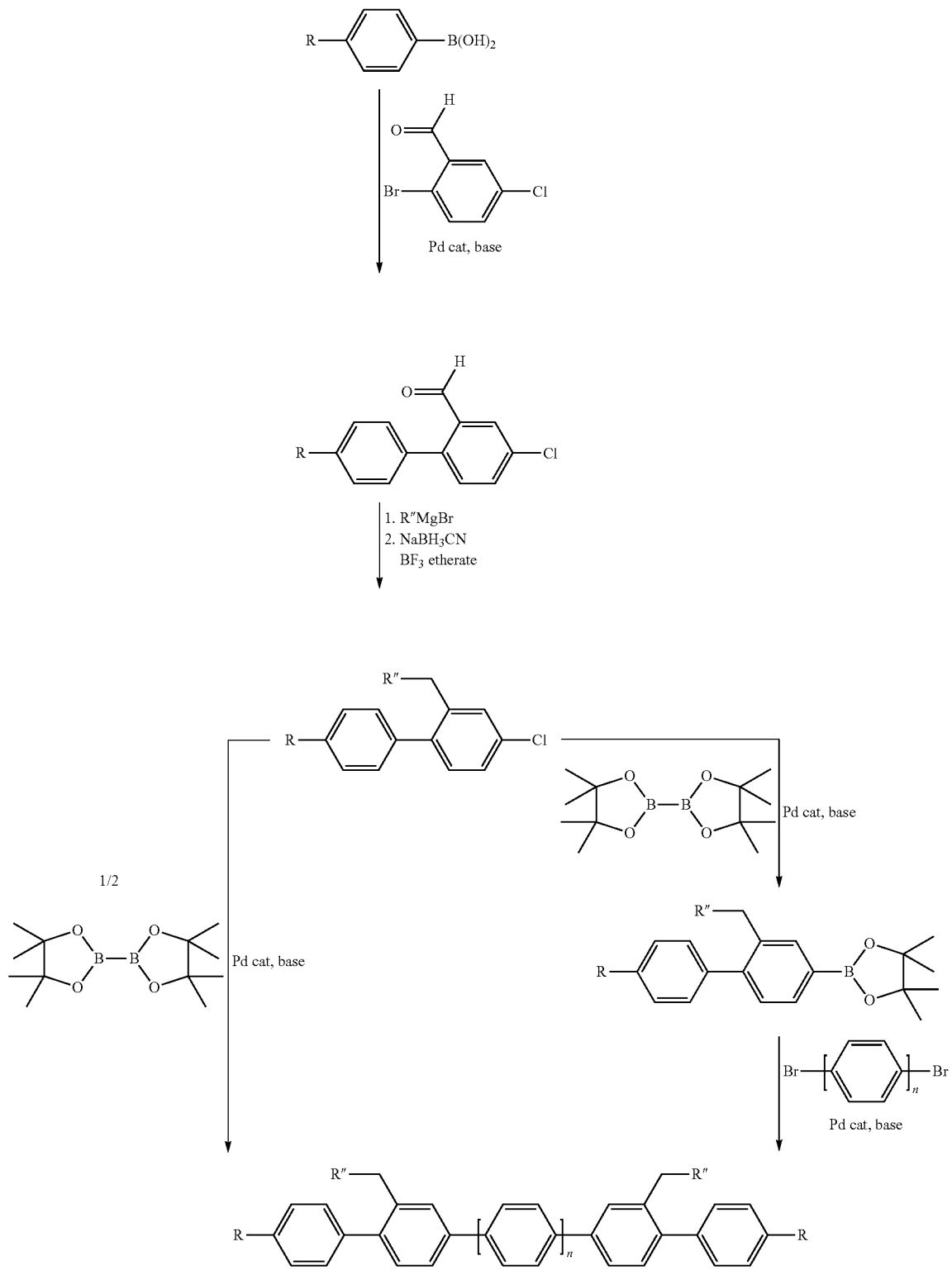
in which
R, in each case independently of one another, denotes $R^{11}$ as defined under formula I, preferably alkyl,
n denotes 2 and optionally 3, preferably 2, and
R", in each case independently of one another, denotes alkyl, preferably having 1 to 11, particularly preferably having 1 to 7 and very particularly preferably having 2 to 5 C atoms.

Reaction Scheme IV
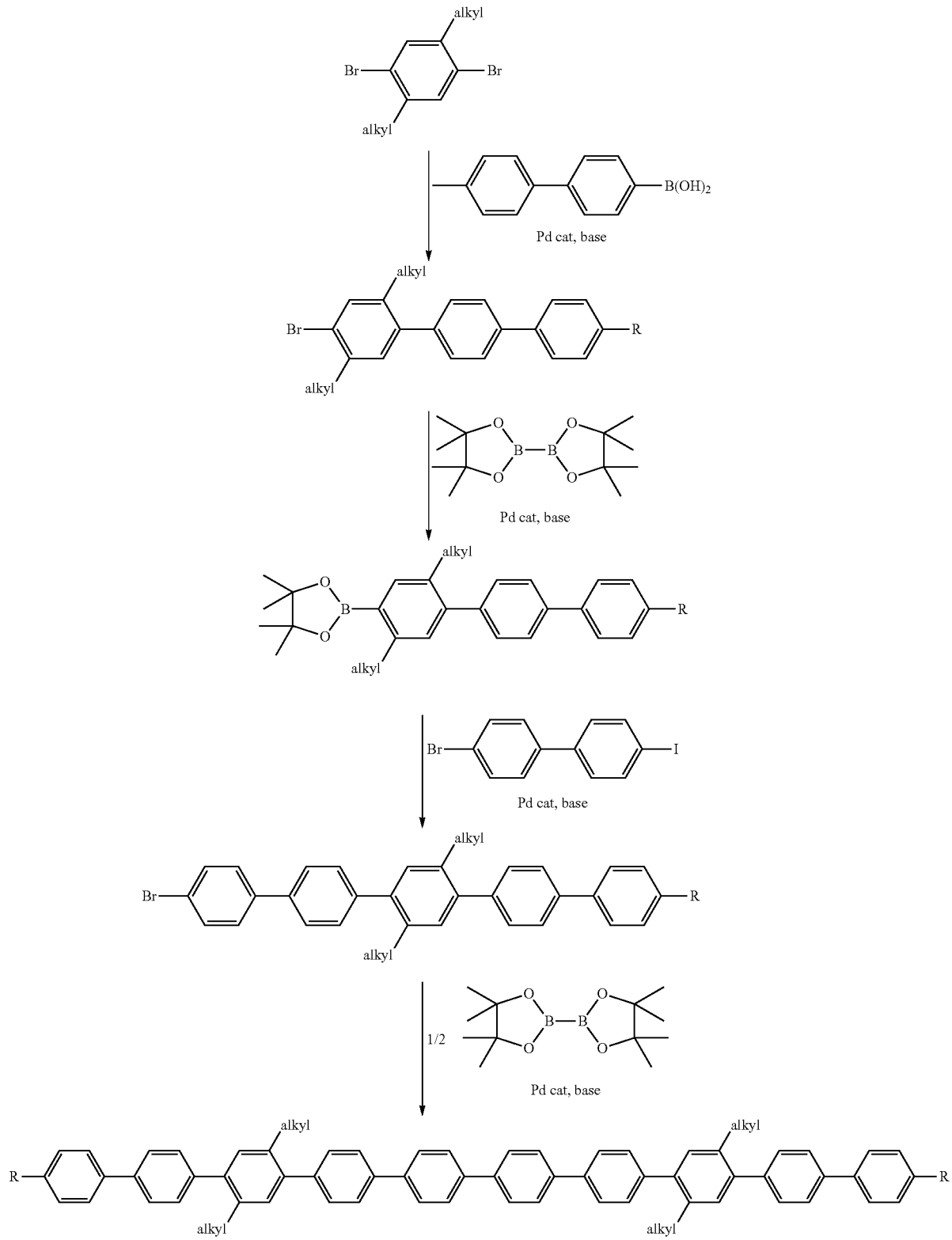
in which
R, in each case independently of one another, denotes $R^{11}$ as defined under formula I, preferably alkyl, and
"alkyl" preferably denotes alkyl having 1 to 15 C atoms.
The term "alkyl" preferably encompasses straight-chain and branched alkyl groups, as well as cycloalkyl groups, each having 1 to 15 carbon atoms, in particular the straight-chain groups methyl, ethyl, propyl, butyl, pentyl, hexyl and heptyl, as well as cyclopropyl and cyclohexyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote an integer from 1 to 10. Preferably, n is 1 and m is 1 to 6.

Compounds containing a vinyl end group and compounds containing a methyl end group have low rotational viscosity.

In the present application, both high-frequency technology and hyperfrequency technology denote applications having frequencies in the range from 1 MHz to 1 THz, preferably from 1 GHz to 500 GHz, more preferably 2 GHz to 300 GHz, particularly preferably from about 5 to 150 GHz and very particularly preferably in the range from about 10 to 80 GHz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

The liquid-crystal media according to the invention consist of a plurality of compounds, preferably 3 to 30, more preferably 4 to 20 and very preferably 4 to 15 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, having n, m and l C atoms respectively, where n, m and l, independently of one another, denote an integer from 1 to 9, preferably 1 to 7, or from 2 to 9, preferably 2 to 7, respectively. $C_oH_{2o+1}$ denotes straight-chain alkyl having 1 to 7, preferably 1 to 4, C atoms, or branched alkyl having 1 to 7, preferably 1 to 4, C atoms.

Table A lists the codes used for the ring elements of the core structures of the compounds, while Table B shows the linking groups. Table C gives the meanings of the codes for the left-hand or right-hand end groups. Table D shows illustrative structures of compounds with their respective abbreviations.

TABLE A

Ring elements

C 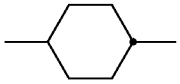

D 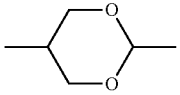

A 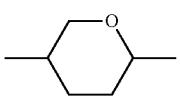

G 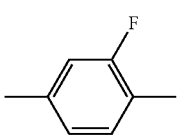

U 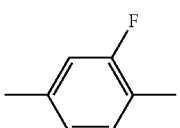

P 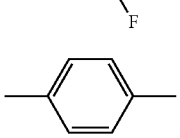

Dl 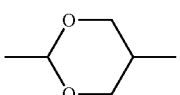

Al 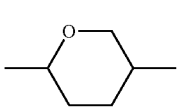

Gl 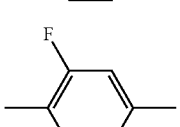

TABLE A-continued
| Ring elements | | |
|---|---|---|
| Ul | 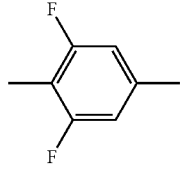 | |
| Y | 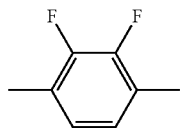 | |
| fX | 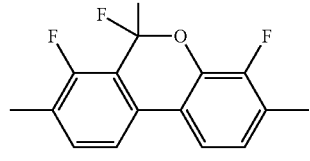 | |
| M | 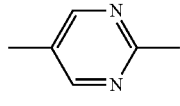 | |
| N | 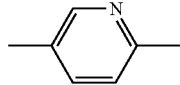 | |
| fN | 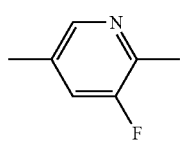 | |
| dH | 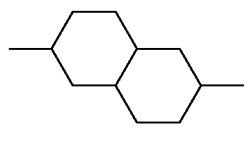 | |
| N3f | 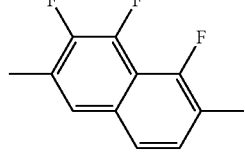 | |
| tH | 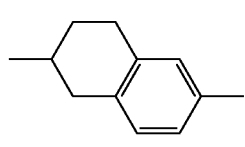 | |
| tH2f | 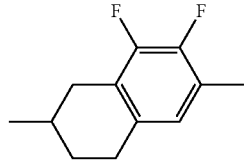 | |
| (1,4N) | 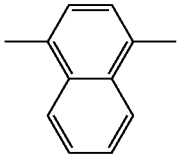 | |
| fXl | 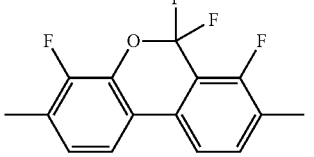 | |
| Ml | 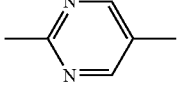 | |
| Nl | 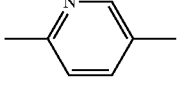 | |
| fNl | 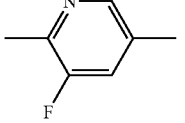 | |
| Np | 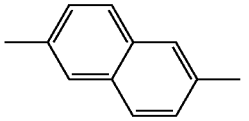 | |
| N3fl | 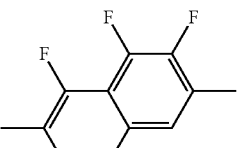 | |
| tHl | 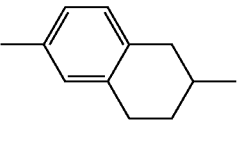 | |
| tH2fl | 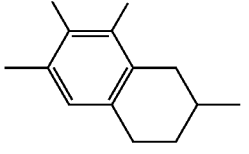 | |
| K | 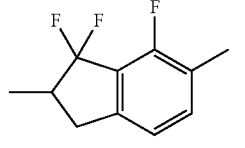 | |
| L | 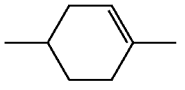 | |

TABLE A-continued

Ring elements

| Symbol | Structure |
|---|---|
| F | cyclohexene with F |
| P(o) | benzene with $C_oH_{2o+1}$ |
| P(c3) | benzene with cyclopropyl |
| P(c4) | benzene with cyclobutyl |
| P(c5) | benzene with cyclopentyl |
| P(c6) | benzene with cyclohexyl |
| Kl | indane with F, F, F |
| Ll | cyclohexene |
| Fl | cyclohexene with F |
| Pl(o) | benzene with $C_oH_{2o+1}$ |
| Pl(c3) | benzene with cyclopropyl |
| Pl(c4) | benzene with cyclobutyl |
| Pl(c5) | benzene with cyclopentyl |
| Pl(c6) | benzene with cyclohexyl |

TABLE B

Linking groups

| | | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CF$_2$CF$_2$— | T | —C≡C— |

TABLE C

End groups

| Left-hand side | | Right-hand side | |
|---|---|---|---|
| \multicolumn{4}{c}{Use alone} | | | |
| -n- | $C_nH_{2n+1}$— | -n | —$C_nH_{2n+1}$ |
| -nO- | $C_nH_{2n+1}$—O— | -nO | —O—$C_nH_{2n+1}$ |

TABLE C-continued

| End groups | | | |
|---|---|---|---|
| Left-hand side | | Right-hand side | |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n+1}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -OXF- | CF$_2$=CH—O— | -OXF | —O—CH=CF$_2$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |
| Use together with others | | | |
| -...A...- | —C≡C— | -...A... | —C≡C— |
| -...V...- | CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots "..." are placeholders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures
The illustrative structures show compounds which are particularly preferably employed.

Examples of compounds of component A

6*P-1, phase sequence: C 197° C. N 330.4° C. I

6*P-2, phase sequence: C 174° C. N 252.7° C. I

10*P-1 (k = 2), phase sequence: C 154° C. N 283.9° C. I

TABLE D-continued
Illustrative structures
The illustrative structures show compounds which are particularly preferably employed.
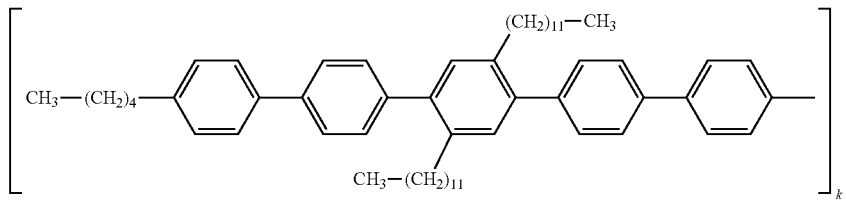
10*P-2 (k = 2), phase sequence: C 103° C. N 199.9° C. I
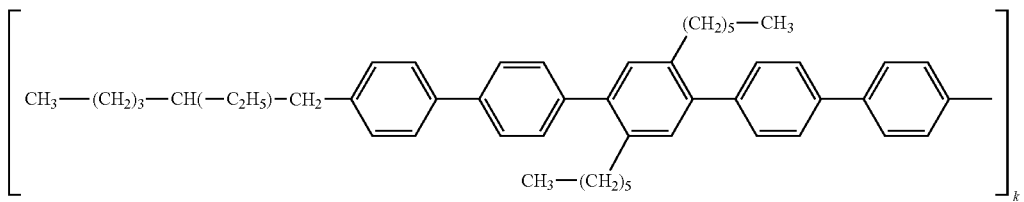
10*P-3 (k = 2), phase sequence: C 147° C. N 238.4° C. I
Examples of compounds of component B
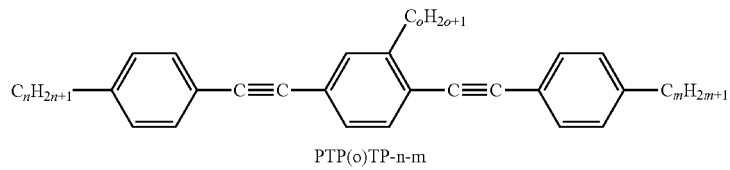
PTP(o)TP-n-m
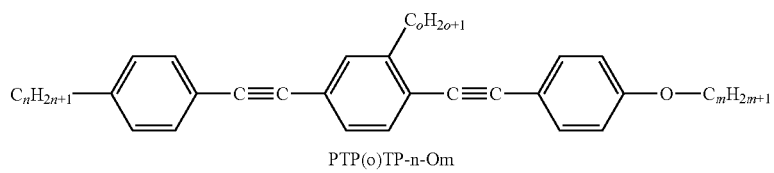
PTP(o)TP-n-Om
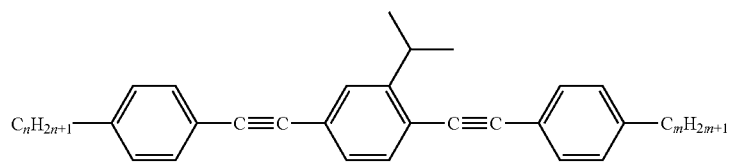
PTP(i3)TP-n-m,
Phase sequence: n = m = 2: C 99° C. N (45.4) ° C. I;
n = m = 3: $T_g$ -30° C. C 68° C. N 76.2° C. I;
n = m = 4: C 44° C. N 49.5° C. I
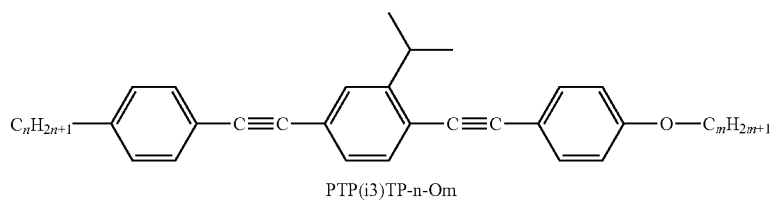
PTP(i3)TP-n-Om TABLE D-continued
Illustrative structures
The illustrative structures show compounds which are particularly preferably employed.
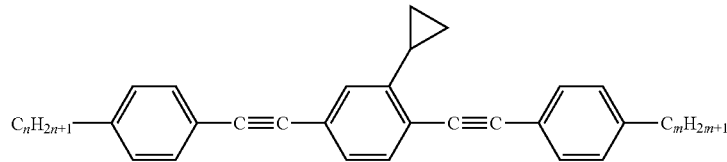
PTP(c3)TP-n-m,
Phase sequence: n = m = 3: $T_g$ -43° C. C 46° C. N 86.0° C. I;
n = m = 4: C 72° C. N 84.5° C. I
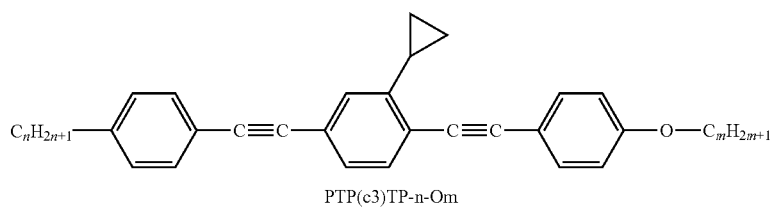
PTP(c3)TP-n-Om
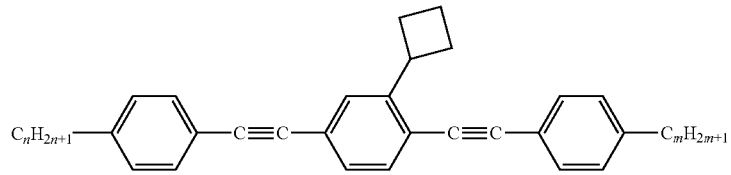
PTP(c4)TP-n-m,
Phase sequence: n = m = 4: $T_g$ -39° C. C 69° C. N 70.1° C. I
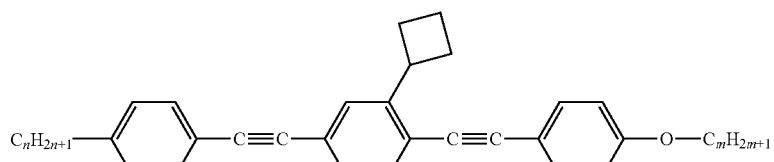
PTP(c4)TP-n-Om
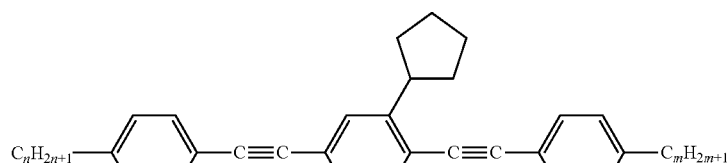
PTP(c5)TP-n-m
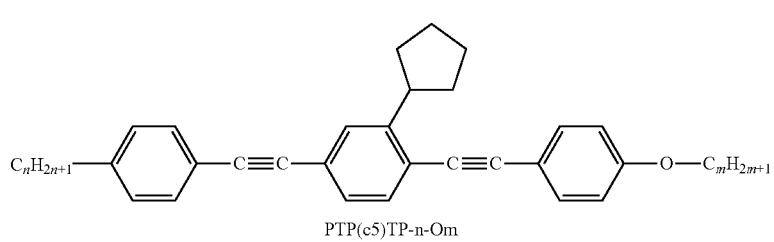
PTP(c5)TP-n-Om TABLE D-continued
Illustrative structures
The illustrative structures show compounds which are particularly preferably employed.
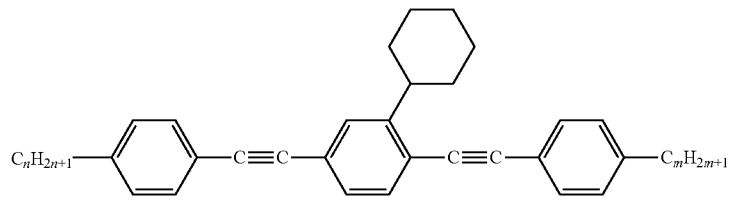
PTP(c6)TP-n-m,
Phase sequence: n = m = 3: $T_g$ -23° C. I
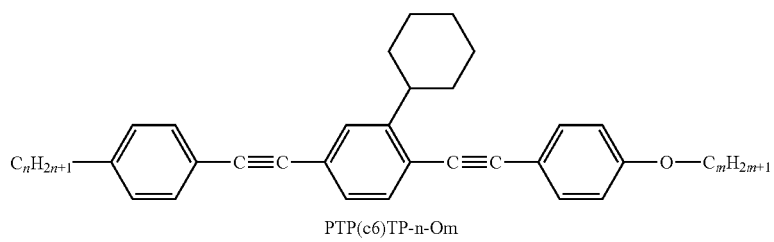
PTP(c6)TP-n-Om
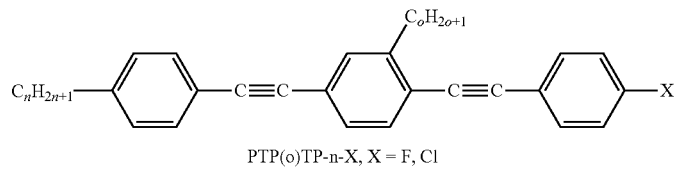
PTP(o)TP-n-X, X = F, Cl
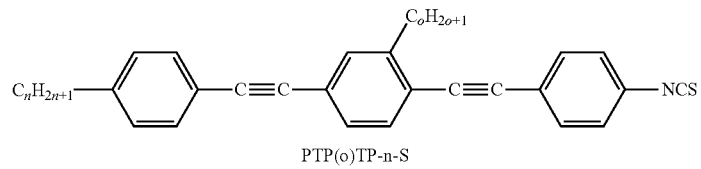
PTP(o)TP-n-S
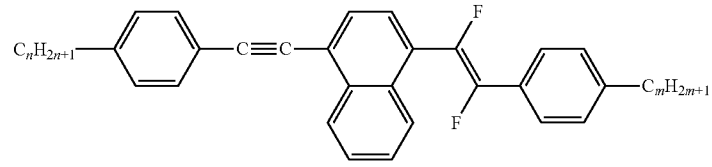
PT(1,4N)BP-n-m,
Phase sequence: n = 3, m = 4: $T_g$ -34° C. C 67° C. N 180.6° C. I;
n = m = 4: $T_g$ -37° C. C 65° C. N 162.0° C. I
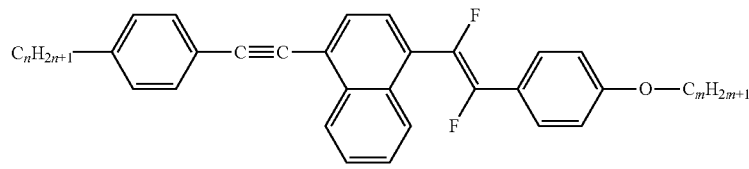
PT(1,4N)BP-n-Om TABLE D-continued
Illustrative structures
The illustrative structures show compounds which are particularly preferably employed.
Examples of compounds of component C
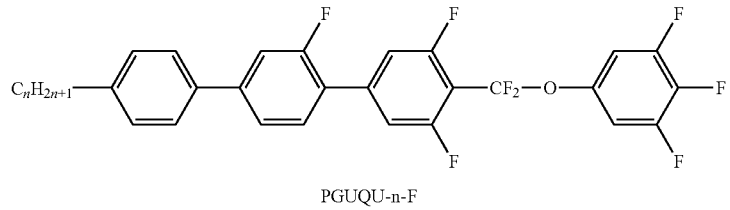
PGUQU-n-F
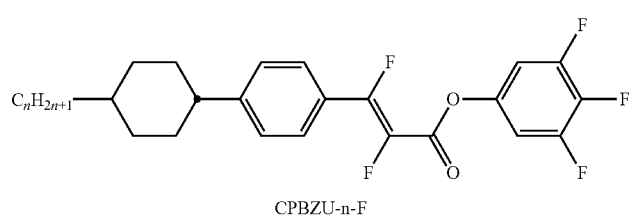
CPBZU-n-F
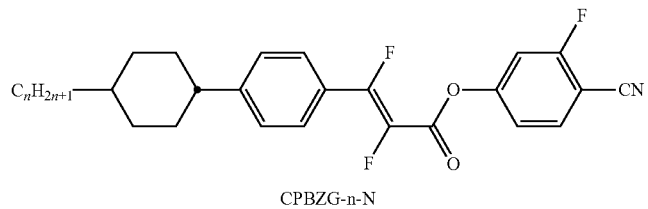
CPBZG-n-N
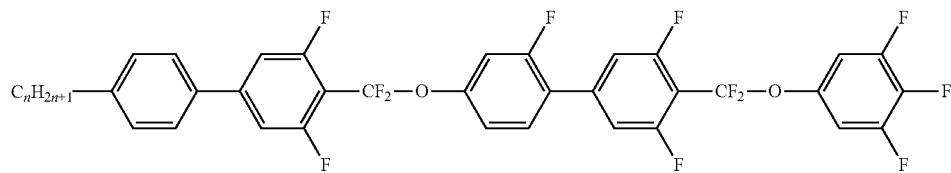
PUQGUQU-n-F
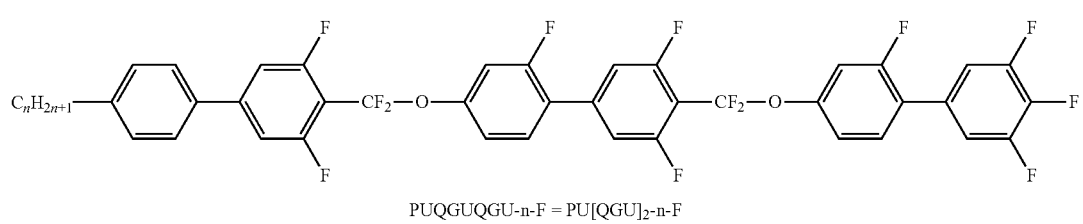
PUQGUQGU-n-F = PU[QGU]$_2$-n-F
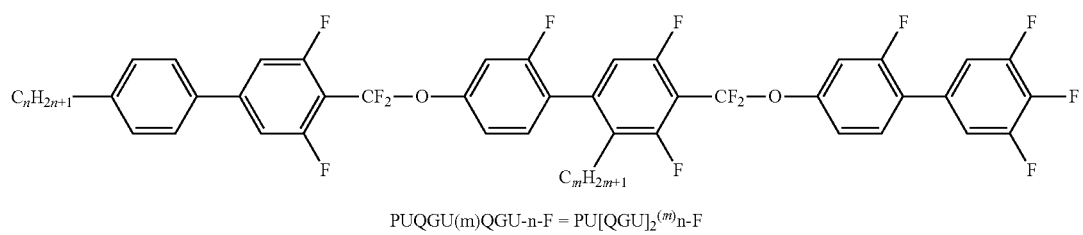
PUQGU(m)QGU-n-F = PU[QGU]$_2^{(m)}$n-F
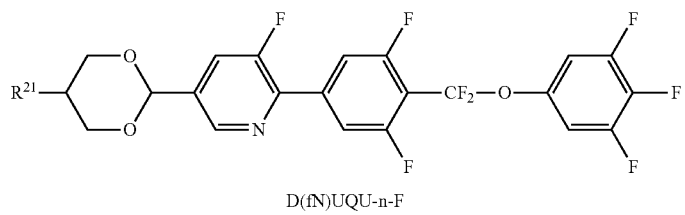
D(fN)UQU-n-F TABLE D-continued
Illustrative structures
The illustrative structures show compounds which are particularly preferably employed.
Examples of compounds of component D
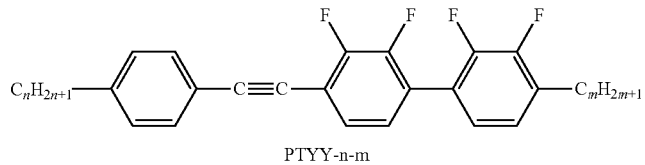
PTYY-n-m
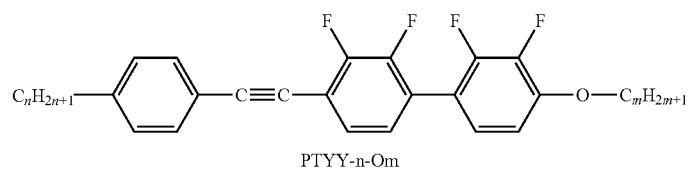
PTYY-n-Om
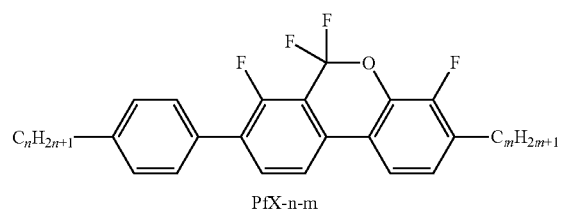
PfX-n-m
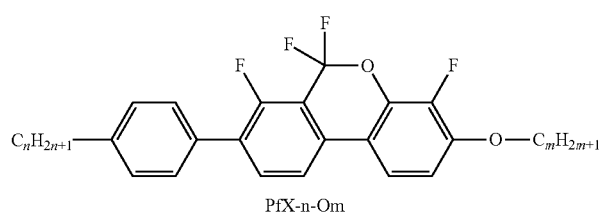
PfX-n-Om
Examples of compounds of component E
Compounds having three 6-membered rings
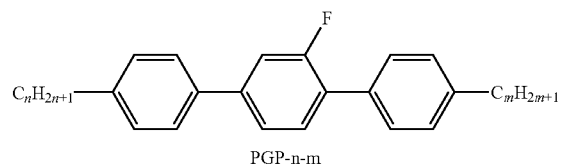
PGP-n-m
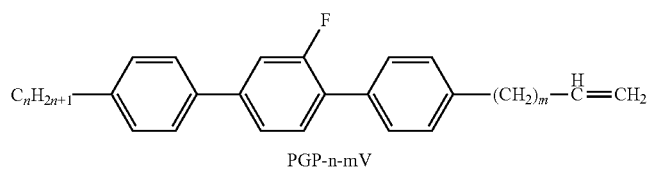
PGP-n-mV
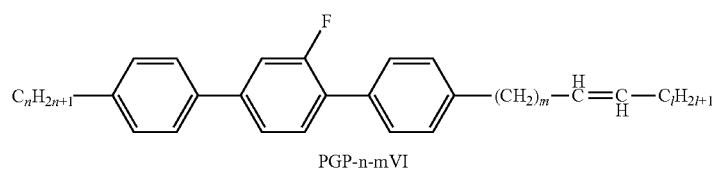
PGP-n-mVI TABLE D-continued
Illustrative structures
The illustrative structures show compounds which are particularly preferably employed.
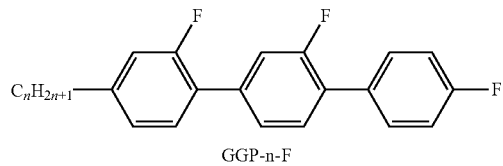
GGP-n-F
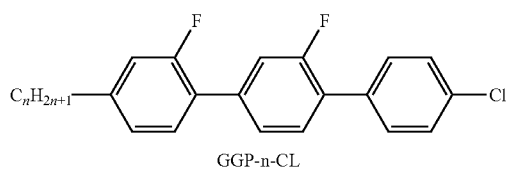
GGP-n-CL
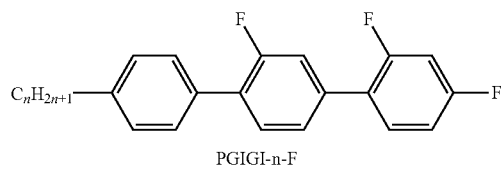
PGIGI-n-F
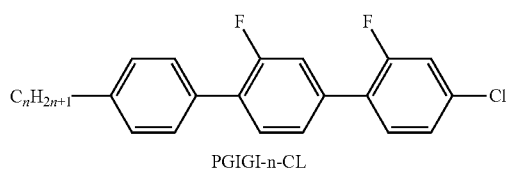
PGIGI-n-CL
Compounds having four 6-membered rings
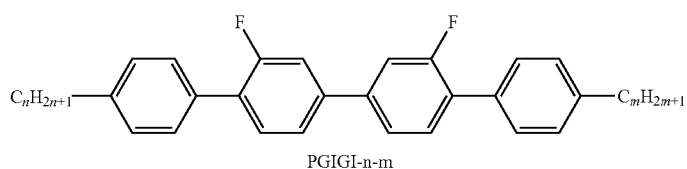
PGIGI-n-m
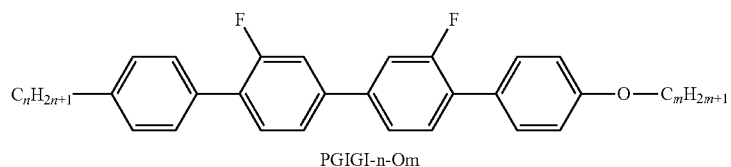
PGIGI-n-Om
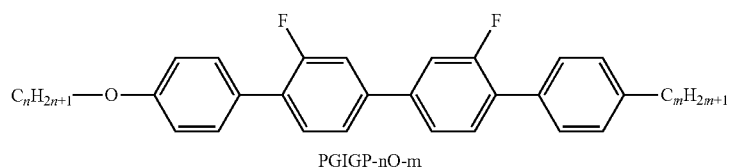
PGIGP-nO-m
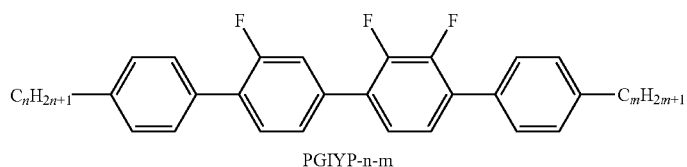
PGIYP-n-m TABLE D-continued
*Illustrative structures*
The illustrative structures show compounds which are particularly preferably employed.
Illustrative structures of polar compounds employed:
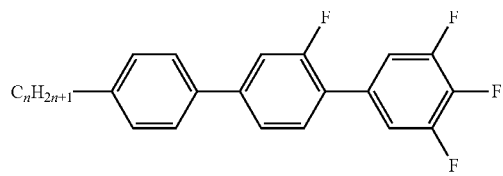
PGU-n-F
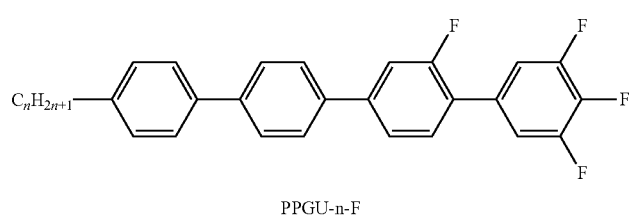
PPGU-n-F
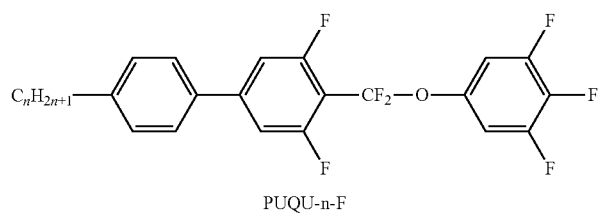
PUQU-n-F
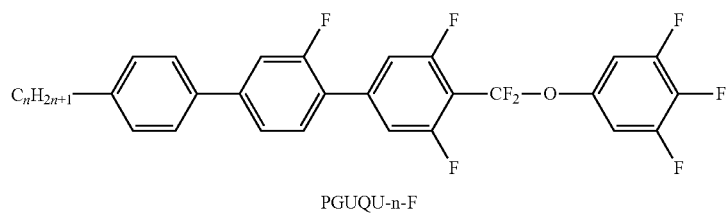
PGUQU-n-F
Illustrative structures of further neutral compounds preferably employed:
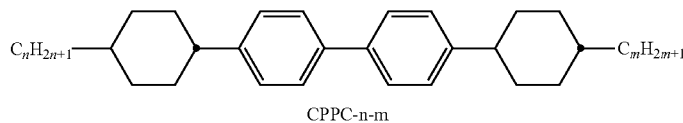
CPPC-n-m
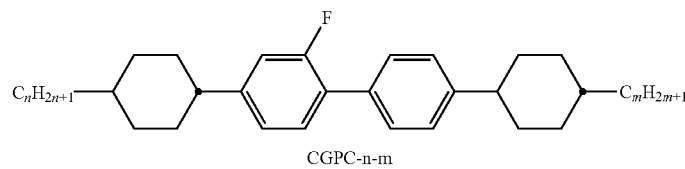
CGPC-n-m
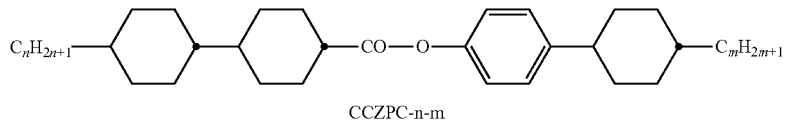
CCZPC-n-m TABLE D-continued
*Illustrative structures*
The illustrative structures show compounds which are particularly preferably employed.
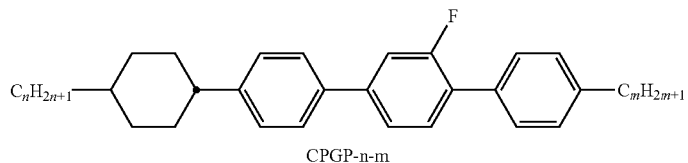
CPGP-n-m
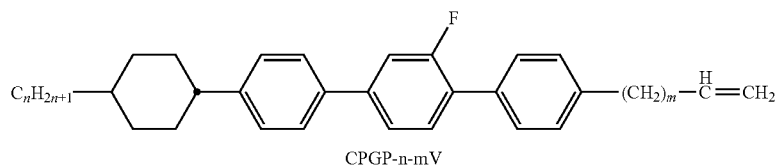
CPGP-n-mV
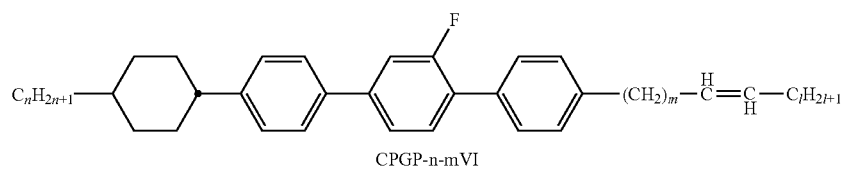
CPGP-n-mVI
Illustrative structures of further polar compounds employed:
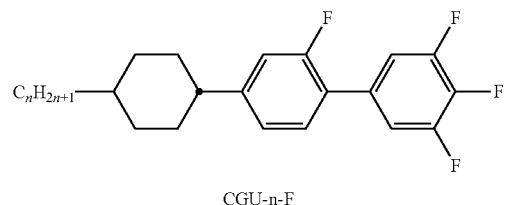
CGU-n-F
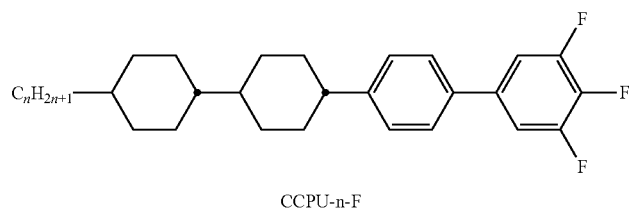
CCPU-n-F
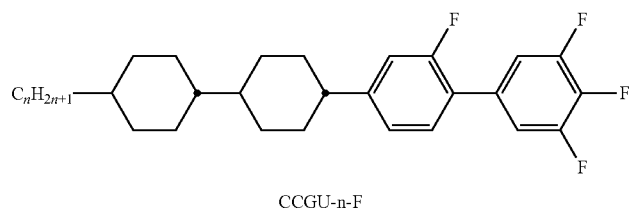
CCGU-n-F
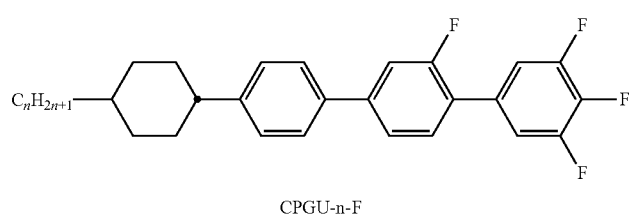
CPGU-n-F TABLE D-continued Illustrative structures
The illustrative structures show compounds which are particularly preferably employed.

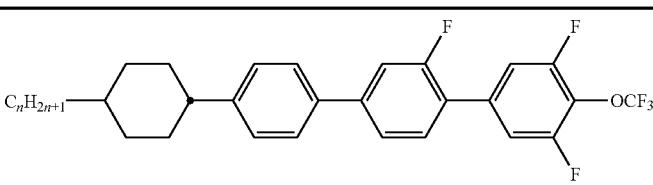

CPGU-n-OT

The following table, Table E, shows illustrative compounds which can be used as stabiliser in the mesogenic media in accordance with the present invention. The total concentration of these and similar compounds in the media is preferably 5% or less.

TABLE E

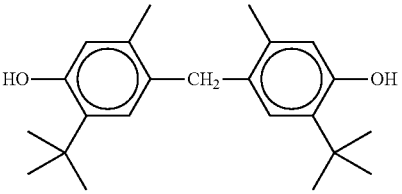

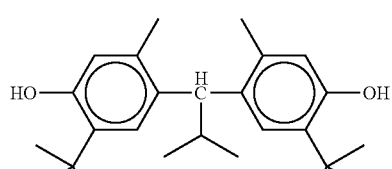

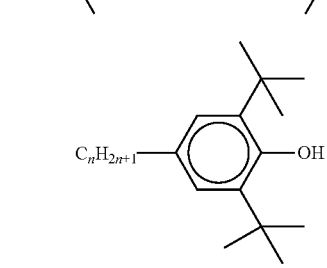

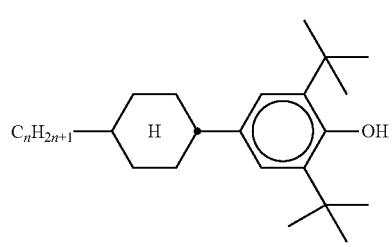

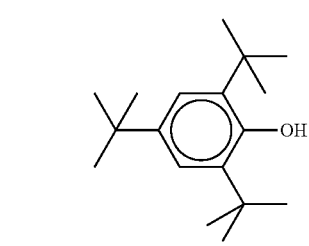

TABLE E-continued

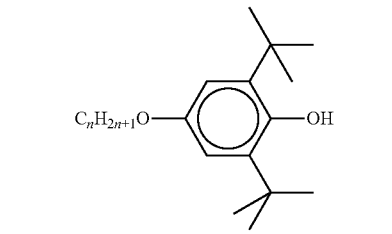

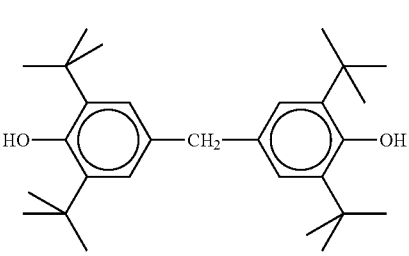

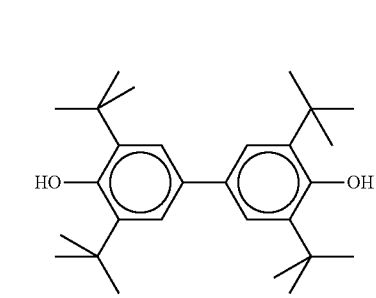

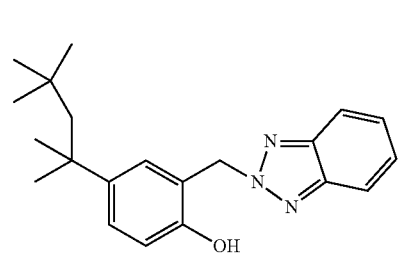 [SMILES: CC(C)(C)CC(C)(C)c1ccc(O)c(Cn2nc3ccccc3n2)c1]

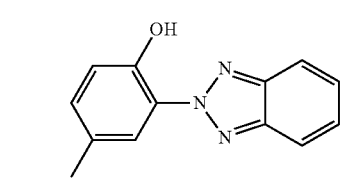 [SMILES: Cc1ccc(O)c(-n2nc3ccccc3n2)c1]

TABLE E-continued
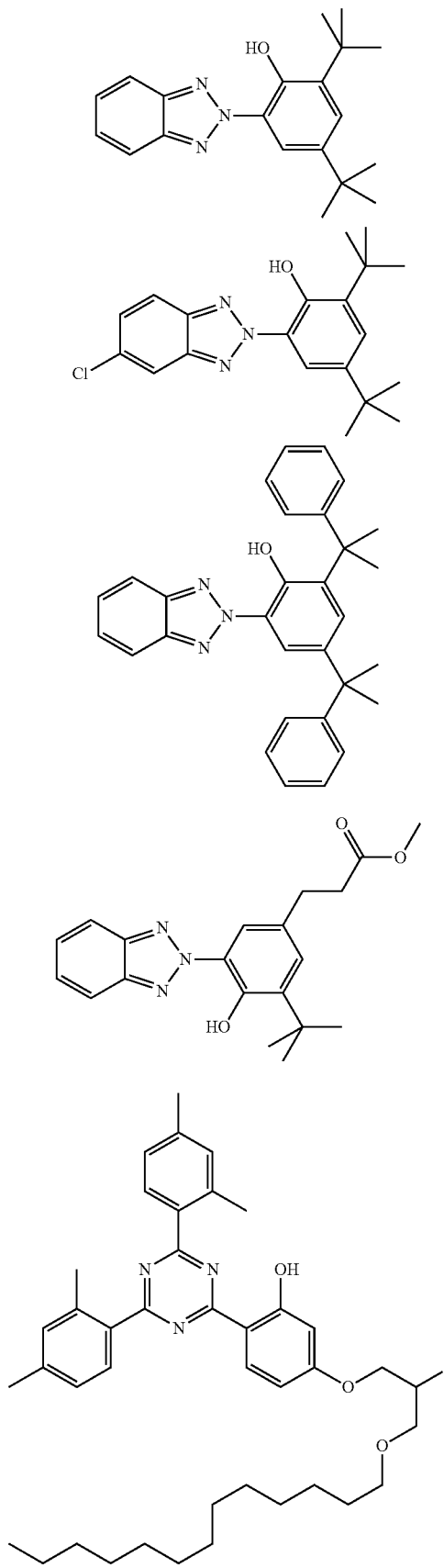
TABLE E-continued
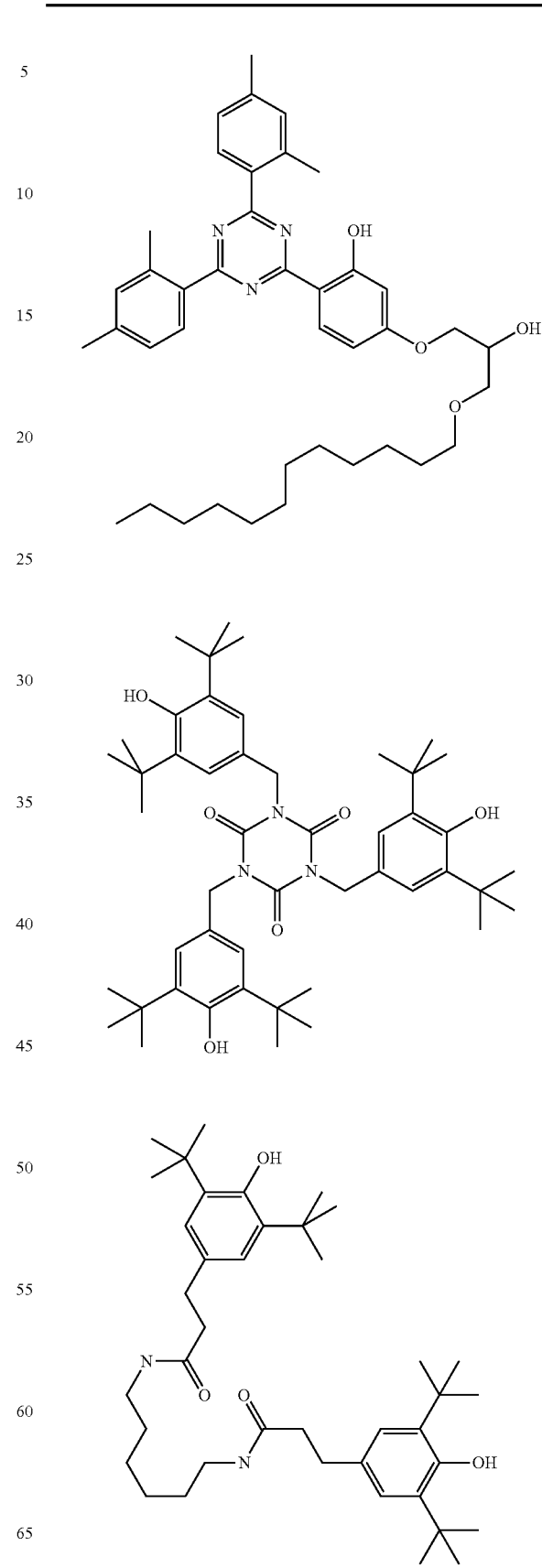

TABLE E-continued
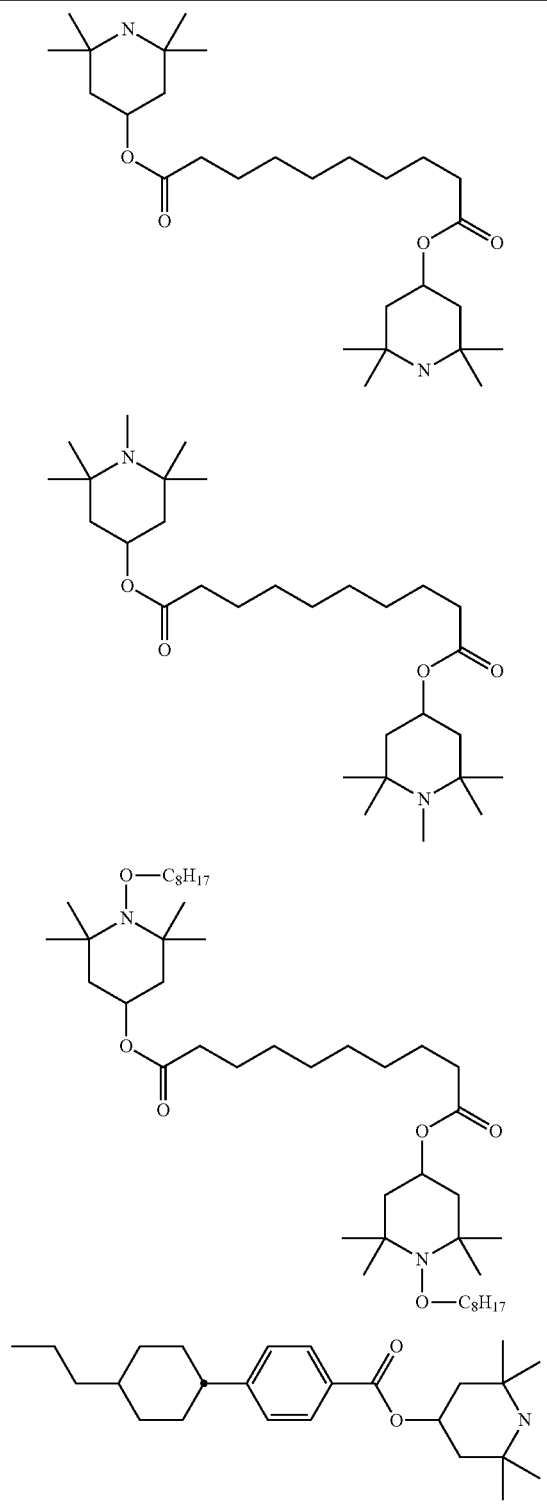
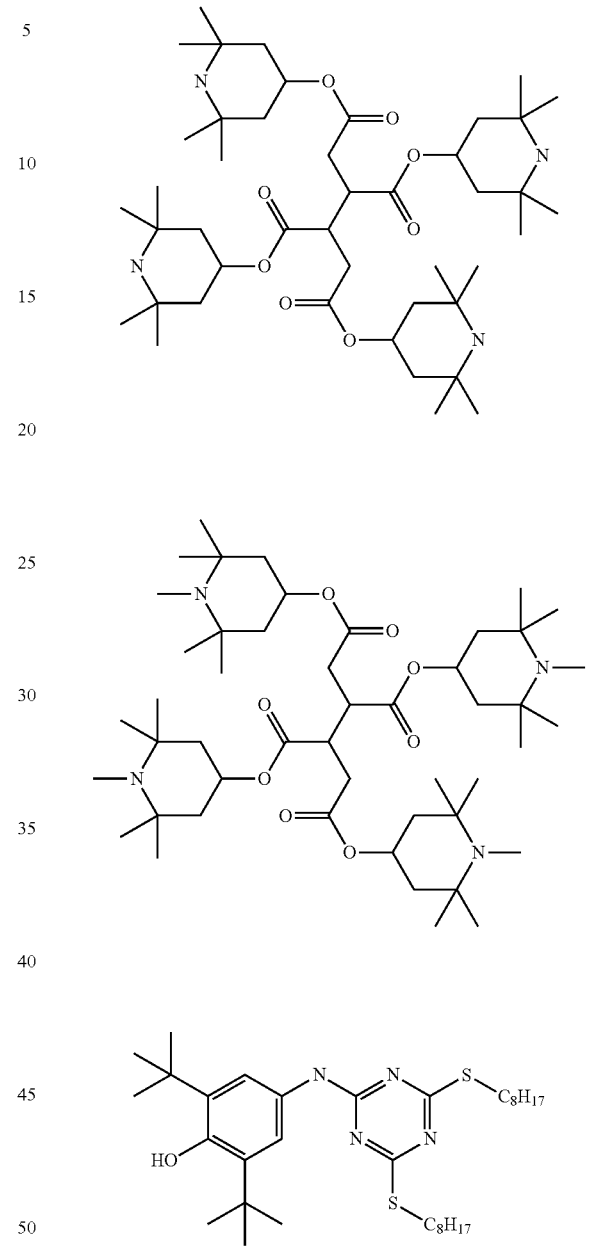
In a preferred embodiment of the present invention, the mesogenic media comprise one or more compounds selected from the group of the compounds from Table E.
The following table, Table F, shows illustrative compounds which can preferably be used as chiral dopants in the mesogenic media in accordance with the present invention.
TABLE F
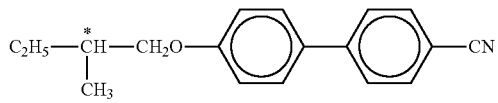
C 15

TABLE F-continued

| Structure | Name |
|---|---|
| C₂H₅–*CH(CH₃)–CH₂–C₆H₄–C₆H₄–CN | CB 15 |
| C₆H₁₃–*CH(CH₃)–O–C₆H₄–C(=O)O–C₆H₄–C₅H₁₁ | CM 21 |
| C₃H₇–Cy–Cy–C₆H₄–CH₂–*CH(CH₃)–C₂H₅ | CM 44 |
| C₅H₁₁–C₆H₄–C₆H₄–C(=O)O–*CH(C₂H₅)–C₆H₅ | CM 45 |
| C₈H₁₇O–C₆H₄–C₆H₄–C(=O)O–*CH(C₂H₅)–C₆H₅ | CM 47 |
| Cholesteryl chloride | CC |
| Cholesteryl nonanoate (C₈H₁₇C(=O)O–) | CN |
| C₆H₁₃O–C₆H₄–C(=O)O–C₆H₄–C(=O)O–*CH(CH₃)–C₆H₁₃ | R/S-811 |
| C₅H₁₁–Cy–C₆H₄–COO–CH₂–*CH(C₆H₅)–OOC–C₆H₄–Cy–C₅H₁₁ | R/S-1011 |

TABLE F-continued

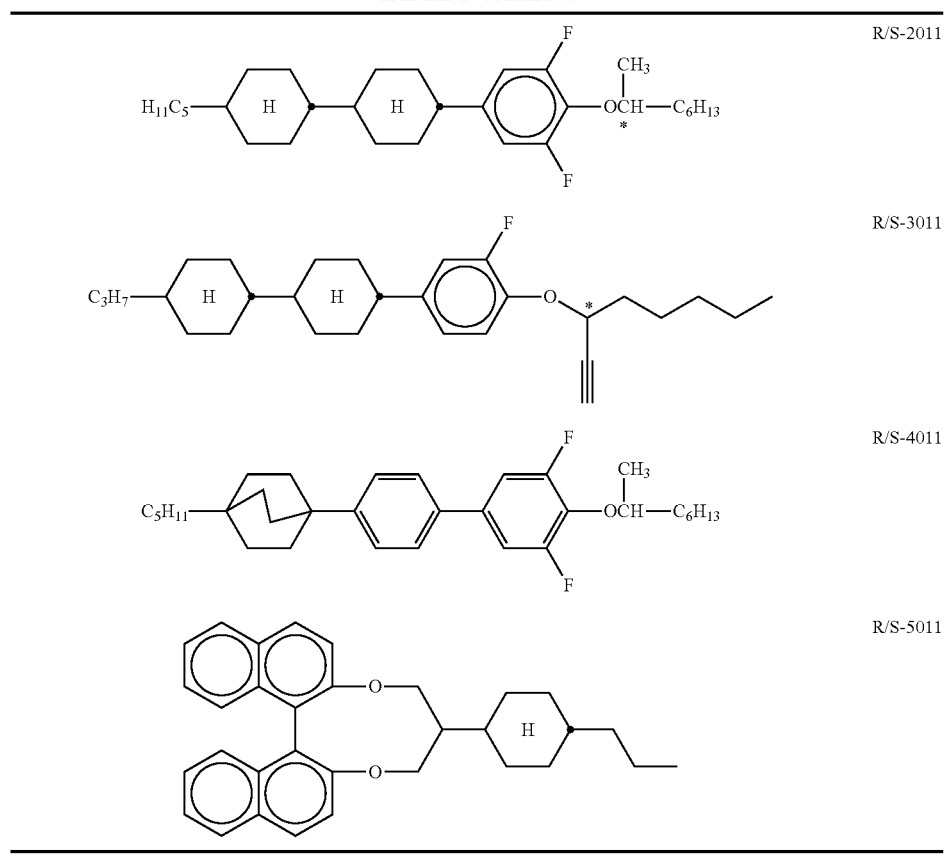

In a preferred embodiment of the present invention, the mesogenic media comprise one or more compounds selected from the group of the compounds from Table F.

The mesogenic media in accordance with the present application preferably comprise two or more, preferably four or more, compounds selected from the group consisting of the compounds from the above tables.

The liquid-crystal media in accordance with the present invention preferably comprise
- seven or more, preferably eight or more, compounds, preferably compounds having three or more, preferably four or more, different formulae, selected from the group of the compounds from Table D.

EXAMPLES

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

Substance Examples

Substance Example 1

Preparation of the Compound

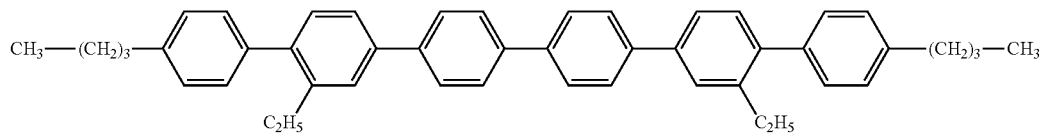

Step 1.1

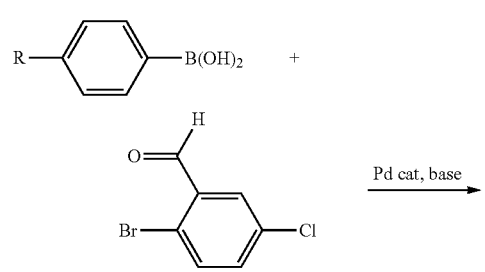

-continued

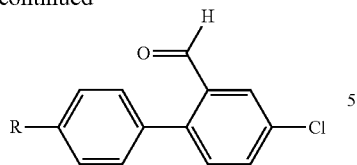

24.0 g of sodium metaborate are dissolved in 60.0 ml of demineralised water. 1.50 g of bis(triphenylphosphine)palladium(II) chloride (15.2% of Pd) for synthesis, 0.100 ml of hydrazinium hydroxide (approximately 100% pure) and 25.0 g of 2-bromo-5-chlorobenzaldehyde are then added successively, and the mixture is stirred at ambient temperature for 10 min. 19.7 g of the borate dissolved in 120.0 ml of tetrahydrofuran are then added dropwise, and the mixture is heated to the boil. The mixture is heated under reflux for 16 h. The product is subjected to conventional purification. A yellow oil is obtained.
Step 1.2

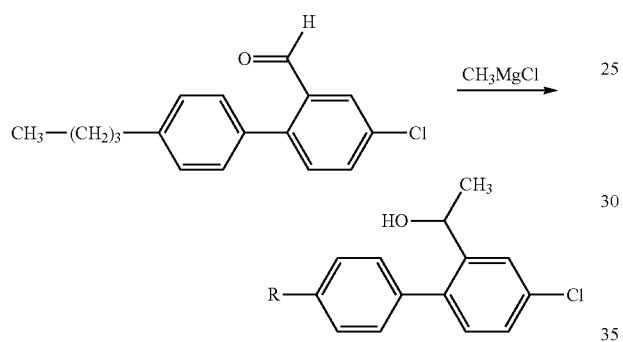

18.0 ml of a 20% solution of methylmagnesium chloride in tetrahydrofuran are initially introduced. 11.2 g of the product from the final step are dissolved in 100 ml of THF and added dropwise with cooling at a temperature of about 5° C. The reaction mixture is subsequently stirred at a temperature of 5° C. for 1 h. The product is subjected to conventional purification. As clear, pale-yellow, viscous oil is obtained.
Step 1.3

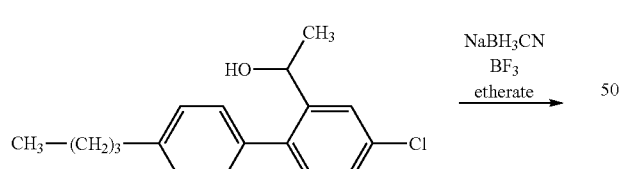

-continued

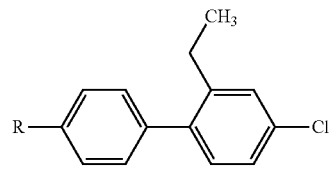

9.20 g of the product from the final step are dissolved in 150.0 ml of tetrahydrofuran at ambient temperature under a nitrogen atmosphere. 49.0 ml of a solution of boron trfluoride/diehyl ether complex (for synthesis) are then added dropwise. During this addition, the temperature of the reaction mixture rises to about 28° C. 17.40 g of sodium cyanoborohydride are then added in portions. During this addition, the temperature rises to about 35° C. The mixture is subsequently heated under reflux for 70 h. 60 g of crude product are obtained as a yellow, viscous oil. The product is subjected to conventional purification.
Step 1.4

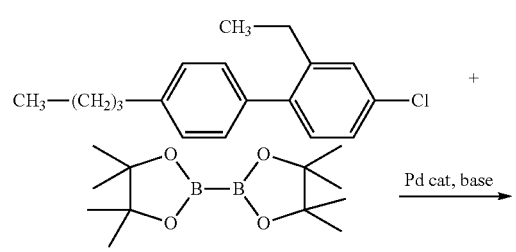

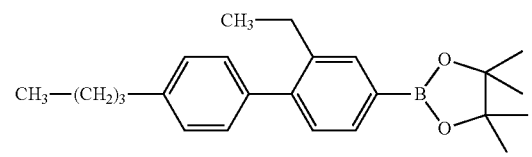

7.20 g of the product from the final step are dissolved in 100.0 ml of 1,4-dioxane with 13.3 g of bis(pinacolato)diboron, 490.0 mg of tris(dibenzylideneacetone)dipalladium (0), 510 mg of 2-dicyclohexylphosphino-2',4',6'-triisopropylbiphenyl and 7.70 g of potassium acetate. The mixture is heated under reflux at 100° C. for 16 h. The product is subjected to conventional purification.
Step 1.5

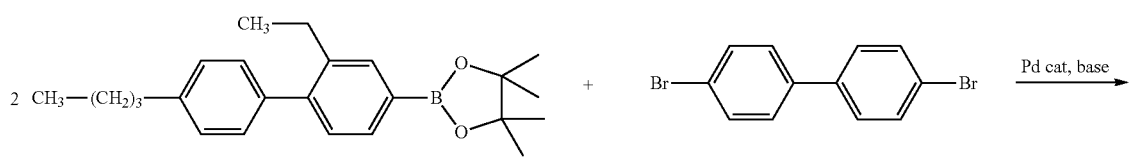

-continued

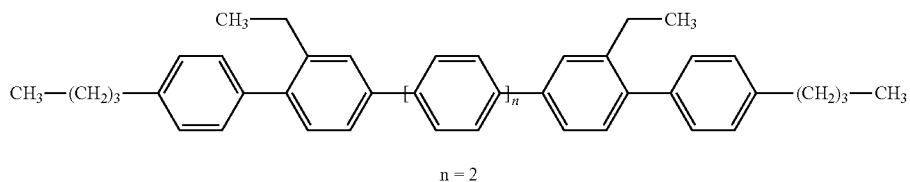

n = 2

3.00 g of the product from the final step are dissolved in 50.0 ml of 1,4-dioxane with 1.28 g of 4,4'-dibromophenyl for synthesis, 300.0 mg of tris(dibenzylideneacetone)dipalladium(0), 35.0 mg of 2-dicyclohexylphosphino-2',6'-dimethoxybiphenyl and 4.80 g of potassium phosphate monohydrate (prepared from potassium phosphate trihydrate at 140° C. after 16 h). The reaction mixture is heated under reflux at 100° C. for 16 h. The crude product (green-blue crystals) is isolated. The product is subjected to conventional purification.

The product has the phase sequence C 197° C. N 330.4° C. I and, extrapolated from a 5% solution in ZLI-4792, a $\Delta\epsilon$ of 2.8 and a $\Delta n$ of 0.351.

Substance Example 2

The following compound is prepared analogously to Substance Example 1

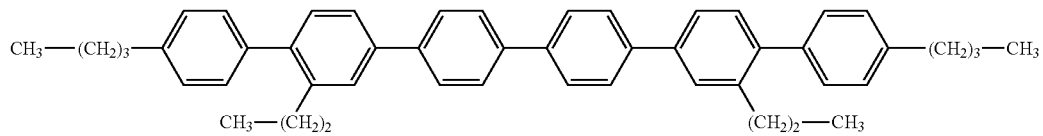

For simplicity, only the final synthetic step is described in detail here.

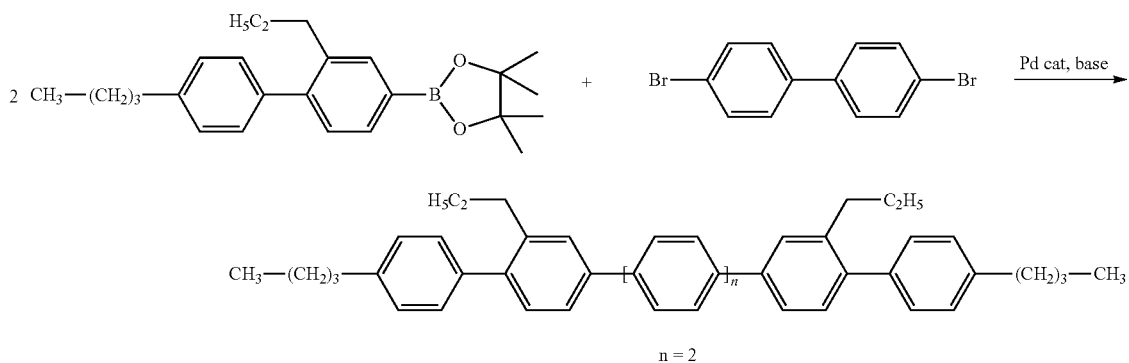

n = 2

3.80 g of the borate are dissolved in 50.0 ml of 1,4-dioxane with 1.560 g of 4,4'-dibromobiphenyl (for synthesis), 90.0 mg of tris(dibenzylideneacetone)dipalladium(0), 170 mg of 2-dicyclohexylphosphino-2',6'-dimethoxybiphenyl and 5.80 g of potassium phosphate monohydrate (prepared from potassium phosphate trihydrate at 140° C. after 16 h). The reaction mixture is heated under reflux at 100° C. for 16 h. The crude product is isolated. The product is subjected to conventional purification. Pale-beige crystals are obtained.

The product has the phase sequence C 174° C. N 252.7° C. I and, extrapolated from a 5% solution in ZLI-4792, a $\Delta\epsilon$ of 1.6 and a $\Delta n$ of 0.319.

Substance Example 3

Preparation of the Compound

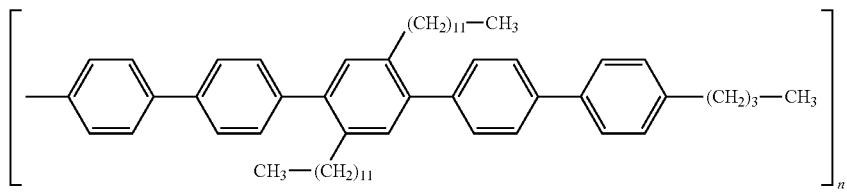

n = 2

Step 3.1

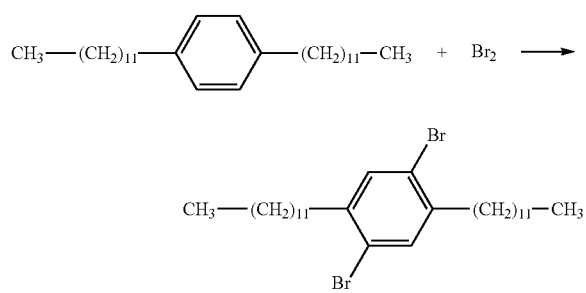

33.50 g of 1,4-di-n-dodecylbenzene, are dissolved in 100 ml of dichloromethane. 200 mg of iodine (double-sublimed) are added as catalyst. 8.5 ml of bromine (extra pure) are subsequently rapidly added dropwise. The brown reaction mixture is stirred at ambient temperature for 16 h with exclusion of light. A further 100 ml of dichloromethane are then added, and the mixture is stirred for a further 50 h. The crude product (pale-yellow crystals) is isolated and subjected to conventional purification. White crystals are obtained.

Step 3.2

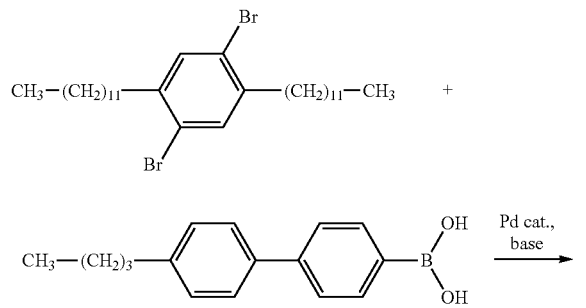

20.0 g of the product from the final step, 100.0 ml of toluene (extra pure), 12.0 g of anhydrous sodium carbonate (extra pure) and 50.0 ml of demineralised water are initially introduced and warmed to a temperature in the range from about 75° C. to 80° C. with vigorous stirring. 0.40 g of tetrakis(triphenylphosphine)Pd(0) is subsequently added, and a solution of 9.40 g of the boronic acid in 50.0 ml of ethanol (absolute, extra pure) is added dropwise. The alcoholic solution of the boronic acid is advantageously slightly warmed in advance in order completely to dissolve the boronic acid. The reaction mixture is heated under reflux for 16 h. The crude product (a brown oil) is isolated and subjected to conventional purification. A clear oil is obtained.

Step 3.3

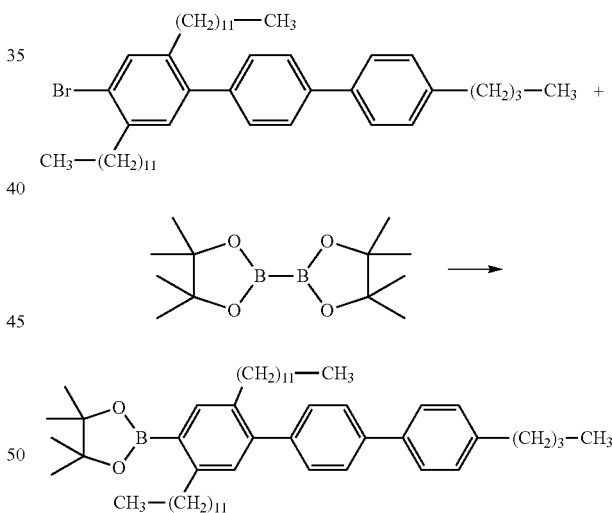

13.60 g of the product from the final step are dissolved in 100.0 ml of 1,4-dioxane (extra pure). 0.40 g of PdCl$_2$-dppf, (bisdiphenylphosphinoferrocenepalladium dichloride) 5.50 g of bis(pinacolato)diboron and 5.40 g of potassium acetate (extra pure) are subsequently added, and the reaction mixture is heated under reflux for 4 h. The crude product is isolated (black oil) and subjected to conventional purification. The product is obtained as an oil.

Step 3.4

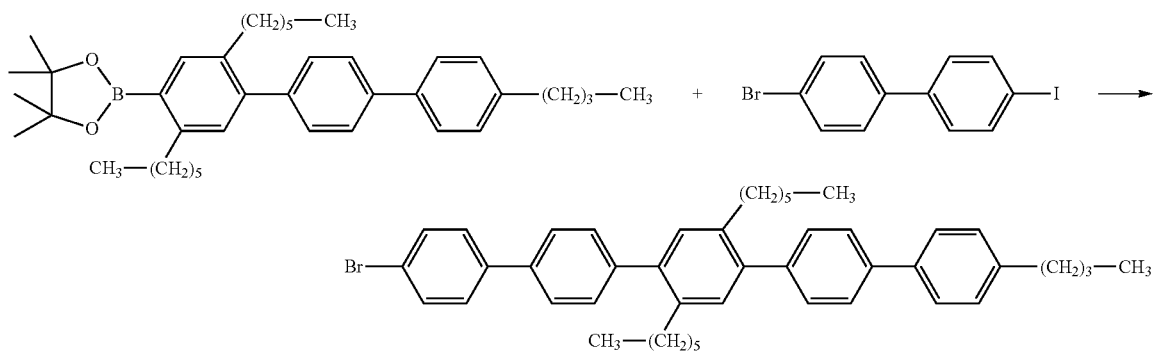

3.00 g of 4-bromo-4'-iodobiphenyl are dissolved in 80.0 ml of toluene (extra pure). 3.00 g of anhydrous sodium carbonate (extra pure), 50.0 ml of demineralised water, 6.20 g of the product from the final step are then added successively. The crude product (yellow-brown crystals) is isolated and subjected to conventional purification. Yellow-brown crystals are obtained.

Step 3.5 one drop of water are added. The reaction mixture is stirred at a temperature of 100° C. for 16 h under a nitrogen atmosphere. The crude product (yellow crystals) is isolated. The product is subjected to conventional purification. Yellow crystals are obtained.

The product has the phase sequence C 103° C. N 199.9° C. I and, extrapolated from a 5% solution in ZLI-4792, a Δ∈ of 0.3 and a Δn of 0.255.

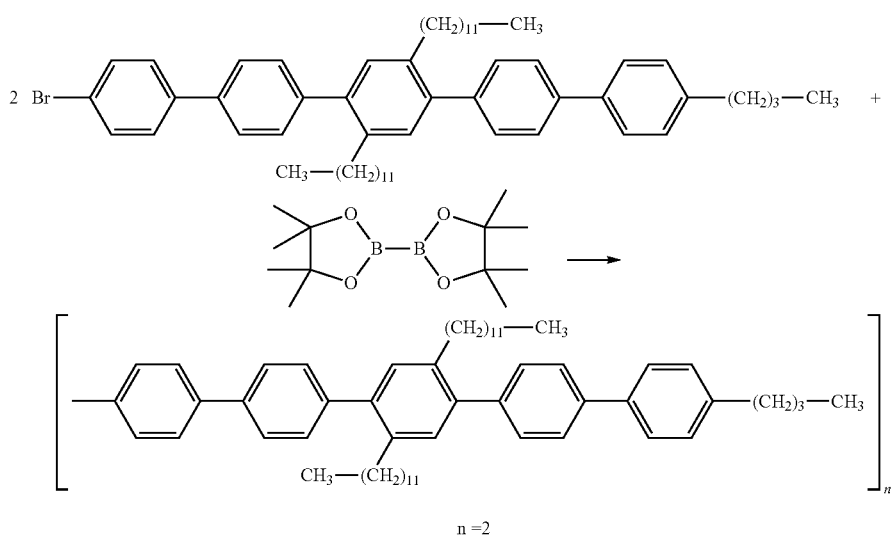

4.70 g of the product from the final step and 0.680 g of bis(pincalto)-diboron are dissolved in 25.0 ml of 1,4-dioxane (extra pure) with gentle warming. Then, firstly 200.0 mg of PdCl$_2$(PCy$_3$)$_2$ (bistricyclohexylphosphinopalladuim dichloride) and subsequently 3.50 g of caesium fluoride and Substance Example 4

The following compound is prepared analogously to Substance Example 3

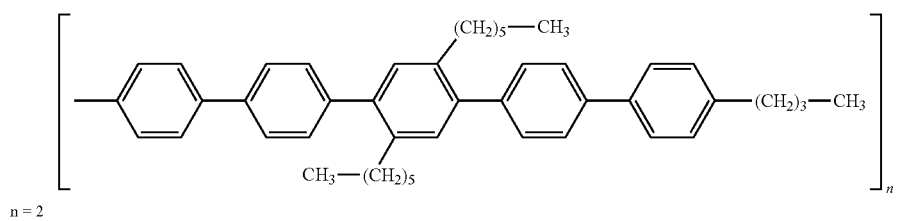

For simplicity, only the final synthetic step is described in detail here.

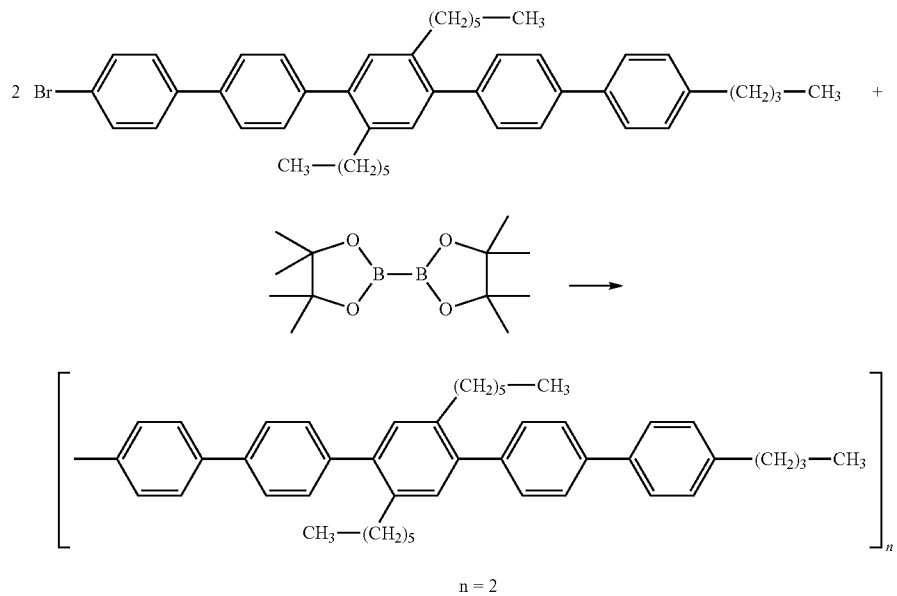

1.70 g of the product from the final step and 0.280 g of bis(pincalto)-diboron are dissolved in 10.0 ml of 1,4-dioxane with gentle warming. Then, firstly 80.0 mg of $PdCl_2(PCy_3)_2$ (bistricyclohexylphosphinopalladuim dichloride) and subsequently 1.40 g of caesium fluoride are added. The reaction mixture is heated under reflux for 16 h under a nitrogen atmosphere. The product is subjected to conventional purification. Yellow crystals are obtained.

The product has the phase sequence: C 154° C. N 283.9° C. I and, extrapolated from a 5% solution in ZLI-4792, a Δε of 3.0 and a Δn of 0.308.

Substance Example 5

The following compound is prepared analogously to Substance Example 3

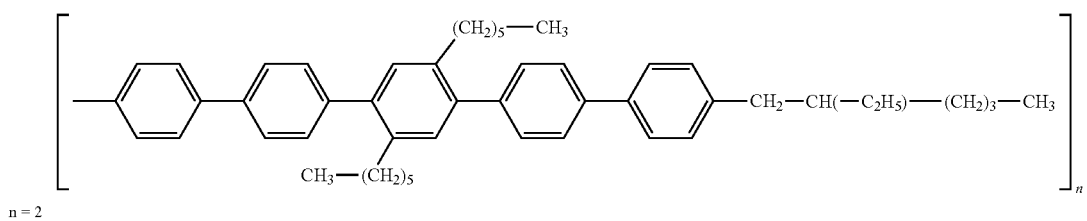

For simplicity, only the final synthetic step is described in detail here.

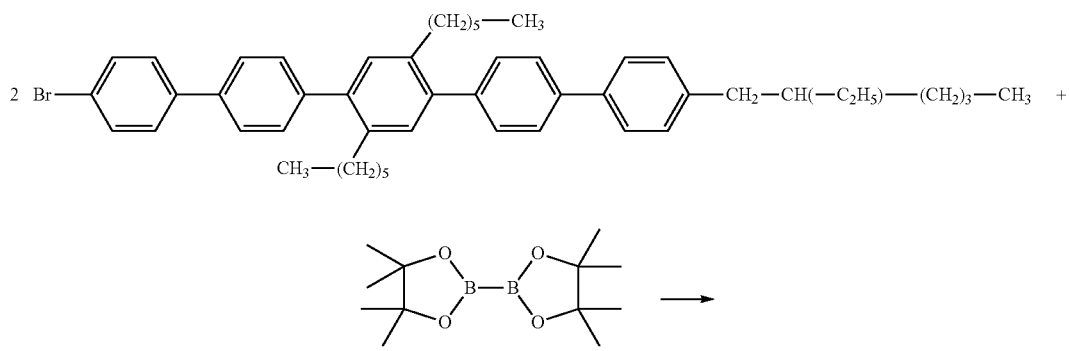

-continued

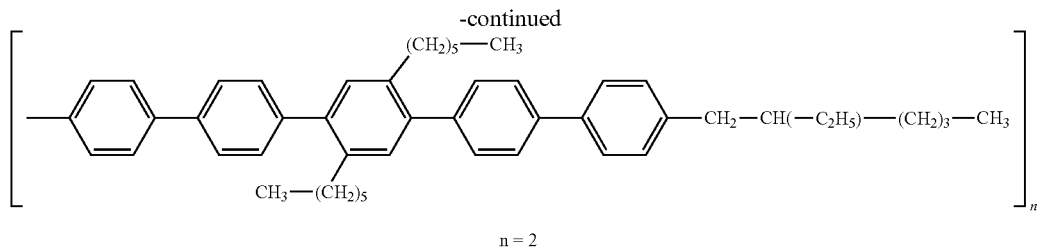

n = 2

5.0 g of the product from the final step and 0.863 g of bis(pincalto)diboron are dissolved in 35.0 ml of 1,4-dioxane with gentle warming. Then, firstly 250 mg of $PdCl_2(PCy_3)_2$ (bistricyclohexylphosphinopalladuim dichloride) and subsequently 1.40 g of caesium fluoride and 1 drop of water are added. The reaction mixture is stirred at a temperature of 100° C. for 16 h under a nitrogen atmosphere. The crude product (an amorphous, yellowish/yellowish-orange mass) is isolated. The product is subjected to conventional purification. Greyish crystals are obtained.

The product has the phase sequence: C 147° C. N 238.4° C. I and, extrapolated from a 10% solution in ZLI-4792, a $\Delta\epsilon$ of 0.4 and a $\Delta n$ of 0.267.

Use Examples

Comparative Example 1

The known liquid-crystalline compound 4'-pentyl-4-cyanobiphenyl (also known as 5CB or K15, Merck KGaA, Darmstadt, Germany) is investigated with respect to its physical properties, in particular in the microwave region, at 20° C.

TABLE 1

Properties of compound K15 at 30 GHz

| T/° C. | $\epsilon_{r, \parallel}$ | $\epsilon_{r, \perp}$ | $\tau$ | $\tan \delta_{\epsilon, r, \parallel}$ | $\tan \delta_{\epsilon, r, \perp}$ | $\eta$ |
|---|---|---|---|---|---|---|
| 20 | 2.87 | 2.55 | 0.110 | 0.0114 | 0.026 | 4.3 |

This compound has a phase sequence of: C 23° C. N 35.1° C. and a $\Delta\epsilon$ of 11.0 at a temperature of 26° C. and a $\Delta\epsilon$ of 9.9 at a temperature of 29° C., and, extrapolated from a 10% solution in ZLI-4792, a $\Delta\epsilon$ of 20.1 and a $\Delta n$ of 0.212.

The compound has very low material quality and is not particularly highly suitable for applications in the microwave region since it has a very narrow phase range and a rather low $\eta$.

Comparative Example 2

A liquid-crystalline substance having the abbreviation PTP(2)TP-6-3 is prepared by the method of Hsu, C. S. Shyu, K. F., Chuang, Y. Y. and Wu, S.-T., Liq. Cryst., 27 (2), (2000), p. 283-287, and investigated with respect to its physical properties, in particular in the microwave region. The compound has a nematic phase and a clearing point of 108° C.

TABLE 2

Properties of compound PTP(2)TP-6-3 at 30 GHz

| T/° C. | $\epsilon_{r, \parallel}$ | $\epsilon_{r, \perp}$ | $\tau$ | $\tan \delta_{\epsilon, r, \parallel}$ | $\tan \delta_{\epsilon, r, \perp}$ | $\eta$ |
|---|---|---|---|---|---|---|
| 20 | 3.17 | 2.38 | 0.249 | 0.0018 | 0.0063 | 40 |
| 22 | 3.22 | 2.44 | 0.242 | 0.0018 | 0.0064 | 38 |

The compound has a phase sequence of: $T_g$–54° C. N 119.2° C. and, extrapolated from a 10% solution in ZLI-4792, a $\Delta\epsilon$ of 1.8 and a $\Delta n$ of 0.393.

The compound is suitable for applications in the microwave region, but it has a low $\Delta\epsilon$, in particular for phase shifters.

TABLE 3

Comparison of the properties of the various examples at 30 GHz and 20° C.

| Example | Liquid cryst. | $\Delta\epsilon$ | $\epsilon_{r, \parallel}$ | $\epsilon_{r, \perp}$ | $\tau$ | $\tan \delta_{\epsilon\, r,\, max.}$ | $\eta$ |
|---|---|---|---|---|---|---|---|
| Comp. 1 | K15 | 20 | 2.87 | 2.55 | 0.110 | 0.026 | 4.3 |
| Comp. 2 | P2-6-3* | 0.4 | 3.17 | 2.38 | 0.249 | 0.0063 | 40 |
| Comp. 2 | P2-6-3* | 0.4 | 3.22§ | 2.44§ | 0.242§ | 0.0064§ | 38§ |
| 1 | M-1 | 0.8 | 3.15 | 2.38 | 0.244 | 0.0057 | 45 |
| 2 | M-2 | t.b.d. | 3.18 | 2.40 | 0.245 | 0.0055 | 46 |
| 3 | M-3 | 0.8 | 3.14 | 2.37 | 0.245 | 0.0054 | 45 |
| 4 | M-4 | 2.4 | 3.18 | 2.39 | 0.248 | 0.0074 | 34 |
| 5 | M-5 | 0.9 | 3.13§ | 2.40§ | 0.233§ | 0.0052§ | 45§ |
| 6 | M-6 | 3.0 | 3.23 | 2.42 | 0.250 | 0.0085 | 30 |

Notes:
*P2-6-3: PTP(2)TP-6-3,
§at T = 22° C. and
t.b.d.: to be determined.

Example 1

A liquid-crystal mixture M-1 having the composition and properties as indicated in the following table is prepared and investigated with respect to its physical properties, in particular in the microwave region.

| Composition | | |
|---|---|---|
| Compound | | |
| No. | Abbreviation | |
| 1 | PTP(2)TP-6-3 | 95.0 |
| 2 | 6*P-1 | 5.0 |
| Σ | | 100.0 |
| Physical properties | | |
| T(N, I) = | | 118.5° C. |
| $n_e$ (20° C., 589.3 nm) = | | t.b.d. |

-continued

| Composition | |
|---|---|
| $n_o$ (20° C., 589.3 nm) = | t.b.d. |
| $\epsilon_\parallel$ (20° C., 1 kHz) = | 3.4 |
| $\Delta\epsilon$ (20° C., 1 kHz) = | +0.8 |
| $k_1$ (20° C.) = | 11.7 pN |
| $K_3$ (20° C.) = | 52.2 pN |

Notes:
t.b.d.: to be determined and

TABLE 4

Properties of mixture M-1 at 30 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.15 | 2.38 | 0.244 | 0.0013 | 0.0057 | 45 |

This mixture is very highly suitable for applications in the microwave region, in particular for phase shifters.

Example 2

A liquid-crystal mixture M-2 having the composition and properties as indicated in the following table is prepared and investigated with respect to its physical properties, in particular in the microwave region.

| Composition | | |
|---|---|---|
| Compound | | |
| No. | Abbreviation | |
| 1 | PTP(2)TP-6-3 | 93.0 |
| 2 | 10*P-1 | 7.0 |
| Σ | | 100.0 |

| Physical properties | |
|---|---|
| T(N, I) = | 115.5° C. |
| $n_e$ (20° C., 589.3 nm) = | t.b.d. |
| $n_o$ (20° C., 589.3 nm) = | t.b.d. |
| $\epsilon_\parallel$ (20° C., 1 kHz) = | t.b.d. |
| $\Delta\epsilon$ (20° C., 1 kHz) = | t.b.d. |

Notes:
t.b.d.: to be determined.

TABLE 5

Properties of mixture M-2 at 30 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.18 | 2.40 | 0.245 | 0.0015 | 0.0055 | 46 |

This mixture is very highly suitable for applications in the microwave region, in particular for phase shifters.

Example 3

A liquid-crystal mixture M-3 having the composition and properties as indicated in the following table is prepared and investigated with respect to its physical properties, in particular in the microwave region.

| Composition | | |
|---|---|---|
| Compound | | |
| No. | Abbreviation | |
| 1 | PTP(2)TP-6-3 | 90.0 |
| 2 | 10*P-3 | 10.0 |
| Σ | | 100.0 |

| Physical properties | |
|---|---|
| T(N, I) = | 116.5° C. |
| $n_e$ (20° C., 589.3 nm) = | t.b.d. |
| $n_o$ (20° C., 589.3 nm) = | t.b.d. |
| $\epsilon_\parallel$ (20° C., 1 kHz) = | 3.4 |
| $\Delta\epsilon$ (20° C., 1 kHz) = | +0.8 |
| $k_1$ (20° C.) = | 12.47 pN |
| $K_3$ (20° C.) = | 51.2 pN |

Notes:
t.b.d.: to be determined.

TABLE 6

Properties of mixture M-3 at 30 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.14 | 2.37 | 0.245 | 0.0015 | 0.0054 | 45 |

This mixture is very highly suitable for applications in the microwave region, in particular for phase shifters.

Example 4

A liquid-crystal mixture M-4 having the composition and properties as indicated in the following table is prepared and investigated with respect to its physical properties, in particular in the microwave region.

| Composition | | |
|---|---|---|
| Compound | | |
| No. | Abbreviation | |
| 1 | PTP(2)TP-3-1 | 10.0 |
| 2 | PTP(2)TP-6-3 | 63.0 |
| 3 | PTP(2)TP-3-O5 | 10.0 |
| 4 | PGUQU-3-F | 5.0 |
| 5 | PU[QGU]$_2$-5-F | 5.0 |
| 6 | 10*P-3 | 7.0 |
| Σ | | 100.0 |

| Physical properties | |
|---|---|
| T(N, I) = | 123.5° C. |
| $n_e$ (20° C., 589.3 nm) = | t.b.d. |
| $n_o$ (20° C., 589.3 nm) = | t.b.d. |
| $\epsilon_\parallel$ (20° C., 1 kHz) = | 5.2 |
| $\Delta\epsilon$ (20° C., 1 kHz) = | 2.4 |
| $k_1$ (20° C.) = | t.b.d. pN |
| $K_3$ (20° C.) = | t.b.d. pN |

Notes:
t.b.d.: to be determined,
PU[QGU]$_2$-5-F: PUQGUQGU-5-F,
Phase sequence: C 86° C. N 236.4° C.I.

TABLE 7

Properties of mixture M-4 at 30 GHz

| T/° C. | $\epsilon_{r,\|}$ | $\epsilon_{r,\perp}$ | $\tau$ | $\tan\delta_{\epsilon,r,\|}$ | $\tan\delta_{\epsilon,r,\perp}$ | $\eta$ |
|---|---|---|---|---|---|---|
| 20 | 3.18 | 2.39 | 0.248 | 0.0021 | 0.0074 | 34 |

This mixture is very highly suitable for applications in the microwave region, in particular for phase shifters. It has, in particular, a relatively high $\Delta\epsilon$.

Example 5

A liquid-crystal mixture M-5 having the composition and properties as indicated in the following table is prepared and investigated with respect to its physical properties, in particular in the microwave region.

| Composition | | |
|---|---|---|
| Compound | | |
| No. | Abbreviation | |
| 1 | PTP(2)TP-6-3 | 70.0 |
| 2 | PTP(c3)TP-4-4 | 10.0 |
| 3 | PT(1,4N)BP-3-4 | 10.0 |
| 4 | 10*P-3 | 10.0 |
| Σ | | 100.0 |

| Physical properties | |
|---|---|
| T(N, I) = | 119.0° C. |
| $n_e$ (20° C., 589.3 nm) = | t.b.d. |
| $n_o$ (20° C., 589.3 nm) = | t.b.d. |
| $\epsilon_{\|}$ (20° C., 1 kHz) = | 3.6 |
| $\Delta\epsilon$ (20° C., 1 kHz) = | +0.9 |
| $k_1$ (20° C.) = | 10.9 pN |
| $K_3$ (20° C.) = | 46.4 pN |

Notes:
t.b.d.: to be determined.

TABLE 8

Properties of mixture M-5 at 30 GHz

| T/° C. | $\epsilon_{r,\|}$ | $\epsilon_{r,\perp}$ | $\tau$ | $\tan\delta_{\epsilon,r,\|}$ | $\tan\delta_{\epsilon,r,\perp}$ | $\eta$ |
|---|---|---|---|---|---|---|
| 22 | 3.13 | 2.40 | 0.233 | 0.0015 | 0.0052 | 45 |

This mixture is very highly suitable for applications in the microwave region, in particular for phase shifters.

Example 6

A liquid-crystal mixture M-6 having the composition and properties as indicated in the following table is prepared.

| Composition | | |
|---|---|---|
| Compound | | |
| No. | Abbreviation | |
| 1 | PTP(2)TP-3-1 | 15.0 |
| 2 | PTP(2)TP-3-3 | 15.0 |
| 3 | PTP(2)TP-3-O5 | 15.0 |
| 4 | PTP(2)TP-6-3 | 42.0 |
| 5 | D(fN)UQU-3-F | 8.0 |
| 6 | 10*P-3 | 5.0 |
| Σ | | 100.0 |

| Physical properties | |
|---|---|
| T(N, I) = | 129.5° C. |
| $n_e$ (20° C., 589.3 nm) = | t.b.d. |
| $n_o$ (20° C., 589.3 nm) = | t.b.d. |
| $\epsilon_{\|}$ (20° C., 1 kHz) = | 6.5 |
| $\Delta\epsilon$ (20° C., 1 kHz) = | 3.0 |
| $k_1$ (20° C.) = | t.b.d. |
| $K_3$ (20° C.) = | t.b.d. |

Notes:
t.b.d.: to be determined and

D(fN)UQU-3-F, phase sequence: C 80° C. N 120° C.I.

TABLE 9

Properties of mixture M-6 at 30 GHz

| T/° C. | $\epsilon_{r,\|}$ | $\epsilon_{r,\perp}$ | $\tau$ | $\tan\delta_{\epsilon,r,\|}$ | $\tan\delta_{\epsilon,r,\perp}$ | $\eta$ |
|---|---|---|---|---|---|---|
| 20 | 3.23 | 2.42 | 0.250 | 0.0023 | 0.0085 | 30 |

This mixture is very highly suitable for applications in the microwave region, in particular for phase shifters. It has, in particular, a relatively high $\Delta\epsilon$.

The invention claimed is:

1. A compound of the of the formula IA in which n and m, independently of one another, denote an integer from 1 to 15, preferably 3 to 12, p denotes an integer from 1 to 4, q denotes an integer from 1 to 6, and (p+q) denotes an integer from 4 to 12.

2. A compound of the of the formula IB

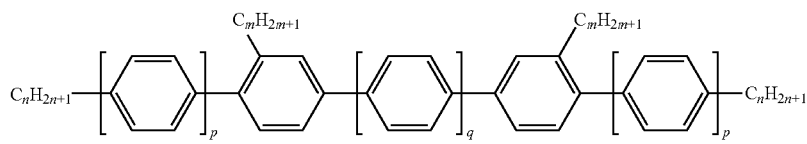

in which
n and m, independently of one another, denote an integer from 1 to 15, preferably 3 to 12,
denotes an integer from 1 to 4,
q denotes an integer from 1 to 6, and
(p+q) denotes an integer from 4 to 12.

3. A compound of one of the formula IA-1 to IA-3

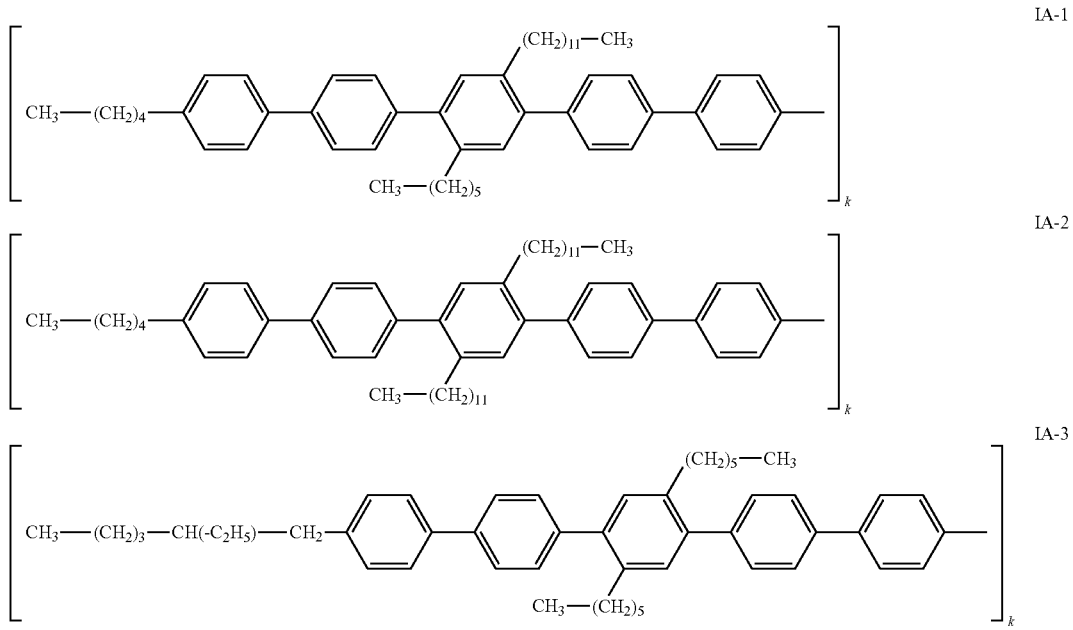

in which
k denotes 2.

4. A compound of the of the formula IB-1

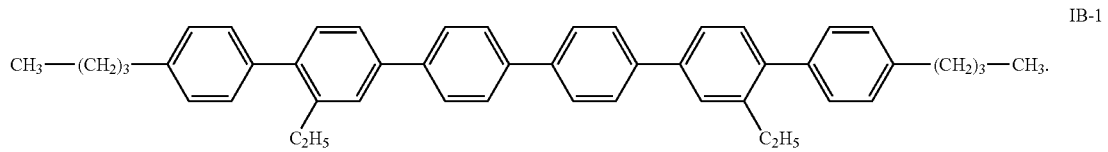

5. A compound of the of the formula IB-2

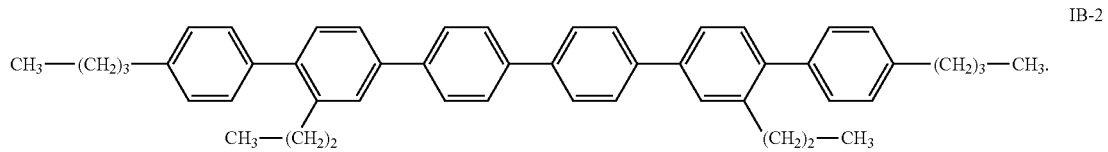

6. A process for the preparation of a compound of the IA according to claim 1, wherein the product or one or more intermediates from an aryl borate compound are linked to an aryl-halogen compound or to an aryl triflate compound by palladium-catalysed homocoupling and/or cross-coupling.

7. A process for the preparation of a compound of the formula IB according to claim 2, wherein the product or one or more intermediates from an aryl borate compound are linked to an aryl-halogen compound or to an aryl triflate compound by palladium-catalysed homocoupling and/or cross-coupling.

8. A process for the preparation of a compound of one of the formula IA-1 to IA-3 according to claim 3, wherein the product or one or more intermediates from an aryl borate compound are linked to an aryl-halogen compound or to an aryl triflate compound by palladium-catalysed homocoupling and/or cross-coupling.

9. A process for the preparation of a compound of the formula IB-1 according to claim 4, wherein the product or one or more intermediates from an aryl borate compound are linked to an aryl-halogen compound or to an aryl triflate compound by palladium-catalysed homocoupling and/or cross-coupling.

10. A process for the preparation of a compound of the formula IB-2 according to claim 5, wherein the product or one or more intermediates from an aryl borate compound are linked to an aryl-halogen compound or to an aryl triflate compound by palladium-catalysed homocoupling and/or cross-coupling.

11. A device for high-frequency technology or for the microwave region and millimeter wave region of the electromagnetic spectrum, comprising:
an antenna, and
a liquid-crystal medium comprising one or more compounds of the formula IA of claim 1.

12. A device for high-frequency technology or for the microwave region and millimeter wave region of the electromagnetic spectrum, comprising:
an antenna, and
a liquid-crystal medium comprising one or more compounds of the formula IB of claim 2.

13. A device for high-frequency technology or for the microwave region and millimeter wave region of the electromagnetic spectrum, comprising:
an antenna, and
a liquid-crystal medium comprising one or more compounds of the formula IA-1 to IA-3 of claim 3.

14. A device for high-frequency technology or for the microwave region and millimeter wave region of the electromagnetic spectrum, comprising:
an antenna, and
a liquid-crystal medium comprising one or more compounds of the formula IB-1 of claim 4.

15. A device for high-frequency technology or for the microwave region and millimeter wave region of the electromagnetic spectrum, comprising:
an antenna, and
a liquid-crystal medium comprising one or more compounds of the formula IB-2 of claim 5.

16. The compound of claim 1 wherein p is 2.
17. The compound of claim 1 wherein q is 1 or 4.
18. The compound of claim 1 wherein (p+q) is 4, 6 or 8.
19. The compound of claim 2 wherein p is 2.
20. The compound of claim 2 wherein q is 1 or 4.
21. The compound of claim 2 wherein (p+q) is 4, 6 or 8.

* * * * *